US009782295B2

(12) United States Patent
Scheller et al.

(10) Patent No.: US 9,782,295 B2
(45) Date of Patent: *Oct. 10, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/276,256

(22) Filed: Sep. 26, 2016

(65) Prior Publication Data

US 2017/0042737 A1 Feb. 16, 2017

Related U.S. Application Data

(63) Continuation of application No. 14/825,057, filed on Aug. 12, 2015, now Pat. No. 9,474,650.

(51) Int. Cl.
*A61B 18/18* (2006.01)
*A61F 9/008* (2006.01)
(Continued)

(52) U.S. Cl.
CPC .......... *A61F 9/00821* (2013.01); *A61B 18/22* (2013.01); *A61B 18/24* (2013.01); *A61F 9/008* (2013.01); *A61M 25/0141* (2013.01); *A61M 25/0147* (2013.01); *A61B 2017/00318* (2013.01); *A61B 2017/2918* (2013.01);
(Continued)

(58) Field of Classification Search
CPC .... A61F 9/008; A61B 18/24; A61M 25/0141; A61M 25/0147
See application file for complete search history.

(56) References Cited

U.S. PATENT DOCUMENTS 3,174,851 A    3/1965   Buehler et al.
4,147,443 A    4/1979   Skobel
(Continued)

FOREIGN PATENT DOCUMENTS

| EP | 0900547 B1 | 3/1999 |
|---|---|---|
| NL | WO 2013/133717 | 9/2013 |
| WO | 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — John R Downey
(74) *Attorney, Agent, or Firm* — Kevin P. Rollins

(57) ABSTRACT

A steerable laser probe may include a handle, an actuation structure, an optic fiber, and a housing tube. The housing tube may include a first housing tube portion having a first stiffness and a second housing tube portion having a second stiffness. The second stiffness may be greater than the first stiffness. The optic fiber may be disposed within the housing tube and within an inner bore of the handle. A compression of the actuation structure may be configured to gradually curve the optic fiber. A decompression of the actuation structure may be configured to gradually straighten the optic fiber.

20 Claims, 40 Drawing Sheets

(51) Int. Cl.
*A61B 18/24* (2006.01)
*A61M 25/01* (2006.01)
*A61B 18/00* (2006.01)
*A61B 18/22* (2006.01)
*A61B 17/00* (2006.01)
*A61B 17/29* (2006.01)

(52) U.S. Cl.
CPC ............ *A61B 2018/00184* (2013.01); *A61B 2018/00589* (2013.01); *A61B 2018/00595* (2013.01); *A61B 2018/2238* (2013.01); *A61F 9/00823* (2013.01); *A61F 2009/00863* (2013.01); *A61F 2009/00885* (2013.01); *A61M 25/0136* (2013.01); *A61M 25/0138* (2013.01)

(56) References Cited

U.S. PATENT DOCUMENTS

| | | |
|---|---|---|
| 4,744,360 A | 5/1988 | Bath |
| 5,190,050 A | 3/1993 | Nitzsche |
| 5,228,852 A | 7/1993 | Goldsmith et al. |
| 5,257,988 A | 11/1993 | L'Esperance, Jr. |
| 5,322,064 A | 6/1994 | Lundquist |
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,735,842 A | 4/1998 | Krueger et al. |
| 5,855,577 A | 1/1999 | Murphy-Chutorian et al. |
| 5,873,865 A | 2/1999 | Horzewski et al. |
| 5,951,544 A | 9/1999 | Konwitz |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,330,837 B1 | 12/2001 | Charles et al. |
| 6,352,531 B1 | 3/2002 | O'Connor et al. |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sherts et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,872,214 B2 | 3/2005 | Sonnenschein et al. |
| 6,984,230 B2 | 1/2006 | Scheller et al. |
| 7,004,957 B1 | 2/2006 | Dampney et al. |
| 7,226,444 B1 | 6/2007 | Ellman et al. |
| 7,303,533 B2 | 12/2007 | Johansen et al. |
| 7,402,158 B2 | 7/2008 | Scheller et al. |
| 7,555,327 B2 | 6/2009 | Matlock |
| 7,632,242 B2 | 12/2009 | Griffin et al. |
| 7,766,904 B2 | 8/2010 | McGowan, Sr. et al. |
| 7,935,108 B2 | 5/2011 | Baxter et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,951,245 B2 | 2/2015 | Scheller et al. |
| 8,968,277 B2 | 3/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0154379 A1 | 7/2005 | McGowan, Sr. et al. |
| 2005/0157985 A1 | 7/2005 | McGowan, Sr. et al. |
| 2005/0234437 A1 | 10/2005 | Baxter et al. |
| 2005/0272975 A1 | 12/2005 | McWeeney et al. |
| 2005/0277874 A1 | 12/2005 | Selkee |
| 2006/0129175 A1 | 6/2006 | Griffin et al. |
| 2006/0178674 A1 | 8/2006 | McIntyre |
| 2007/0185514 A1 | 8/2007 | Kirchhevel |
| 2007/0260231 A1 | 11/2007 | Rose et al. |
| 2008/0132761 A1 | 6/2008 | Sonnenschein et al. |
| 2008/0287938 A1 | 11/2008 | Scheller et al. |
| 2009/0018393 A1 | 1/2009 | Dick et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0191224 A1 | 7/2010 | Butcher |
| 2010/0268234 A1 | 10/2010 | Aho et al. |
| 2010/0331883 A1 | 12/2010 | Schmitz et al. |
| 2011/0028947 A1 | 2/2011 | Scheller et al. |
| 2011/0144630 A1 | 6/2011 | Loeb |
| 2012/0116361 A1 | 5/2012 | Hanlon et al. |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 | 4/2013 | Mansour |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1 | 2/2015 | Scheller et al. |

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

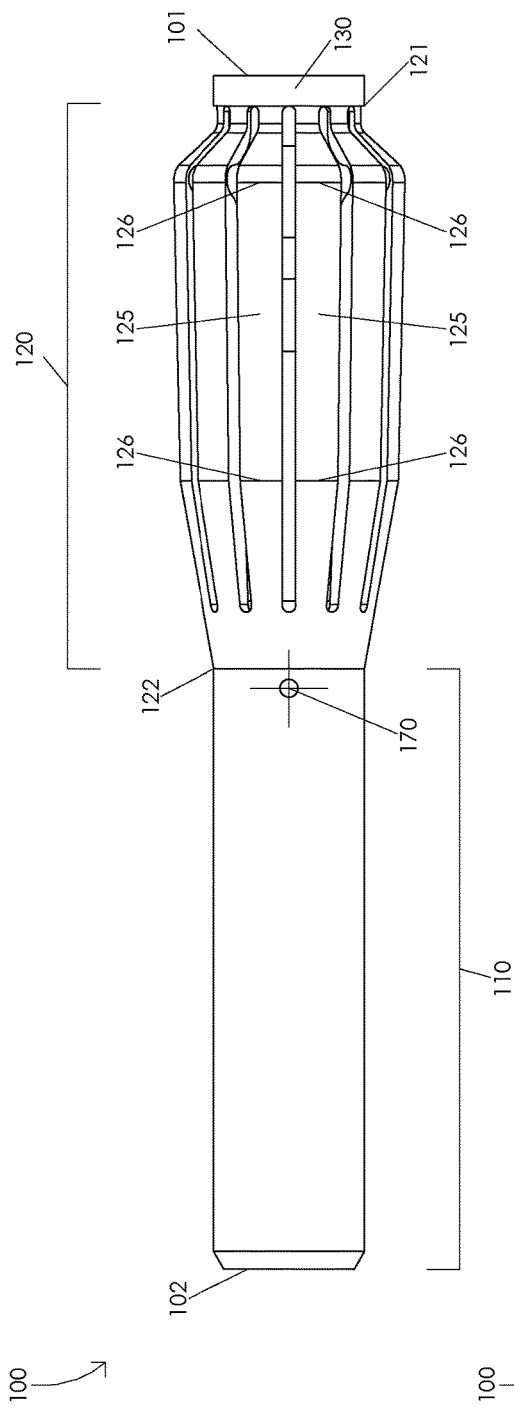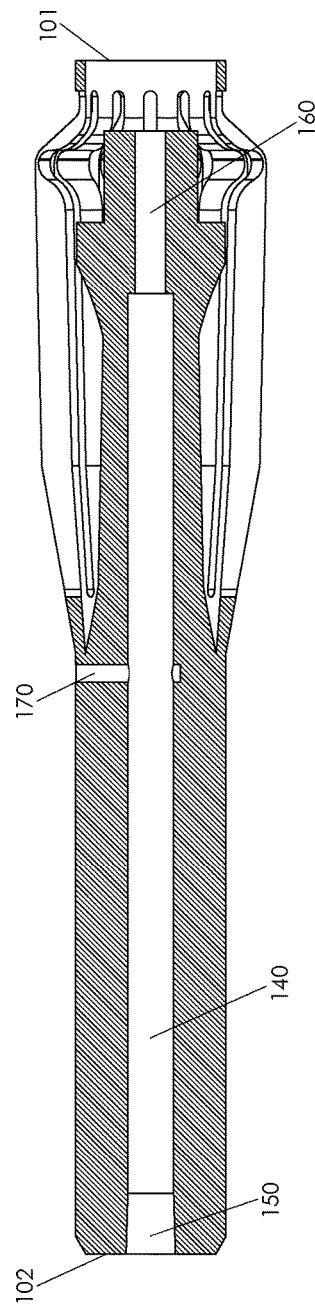
FIG. 1A
FIG. 1B

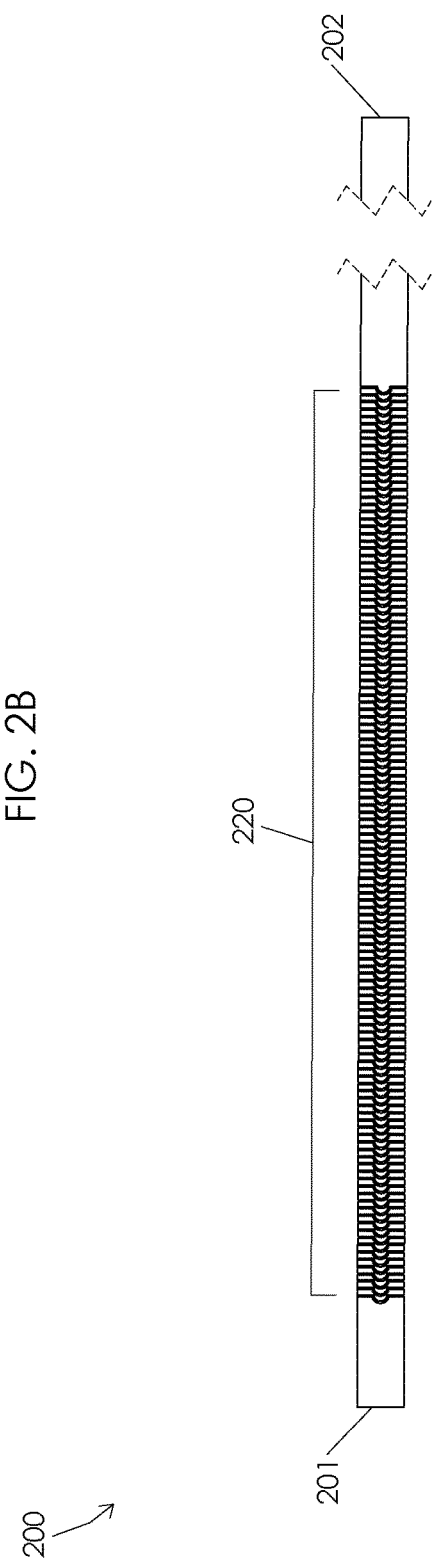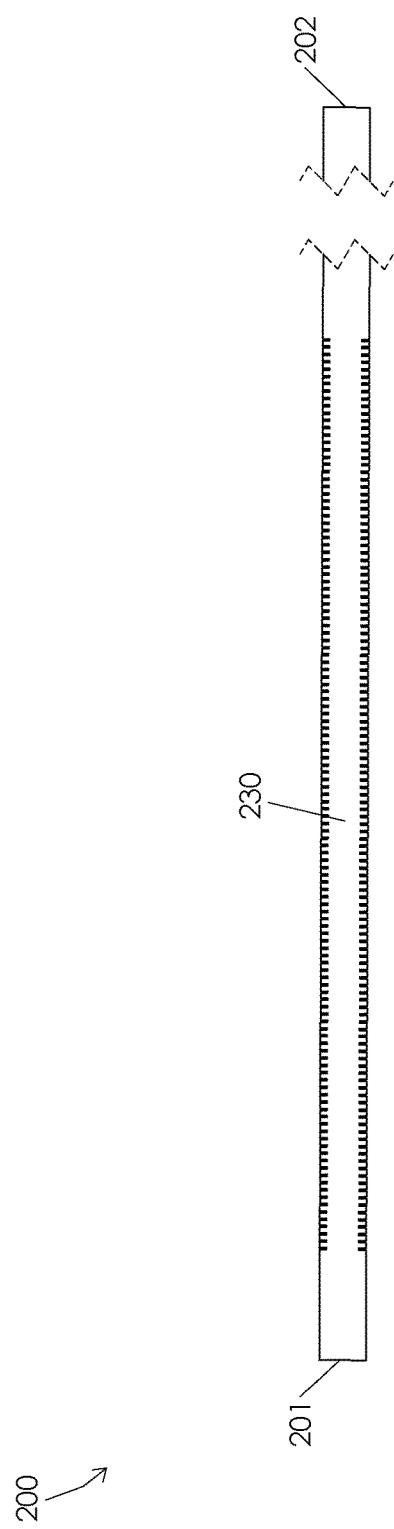

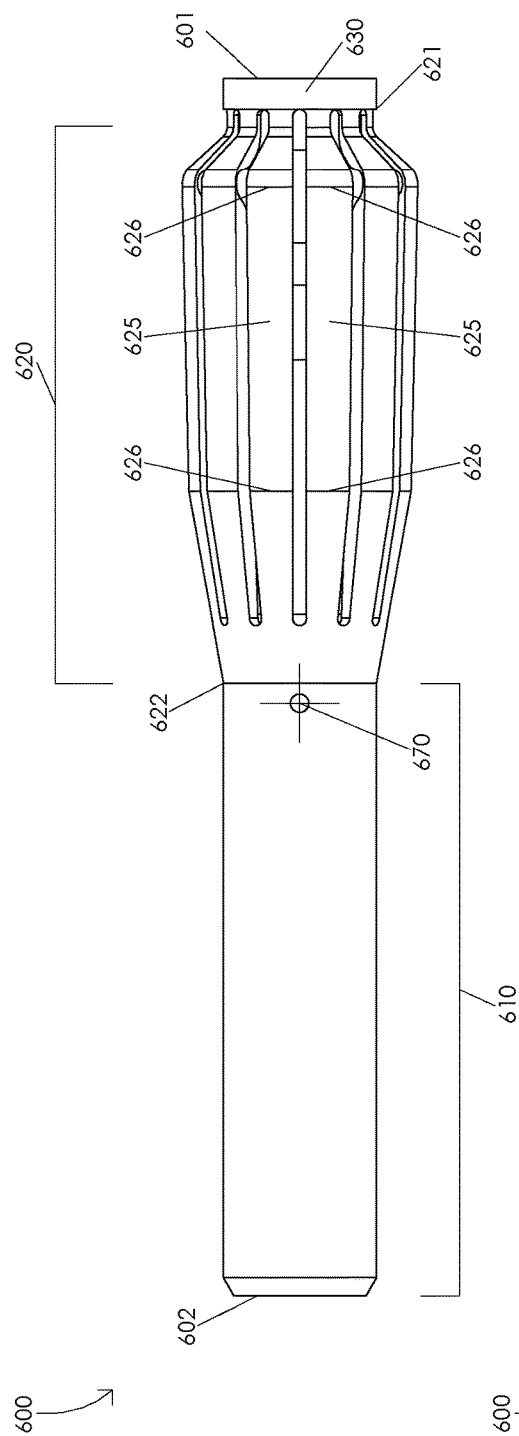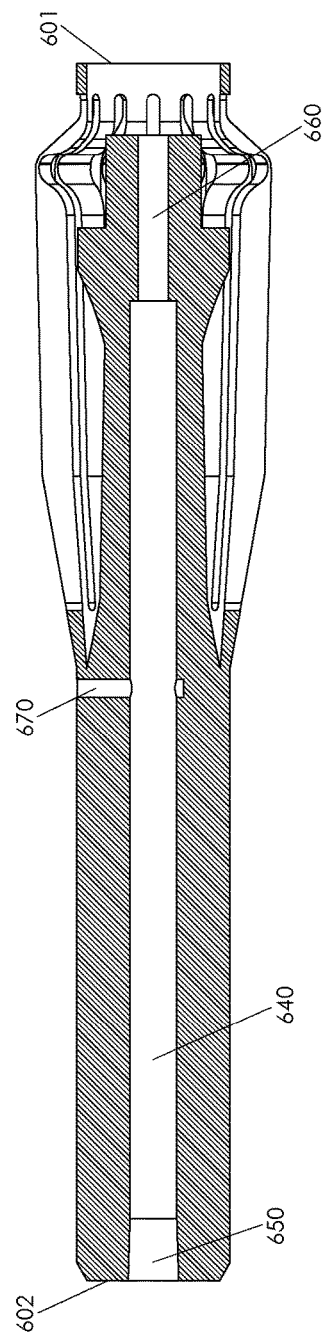

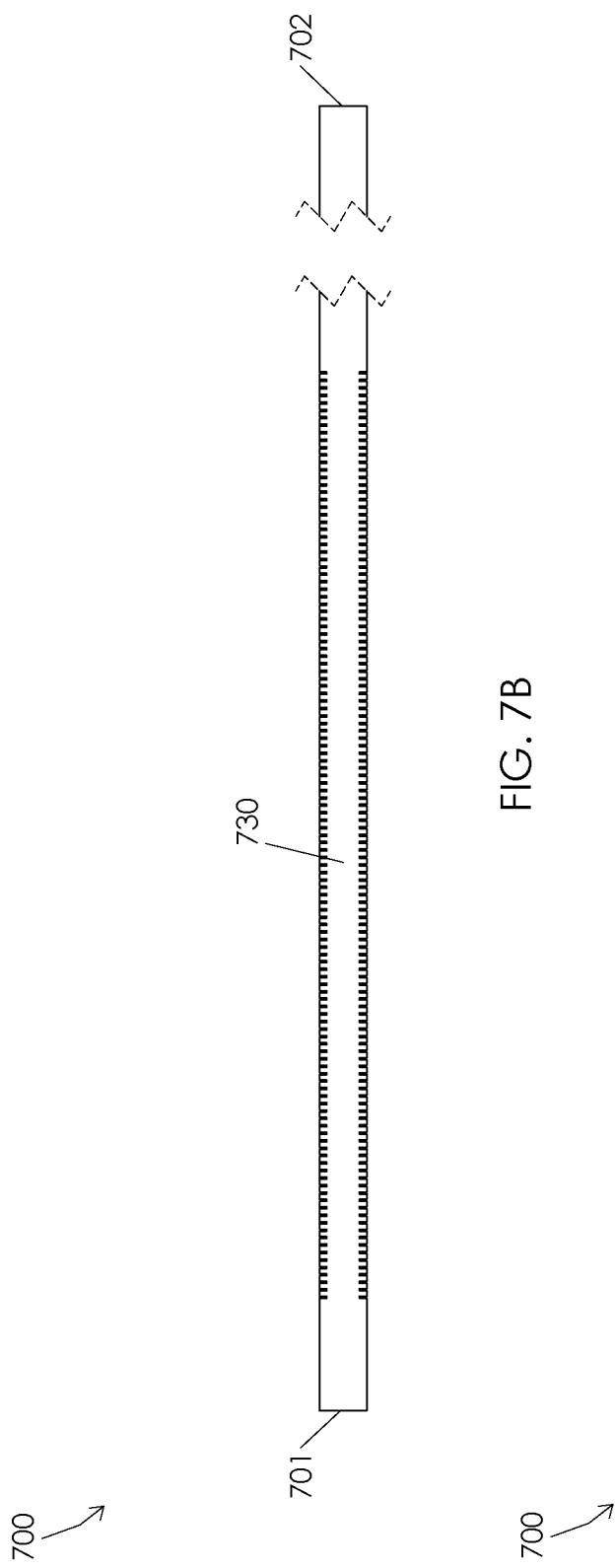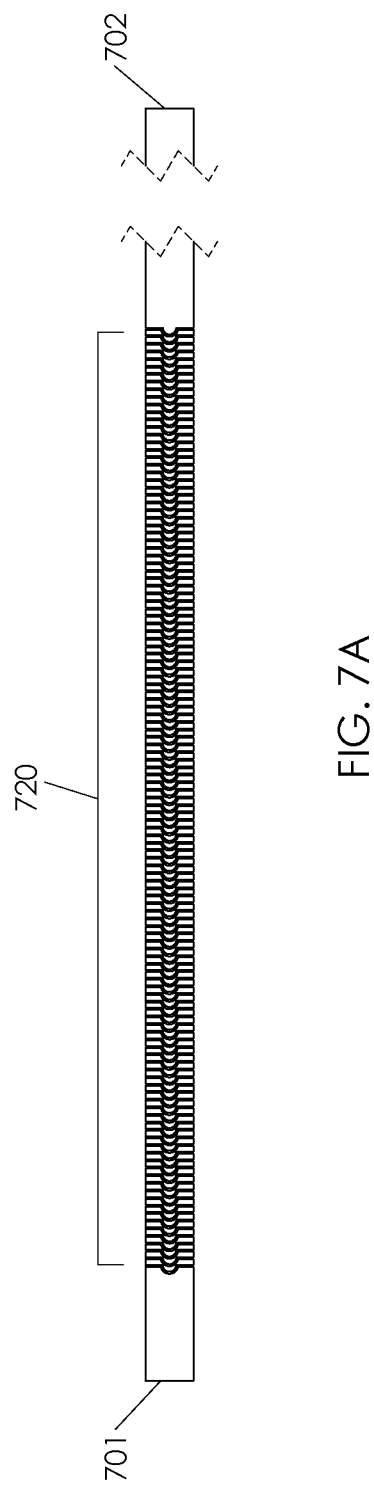

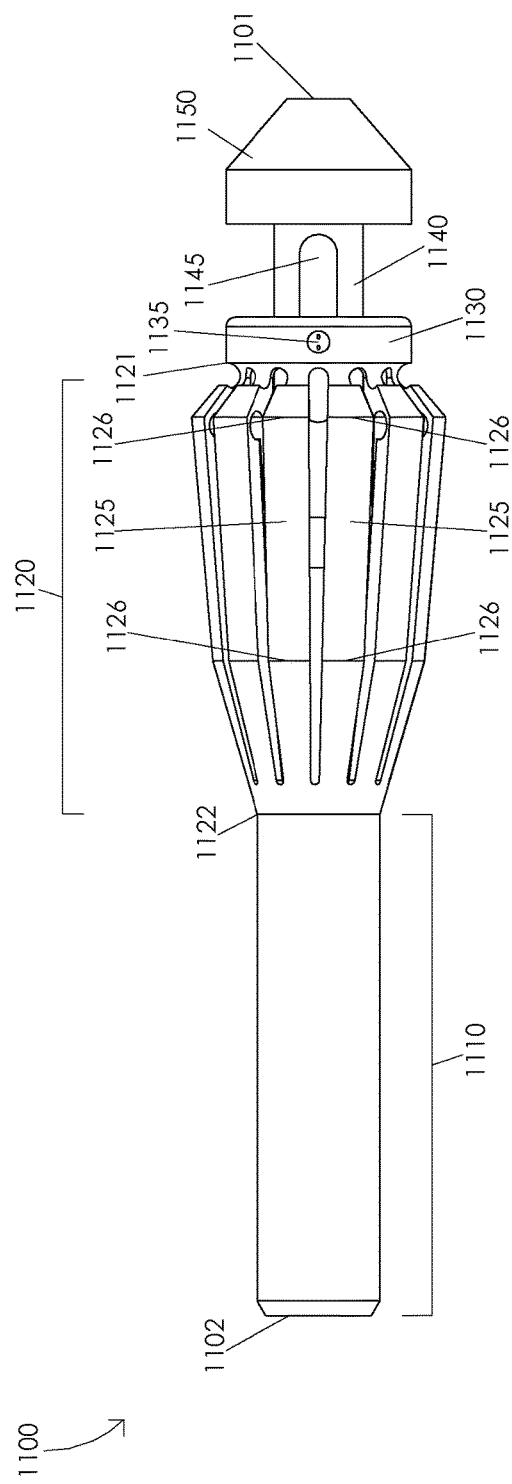
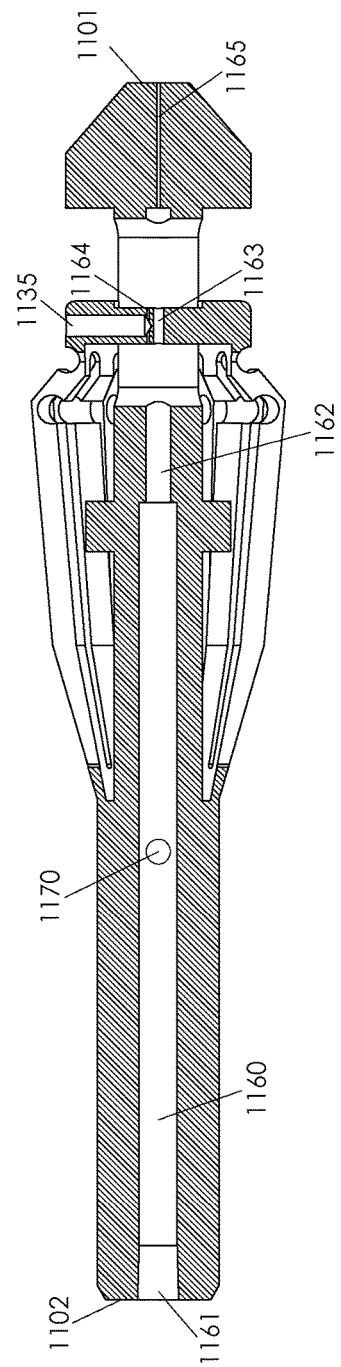
FIG. 11A
FIG. 11B

STEERABLE LASER PROBE

CROSS-REFERENCE TO RELATED APPLICATIONS

This application is a continuation of prior application Ser. No. 14/825,057, filed Aug. 12, 2015.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle, an actuation structure, an optic fiber, and a housing tube. Illustratively, the housing tube may comprise a first housing tube portion having a first stiffness and a second housing tube portion having a second stiffness. In one or more embodiments, the second stiffness may be greater than the first stiffness. Illustratively, the optic fiber may be disposed within the housing tube and within an inner bore of the handle. In one or more embodiments, a portion of the optic fiber may be fixed to an inner portion of the housing tube, e.g., by a biocompatible adhesive or any other suitable means.

Illustratively, a compression of the actuation structure may be configured to extend the housing tube relative to a handle proximal end. In one or more embodiments, an extension of the housing tube relative to the handle proximal end may be configured to gradually compress the first housing tube portion causing the housing tube to gradually curve. Illustratively, a gradual curving of the housing tube may be configured to cause the optic fiber to gradually curve.

In one or more embodiments, a decompression of the actuation structure may be configured to retract the housing tube relative to the handle proximal end. Illustratively, a retraction of the housing tube relative to the handle proximal end may be configured to gradually decompress the first housing tube portion causing the housing tube to gradually straighten. In one or more embodiments, a gradual straightening of the housing tube may be configured to cause the optic fiber to gradually straighten.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 2A, 2B, and 2C are schematic diagrams illustrating a housing tube;

FIGS. 6A and 6B are schematic diagrams illustrating a handle;

FIGS. 7A, 7B, and 7C are schematic diagrams illustrating a housing tube;

FIGS. 11A and 11B are schematic diagrams illustrating a handle;

DETAILED DESCRIPTION OF AN ILLUSTRATIVE EMBODIMENT

Figure 2C:
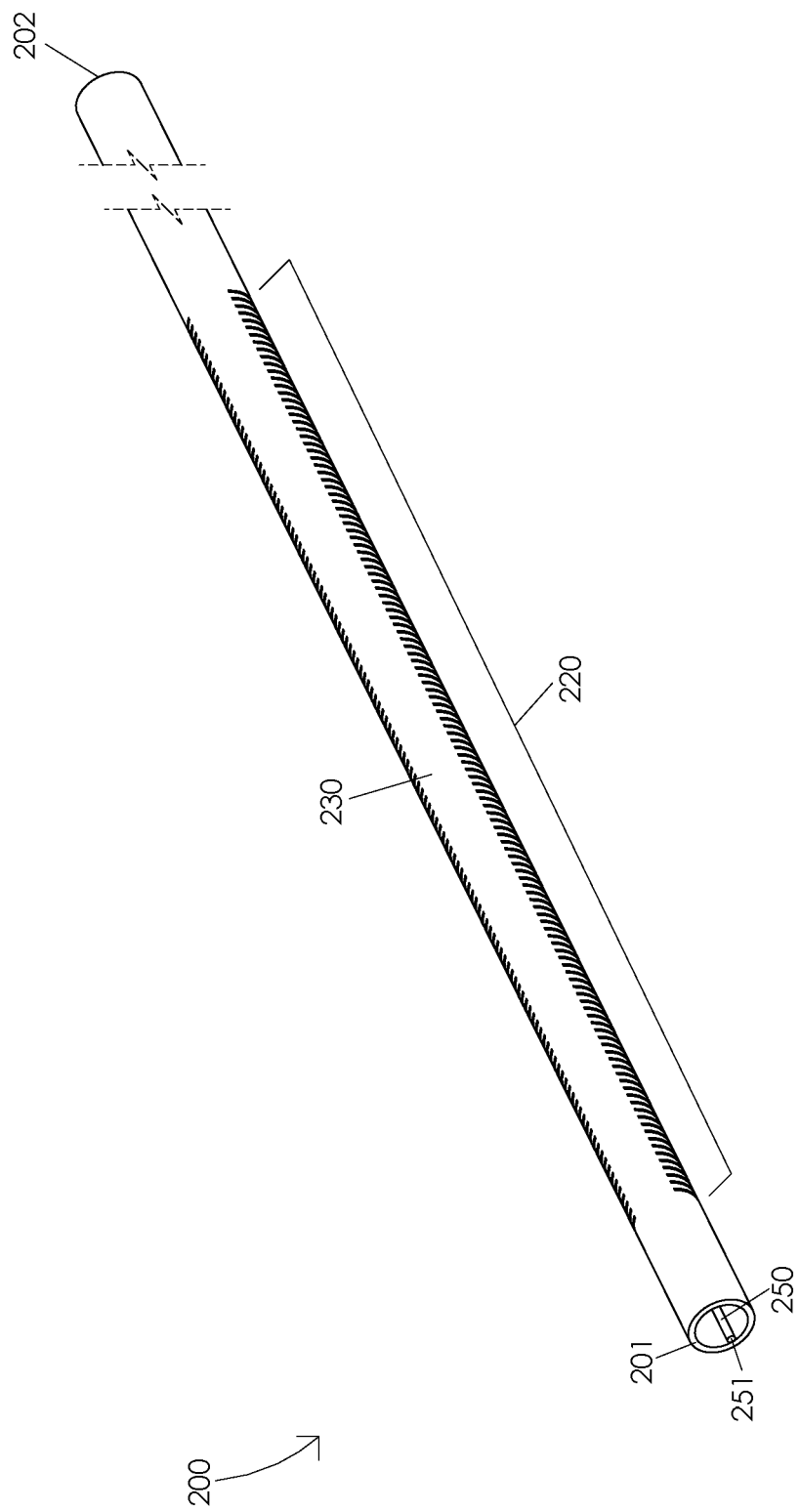

FIGS. 1A and 1B are schematic diagrams illustrating a handle 100. FIG. 1A illustrates a top view of handle 100. In one or more embodiments, handle 100 may comprise a handle distal end 101, a handle proximal end 102, a handle base 110, and an actuation structure 120. Illustratively, actuation structure 120 may comprise an actuation structure distal end 121 and an actuation structure proximal end 122. In one or more embodiments, actuation structure 120 may comprise a plurality of actuation arms 125. Illustratively, each actuation arm 125 may comprise at least one extension mechanism 126. In one or more embodiments, actuation structure 120 may comprise a shape memory material configured to project actuation structure distal end 121 a first distance from actuation structure proximal end 122, e.g., when actuation structure 120 is fully decompressed. Illustratively, actuation structure 120 may comprise a shape memory material configured to project actuation structure distal end 121 a second distance from actuation structure proximal end 122, e.g., when actuation structure 120 is fully compressed. In one or more embodiments, the second distance from actuation structure proximal end 122 may be greater than the first distance from actuation structure proximal end 122. Actuation structure 120 may be manufactured from any suitable material, e.g., polymers, metals, metal alloys, etc., or from any combination of suitable materials.

Illustratively, actuation structure 120 may be compressed by an application of a compressive force to actuation structure 120. In one or more embodiments, actuation structure 120 may be compressed by an application of one or more compressive forces located at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 from any rotational position of a plurality of rotational positions of handle 100.

In one or more embodiments, actuation structure 120 may be compressed by an application of a compressive force to any one or more of the plurality of actuation arms 125. Illustratively, each actuation arm 125 may be configured to actuate independently. In one or more embodiments, each actuation arm 125 may be connected to one or more of the plurality of actuation arms 125 wherein an actuation of a particular actuation arm 125 may be configured to actuate every actuation arm 125 of the plurality of actuation arms 125. Illustratively, one or more actuation arms 125 may be configured to actuate in pairs or groups. For example, an actuation of a first actuation arm 125 may be configured to actuate a second actuation arm 125.

In one or more embodiments, a compression of actuation structure 120, e.g., due to an application of a compressive force to a particular actuation arm 125, may be configured to actuate the particular actuation arm 125. Illustratively, an actuation of the particular actuation arm 125 may be configured to actuate every actuation arm 125 of the plurality of actuation arms 125. In one or more embodiments, an application of a compressive force to a particular actuation arm 125 may be configured to extend at least one extension mechanism 126 of the particular actuation arm 125. Illustratively, a particular actuation arm 125 may be configured to extend a first length from handle base 110. An extension of an extension mechanism 126 of the particular actuation arm 125, e.g., due to an application of a compressive force to the particular actuation arm 125, may be configured to extend the particular actuation arm 125 a second length from handle base 110. Illustratively, the second length from handle base 110 may be greater than the first length from handle base 110.

In one or more embodiments, handle 100 may comprise an actuation ring 130 fixed to actuation structure distal end 121. Illustratively, a compression of actuation structure 120 may be configured to gradually extend actuation ring 130 from handle base 110. For example, actuation ring 130 may be configured to extend a first distance from actuation structure proximal end 122, e.g., when actuation structure 120 is fully decompressed. Actuation ring 130 may be configured to extend a second distance from actuation structure proximal end 122, e.g., due to a compression of actuation structure 120. Illustratively, the second distance from actuation structure proximal end 122 may be greater than the first distance from actuation structure proximal end 122.

FIG. 1B illustrates a cross-sectional view of handle 100. In one or more embodiments, handle 100 may comprise an inner bore 140, an inner bore proximal taper 150, a piston tube housing 160, and a fixation pin housing 170. Handle 100 may be manufactured from any suitable material, e.g., polymers, metals, metal alloys, etc., or from any combination of suitable materials.

FIGS. 2A, 2B, and 2C are schematic diagrams illustrating a housing tube 200. In one or more embodiments, housing tube 200 may comprise a housing tube distal end 201 and a housing tube proximal end 202. Housing tube 200 may be manufactured from any suitable material, e.g., polymers, metals, metal alloys, etc., or from any combination of suitable materials. FIG. 2A illustrates a housing tube 200 oriented to illustrate a first housing tube portion 220. Illustratively, first housing tube portion 220 may have a first stiffness. FIG. 2B illustrates a housing tube 200 oriented to illustrate a second housing tube portion 230. Illustratively, second housing tube portion 230 may have a second stiffness. In one or more embodiments, the second stiffness may be greater than the first stiffness. Illustratively, first housing tube portion 220 may comprise a first material having a first stiffness. In one or more embodiments, second housing tube portion 230 may comprise a second material having a second stiffness. Illustratively, the second stiffness may be greater than the first stiffness.

In one or more embodiments, first housing tube portion 220 may comprise one or more apertures configured to produce a first stiffness of first housing tube portion 220. Illustratively, second housing tube portion 230 may comprise a solid portion of housing tube 200 having a second stiffness. In one or more embodiments, the second stiffness may be greater than the first stiffness. Illustratively, first housing tube portion 220 may comprise one or more apertures configured to produce a first stiffness of first housing tube portion 220. In one or more embodiments, second housing tube portion 230 may comprise one or more apertures configured to produce a second stiffness of second housing tube portion 230. Illustratively, the second stiffness may be greater than the first stiffness.

In one or more embodiments, first housing tube portion 220 may comprise a plurality of slits configured to separate one or more solid portions of housing tube 200. Illustratively, a plurality of slits may be cut, e.g., laser cut, into first housing tube portion 220. In one or more embodiments, first housing tube portion 220 may comprise a plurality of slits configured to minimize a force of friction between housing tube 200 and a cannula, e.g., as housing tube 200 is inserted into the cannula or as housing tube 200 is extracted from the cannula. For example, each slit of the plurality of slits may comprise one or more arches configured to minimize a force of friction between housing tube 200 and a cannula.

FIG. 2C illustrates an angled view of housing tube 200. Illustratively, an optic fiber 250 may be disposed within housing tube 200. In one or more embodiments, optic fiber 250 may be disposed within housing tube 200 wherein an optic fiber distal end 251 may be adjacent to housing tube distal end 201. Illustratively, optic fiber 250 may be disposed within housing tube 200 wherein a portion of optic fiber 250 may be adjacent to a portion of first housing tube portion 220. In one or more embodiments, a portion of optic fiber 250 may be fixed to an inner portion of housing tube 200, e.g., by a biocompatible adhesive or any other suitable means.

Figure 3:
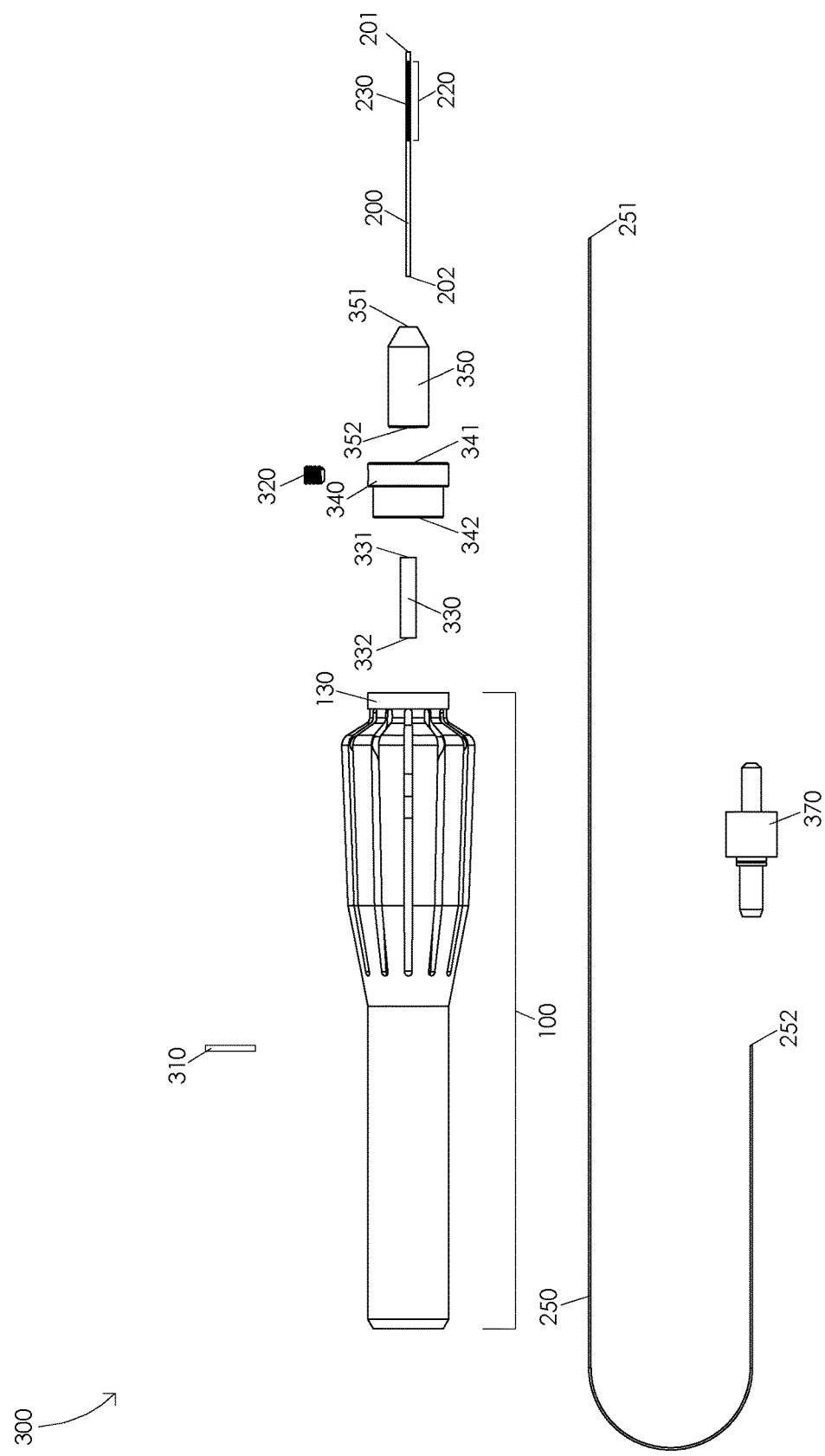
FIG. 3 is a schematic diagram illustrating an exploded view of a steerable laser probe assembly.

FIG. 3 is a schematic diagram illustrating an exploded view of a steerable laser probe assembly 300. In one or more embodiments, steerable laser probe assembly 300 may comprise a handle 100, a housing tube 200 having a housing tube distal end 201 and a housing tube proximal end 202, an optic fiber 250 having an optic fiber distal end 251 and an optic fiber proximal end 252, a fixation pin 310, a fixation mechanism 320, a piston tube 330 having a piston tube distal end 331 and a piston tube proximal end 332, an outer nosecone 340 having an outer nosecone distal end 341 and an outer nosecone proximal end 342, an inner nosecone 350 having an inner nosecone distal end 351 and an inner nosecone proximal end 352, and a light source interface 370. Illustratively, light source interface 370 may be configured to interface with optic fiber proximal end 252. In one or more embodiments, light source interface 370 may comprise a standard light source connecter, e.g., an SMA connector.

Illustratively, piston tube distal end 331 may be fixed to inner nosecone proximal end 352; housing tube proximal end 202 may be fixed to inner nosecone distal end 351; and outer nosecone 340 may be fixed to actuation structure 120, e.g., outer nosecone proximal end 342 may be fixed to actuation ring 130. In one or more embodiments, fixation mechanism 320 may be configured to attach outer nosecone 340 and inner nosecone 350, e.g., outer nosecone distal end 341 may be fixed to inner nosecone proximal end 352. Illustratively, fixation mechanism 320 may comprise a set screw configured to firmly attach outer nosecone 340 and inner nosecone 350. In one or more embodiments, fixation mechanism 320 may comprise an adhesive material configured to attach outer nosecone 340 and inner nosecone 350, or fixation mechanism 320 may comprise one or more magnets configured to attach outer nosecone 340 and inner nosecone 350. Piston tube 330, outer nosecone 340, and inner nosecone 350 may be manufactured from any suitable material, e.g., polymers, metals, metal alloys, etc., or from any combination of suitable materials. Illustratively, piston tube 330 and inner nosecone 350 may be manufactured as a unit. In one or more embodiments, outer nosecone 340 and inner nosecone 350 may be manufactured as a unit. For example, piston tube 330, outer nosecone 340, and inner nosecone 350 may be manufactured as a unit.

In one or more embodiments, fixation pin 310 may be disposed within fixation pin housing 170. Illustratively, optic fiber 250 may be disposed within inner bore 140, fixation pin housing 170, piston tube housing 160, piston tube 330, outer nosecone 340, inner nosecone 350, and housing tube 200. In one or more embodiments, fixation pin 310 may be configured to fix optic fiber 250 in a position relative to handle 100, e.g., at fixation pin housing 170. Illustratively, optic fiber 250 may be disposed within housing tube 200 wherein optic fiber distal end 251 may be adjacent to housing tube distal end 201. In one or more embodiments, optic fiber 250 may be disposed within housing tube 200 wherein optic fiber 250 may be adjacent to a first housing tube portion 220. Illustratively, a portion of optic fiber 250 may be fixed to an inner portion of housing tube 200, e.g., by a biocompatible adhesive or any other suitable fixation means.

In one or more embodiments, a compression of actuation structure 120 may be configured to gradually extend actuation ring 130, piston tube 330, outer nosecone 340, inner nosecone 350, and housing tube 200 relative to handle base 110. Illustratively, optic fiber 250 may be both fixed in a position relative to handle base 110, e.g., by fixation pin 310, and fixed to an inner portion of housing tube 200. In one or more embodiments, as housing tube 200 is extended relative to handle base 110, e.g., due to a compression of actuation structure 120, optic fiber 250 may be configured to resist a portion of housing tube 200, e.g., a first housing tube portion 220, from extending relative to handle base 110. Illustratively, as housing tube 200 is gradually extended relative to handle base 110, optic fiber 250 may be configured to gradually compress a first housing tube portion 220 of housing tube 200 causing housing tube 200 to gradually curve. In one or more embodiments, a gradual curving of housing tube 200 may be configured to gradually curve optic fiber 250.

Illustratively, a decompression of actuation structure 120 may be configured to gradually retract actuation ring 130, piston tube 330, outer nosecone 340, inner nosecone 350, and housing tube 200 relative to handle base 110. In one or more embodiments, as housing tube 200 is gradually retracted relative to handle base 110, optic fiber 250 may be configured to gradually decompress a first housing tube portion 220 of housing tube 200 causing housing tube 200 to gradually straighten. For example, a decompression of actuation structure 120 may be configured to reduce a compressive force applied, e.g., by optic fiber 250, to an inner portion of housing tube 200 causing housing tube 200 to gradually straighten. Illustratively, a gradual straightening of housing tube 200 may be configured to gradually straighten optic fiber 250.

Figure 4A:
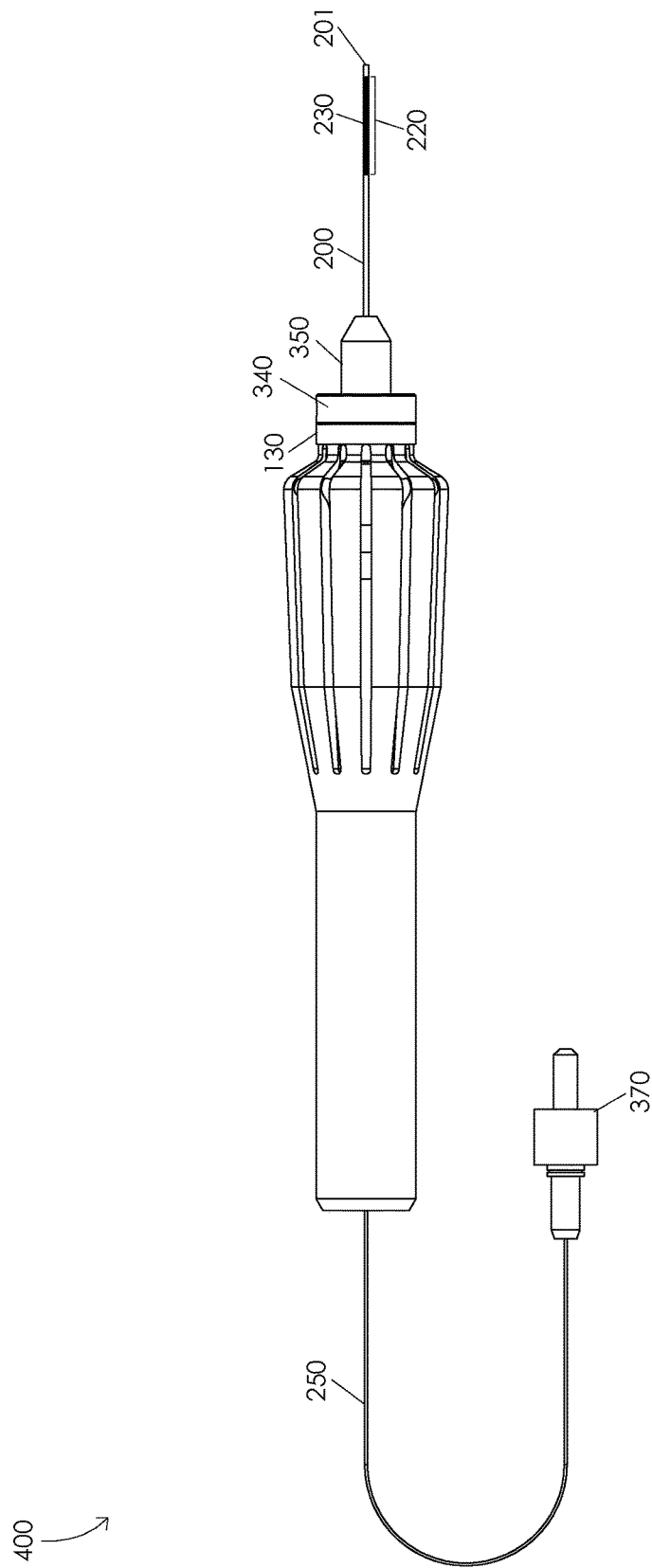
FIGS. 4A, 4B, 4C, 4D, and 4E illustrate a gradual curving of an optic fiber.

FIGS. 4A, 4B, 4C, 4D, and 4E illustrate a gradual curving of an optic fiber 250. FIG. 4A illustrates a straight optic fiber 400. In one or more embodiments, optic fiber 250 may comprise a straight optic fiber 400, e.g., when actuation ring 130 is fully retracted relative to handle base 110. Illustratively, optic fiber 250 may comprise a straight optic fiber 400, e.g., when actuation structure 120 is fully decompressed. In one or more embodiments, optic fiber 250 may comprise a straight optic fiber 400, e.g., when housing tube 200 is fully retracted relative to handle base 110. Illustratively, a line tangent to optic fiber distal end 251 may be parallel to a line tangent to housing tube proximal end 202, e.g., when optic fiber 250 comprises a straight optic fiber 400.

Figure 4B:
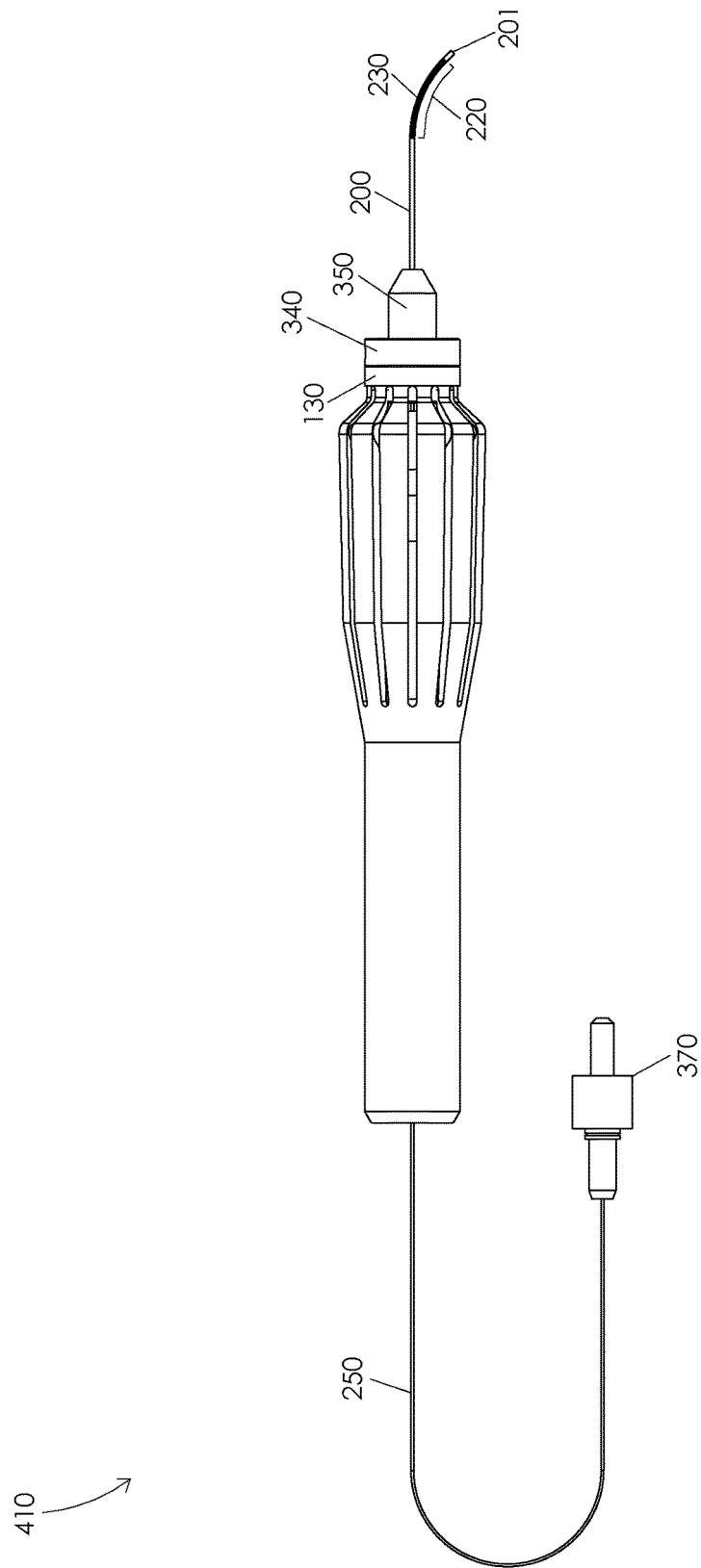

FIG. 4B illustrates an optic fiber in a first curved position 410. In one or more embodiments, a compression of a fully decompressed actuation structure 120 may be configured to gradually curve optic fiber 250 from a straight optic fiber 400 to an optic fiber in a first curved position 410. Illustratively, a compression of actuation structure 120 may be configured to gradually extend housing tube 200 relative to handle base 110. In one or more embodiments, a gradual extension of housing tube 200 relative to handle base 110 may be configured to cause optic fiber 250 to provide a compressive force to an inner portion of housing tube 200. For example, optic fiber 250 may be configured to provide a compressive force configured to oppose an extension of an inner portion of housing tube 200.

Illustratively, an application of a compressive force to an inner portion of housing tube 200, e.g., by extending housing tube 200 relative to handle base 110, may be configured to compress a first housing tube portion 220 of housing tube 200. For example, optic fiber 250 may be fixed in a position relative to handle base 110 and fixed to an inner portion of housing tube 200. In one or more embodiments, as housing tube 200 is gradually extended relative to handle base 110, optic fiber 250 may be configured to resist an inner portion of housing tube 200 from being extended relative to handle base 110 causing the inner portion of housing tube 200 to gradually be compressed. Illustratively, an application of a compressive force to an inner portion of housing tube 200 may be configured to gradually curve housing tube 200. In one or more embodiments, a gradual curving of housing tube 200 may be configured to gradually curve optic fiber 250 from a straight optic fiber 400 to an optic fiber in a first curved position 410.

Illustratively, a line tangent to optic fiber distal end 251 may intersect a line tangent to housing tube proximal end 202 at a first angle, e.g., when optic fiber 250 comprises an optic fiber in a first curved position 410. In one or more embodiments, the first angle may comprise any angle greater than zero degrees. For example, the first angle may comprise a 45 degree angle.

Figure 4C:
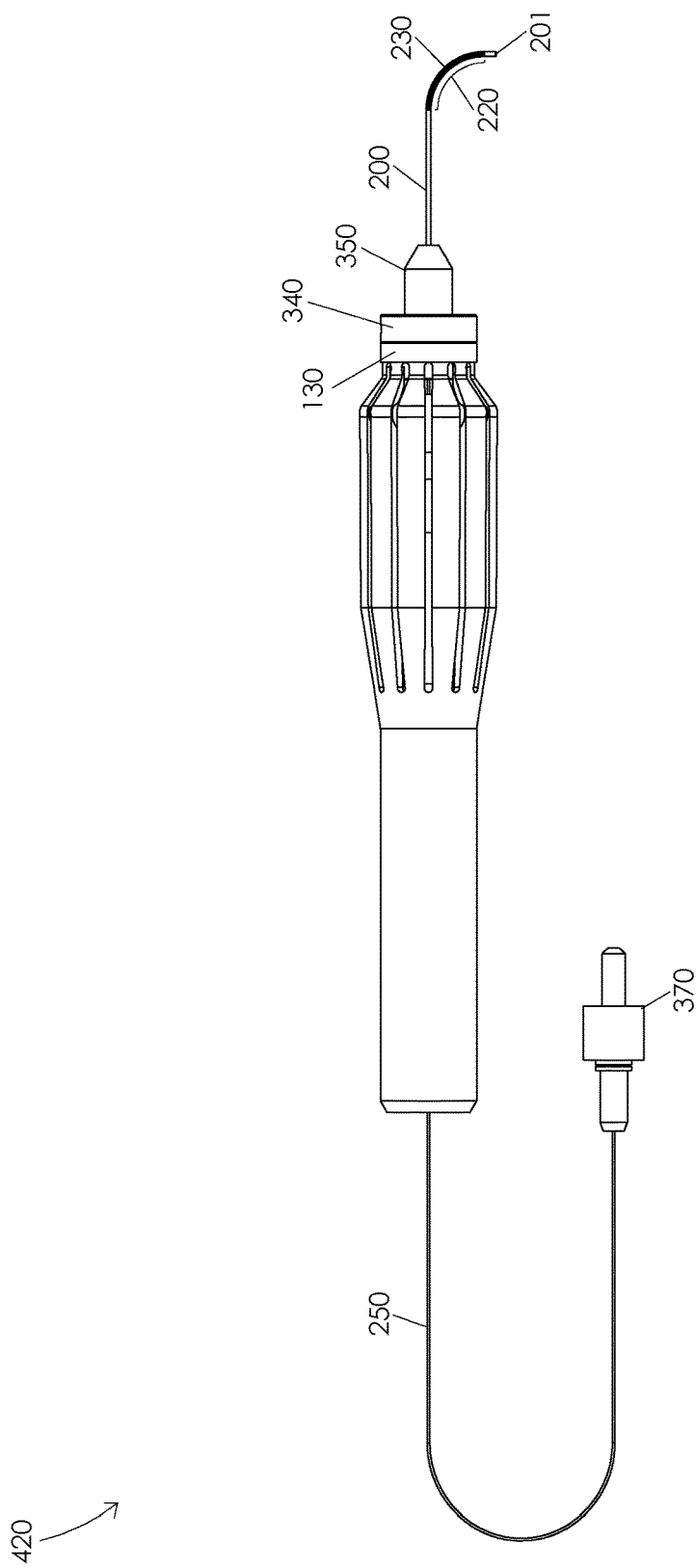

FIG. 4C illustrates an optic fiber in a second curved position 420. In one or more embodiments, a compression of actuation structure 120 may be configured to gradually curve optic fiber 250 from an optic fiber in a first curved position 410 to an optic fiber in a second curved position 420. Illustratively, a compression of actuation structure 120 may be configured to gradually extend housing tube 200 relative to handle base 110. In one or more embodiments, a gradual extension of housing tube 200 relative to handle base 110 may be configured to cause optic fiber 250 to provide a compressive force to an inner portion of housing tube 200. For example, optic fiber 250 may be configured to provide a compressive force configured to oppose an extension of an inner portion of housing tube 200.

Illustratively, an application of a compressive force to an inner portion of housing tube 200, e.g., by extending housing tube 200 relative to handle base 110, may be configured to compress a first housing tube portion 220 of housing tube 200. For example, optic fiber 250 may be fixed in a position relative to handle base 110 and fixed to an inner portion of housing tube 200. In one or more embodiments, as housing tube 200 is gradually extended relative to handle base 110, optic fiber 250 may be configured to resist an inner portion of housing tube 200 from being extended relative to handle base 110 causing the inner portion of housing tube 200 to gradually be compressed. Illustratively, an application of a compressive force to an inner portion of housing tube 200 may be configured to gradually curve housing tube 200. In one or more embodiments, a gradual curving of housing tube 200 may be configured to gradually curve optic fiber 250 from an optic fiber in a first curved position 410 to an optic fiber in a second curved position 420.

Illustratively, a line tangent to optic fiber distal end 251 may intersect a line tangent to housing tube proximal end 202 at a second angle, e.g., when optic fiber 250 comprises an optic fiber in a second curved position 420. In one or more embodiments, the second angle may comprise any angle greater than the first angle. For example, the second angle may comprise a 90 degree angle.

Figure 4D:
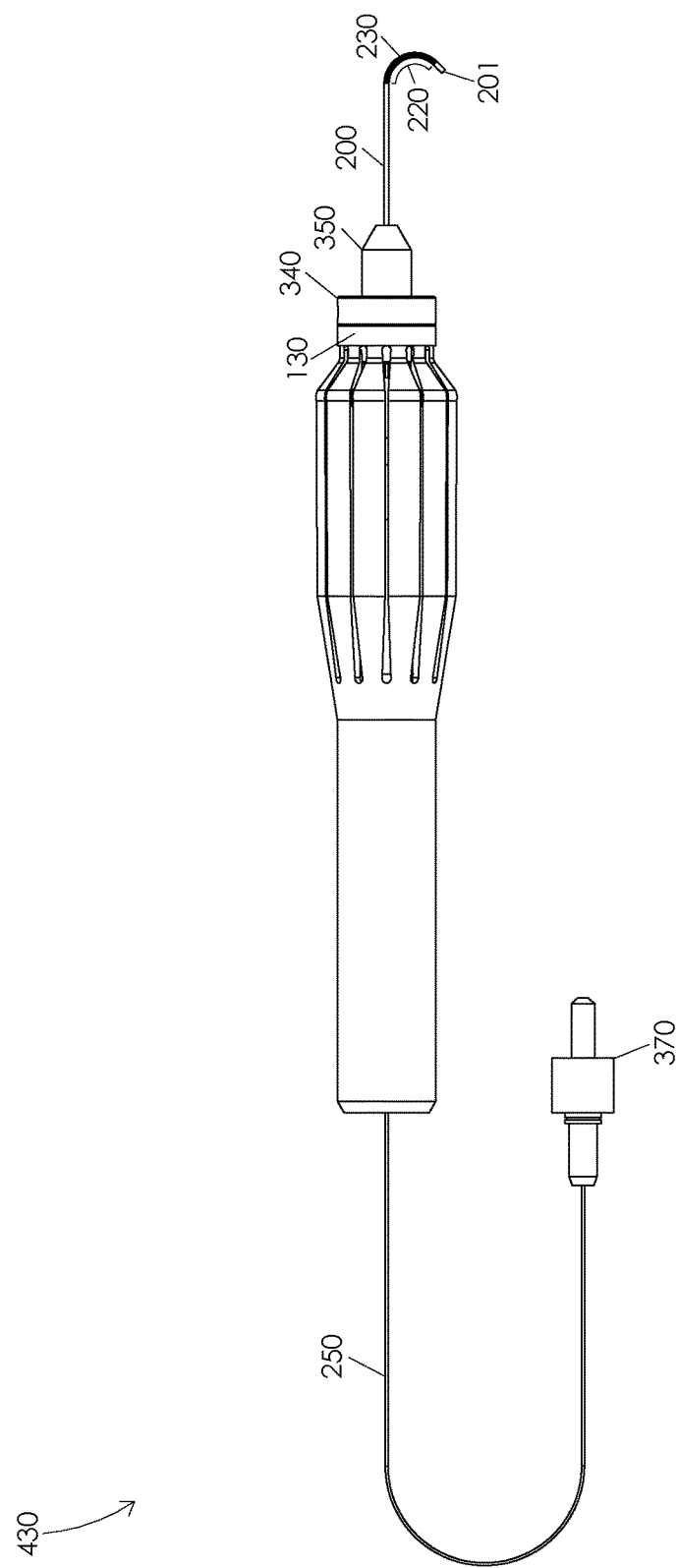

FIG. 4D illustrates an optic fiber in a third curved position 430. In one or more embodiments, a compression of actuation structure 120 may be configured to gradually curve optic fiber 250 from an optic fiber in a second curved position 420 to an optic fiber in a third curved position 430. Illustratively, a compression of actuation structure 120 may be configured to gradually extend housing tube 200 relative to handle base 110. In one or more embodiments, a gradual extension of housing tube 200 relative to handle base 110 may be configured to cause optic fiber 250 to provide a compressive force to an inner portion of housing tube 200. For example, optic fiber 250 may be configured to provide a compressive force configured to oppose an extension of an inner portion of housing tube 200.

Illustratively, an application of a compressive force to an inner portion of housing tube 200, e.g., by extending housing tube 200 relative to handle base 110, may be configured to compress a first housing tube portion 220 of housing tube 200. For example, optic fiber 250 may be fixed in a position relative to handle base 110 and fixed to an inner portion of housing tube 200. In one or more embodiments, as housing tube 200 is gradually extended relative to handle base 110, optic fiber 250 may be configured to resist an inner portion of housing tube 200 from being extended relative to handle base 110 causing the inner portion of housing tube 200 to gradually be compressed. Illustratively, an application of a compressive force to an inner portion of housing tube 200 may be configured to gradually curve housing tube 200. In one or more embodiments, a gradual curving of housing tube 200 may be configured to gradually curve optic fiber 250 from an optic fiber in a second curved position 420 to an optic fiber in a third curved position 430.

Illustratively, a line tangent to optic fiber distal end 251 may intersect a line tangent to housing tube proximal end 202 at a third angle, e.g., when optic fiber 250 comprises an optic fiber in a third curved position 430. In one or more embodiments, the third angle may comprise any angle greater than the second angle. For example, the third angle may comprise a 135 degree angle.

Figure 4E:
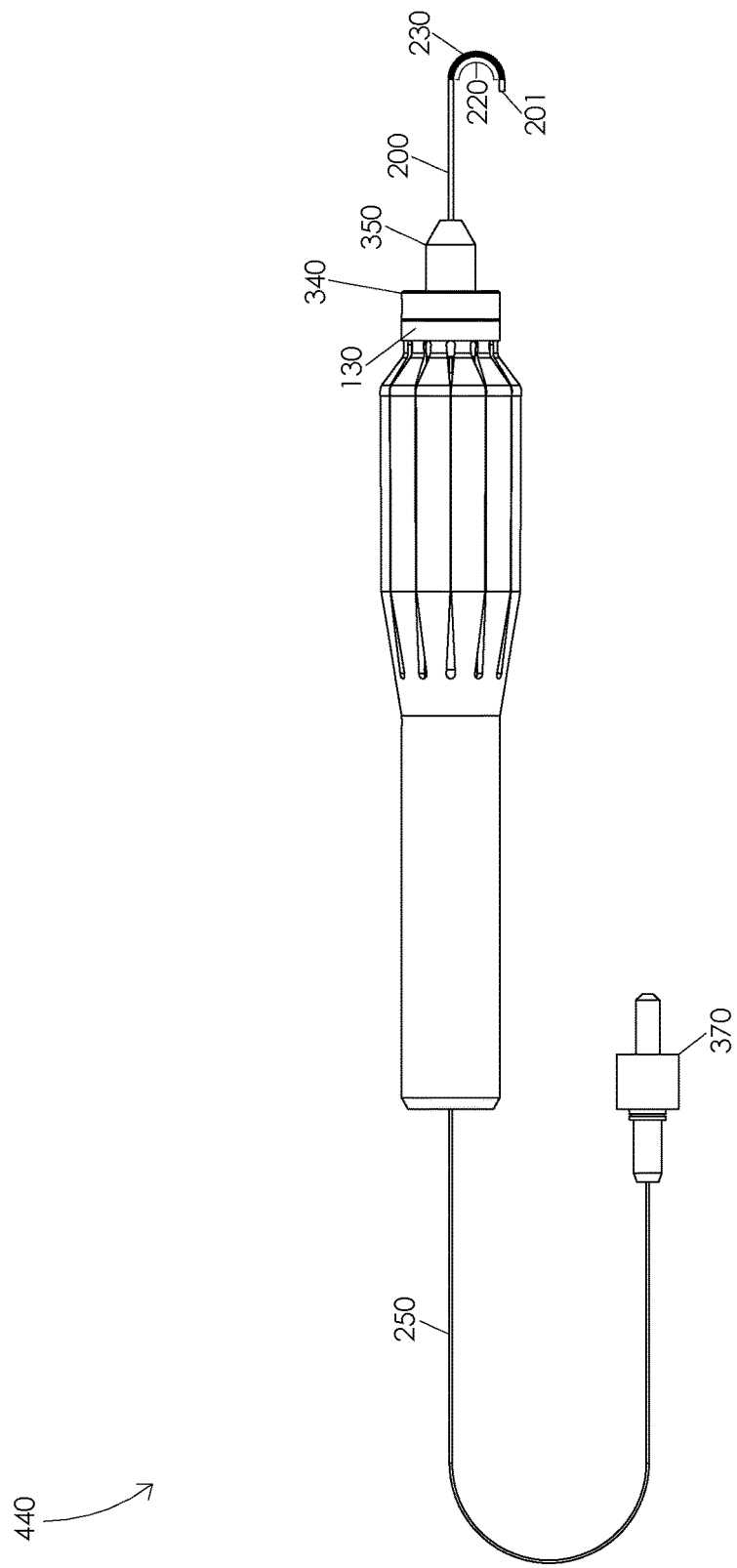

FIG. 4E illustrates an optic fiber in a fourth curved position 440. In one or more embodiments, a compression of actuation structure 120 may be configured to gradually curve optic fiber 250 from an optic fiber in a third curved position 430 to an optic fiber in a fourth curved position 440. Illustratively, a compression of actuation structure 120 may be configured to gradually extend housing tube 200 relative to handle base 110. In one or more embodiments, a gradual extension of housing tube 200 relative to handle base 110 may be configured to cause optic fiber 250 to provide a compressive force to an inner portion of housing tube 200. For example, optic fiber 250 may be configured to provide a compressive force configured to oppose an extension of an inner portion of housing tube 200.

Illustratively, an application of a compressive force to an inner portion of housing tube 200, e.g., by extending housing tube 200 relative to handle base 110, may be configured to compress a first housing tube portion 220 of housing tube 200. For example, optic fiber 250 may be fixed in a position relative to handle base 110 and fixed to an inner portion of housing tube 200. In one or more embodiments, as housing tube 200 is gradually extended relative to handle base 110, optic fiber 250 may be configured to resist an inner portion of housing tube 200 from being extended relative to handle base 110 causing the inner portion of housing tube 200 to gradually be compressed. Illustratively, an application of a compressive force to an inner portion of housing tube 200 may be configured to gradually curve housing tube 200. In one or more embodiments, a gradual curving of housing tube 200 may be configured to gradually curve optic fiber 250 from an optic fiber in a third curved position 430 to an optic fiber in a forth curved position 440. Illustratively, a line tangent to optic fiber distal end 251 may be parallel to a line tangent to housing tube proximal end 202, e.g., when optic fiber 250 comprises an optic fiber in a fourth curved position 440.

In one or more embodiments, one or more properties of a steerable laser probe may be adjusted to attain one or more desired steerable laser probe features. For example, a length that housing tube 200 extends from inner nosecone distal end 351 may be adjusted to vary an amount of compression of actuation structure 120 configured to curve housing tube 200 to a particular curved position. Illustratively, a position of fixation pin 310 or a length of optic fiber 250 extending distally from a position of fixation pin 310 may be adjusted to vary an amount of compression of actuation structure 120 configured to curve housing tube 200 to a particular curved position. In one or more embodiments, a stiffness of first housing tube portion 220 or a stiffness of second housing tube portion 230 may be adjusted to vary an amount of compression of actuation structure 120 configured to curve housing tube 200 to a particular curved position. Illustratively, a material comprising first housing tube portion 220 or a material comprising second housing tube portion 230 may be adjusted to vary an amount of compression of actuation structure 120 configured to curve housing tube 200 to a particular curved position.

In one or more embodiments, a number of apertures in housing tube 200 may be adjusted to vary an amount of compression of actuation structure 120 configured to curve housing tube 200 to a particular curved position. Illustratively, a location of one or more apertures in housing tube 200 may be adjusted to vary an amount of compression of actuation structure 120 configured to curve housing tube 200 to a particular curved position. In one or more embodiments, a geometry of one or more apertures in housing tube 200 may be adjusted to vary an amount of compression of action structure 120 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a distance that inner nosecone 350 extends from outer nosecone distal end 341 may be adjusted to vary an amount of compression of actuation structure 120 configured to curve housing tube 200 to a particular curved position. In one or more embodiments, a geometry of actuation structure 120 may be adjusted to vary an amount of compression of actuation structure 120 configured to curve housing tube 200 to a particular curved position. Illustratively, one or more locations within housing tube 200 wherein optic fiber 250 may be fixed to an inner portion of housing tube 200 may be adjusted to vary an amount of compression of actuation structure 120 configured to curve housing tube 200 to a particular curved position. In one or more embodiments, at least a portion of optic fiber 250 may be enclosed in an optic fiber sleeve configured to, e.g., protect optic fiber 250, vary a stiffness of optic fiber 250, vary an optical property of optic fiber 250, etc. For example, a portion of optic fiber 250 that may be fixed in a position relative to handle 100, e.g., by fixation pin 310, may be enclosed in an optic fiber sleeve configured to, e.g., protect optic fiber 250, facilitate a fixation, etc.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

Figure 5A:
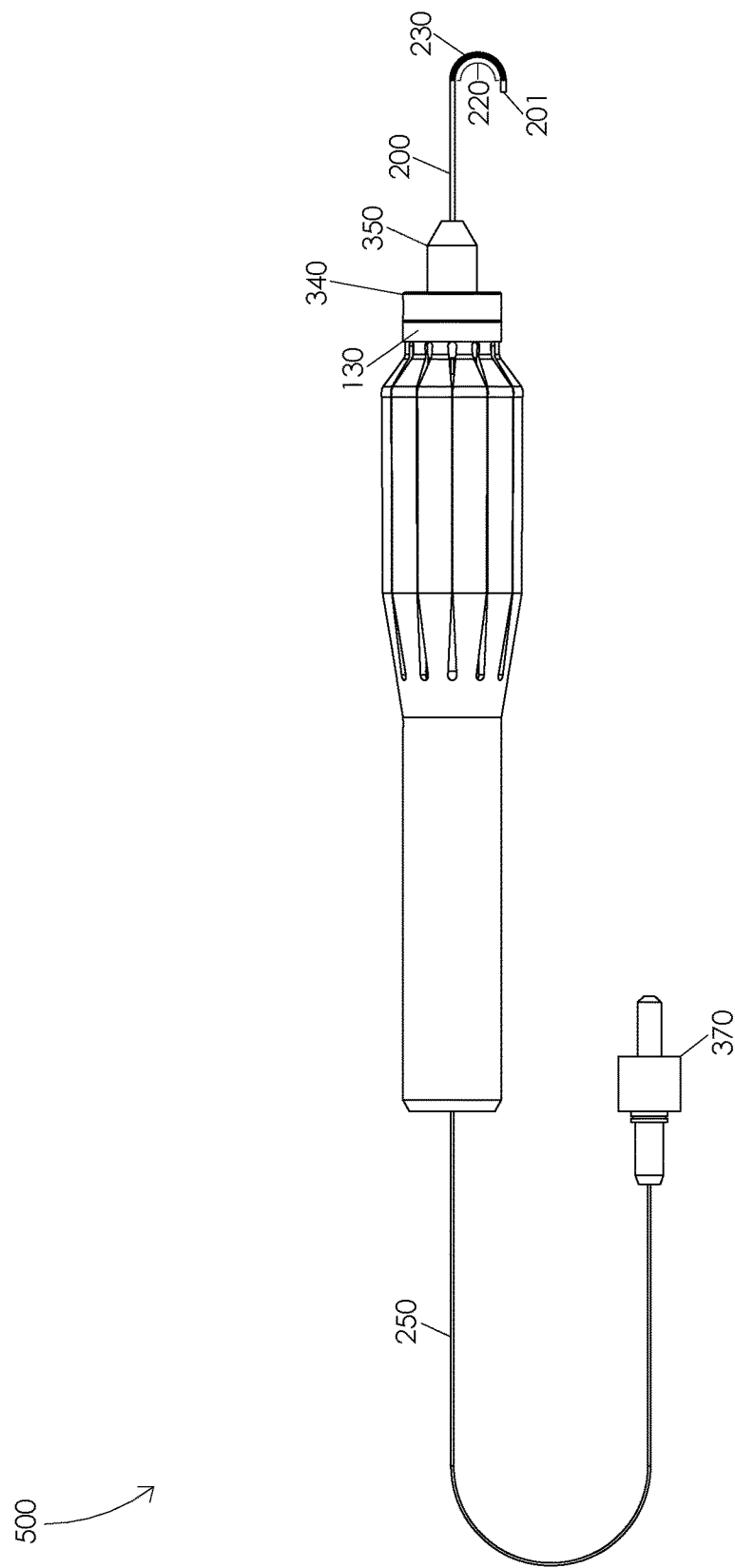
FIGS. 5A, 5B, 5C, 5D, and 5E illustrate a gradual straightening of an optic fiber.

FIGS. 5A, 5B, 5C, 5D, and 5E illustrate a gradual straightening of an optic fiber 250. FIG. 5A illustrates a fully curved optic fiber 500. In one or more embodiments, optic fiber 250 may comprise a fully curved optic fiber 500, e.g., when actuation ring 130 is fully extended relative to handle base 110. Illustratively, optic fiber 250 may comprise a fully curved optic fiber 500, e.g., when actuation structure 120 is fully compressed.

In one or more embodiments, optic fiber 250 may comprise a fully curved optic fiber 500, e.g., when housing tube 200 is fully extended relative to handle base 110. Illustratively, optic fiber 250 may be configured to fully compress a first housing tube portion 220 of housing tube 200, e.g., when optic fiber 250 comprises a fully curved optic fiber 500. Illustratively, a line tangent to optic fiber distal end 251 may be parallel to a line tangent to housing tube proximal end 202, e.g., when optic fiber 250 comprises a fully curved optic fiber 500.

Figure 5B:
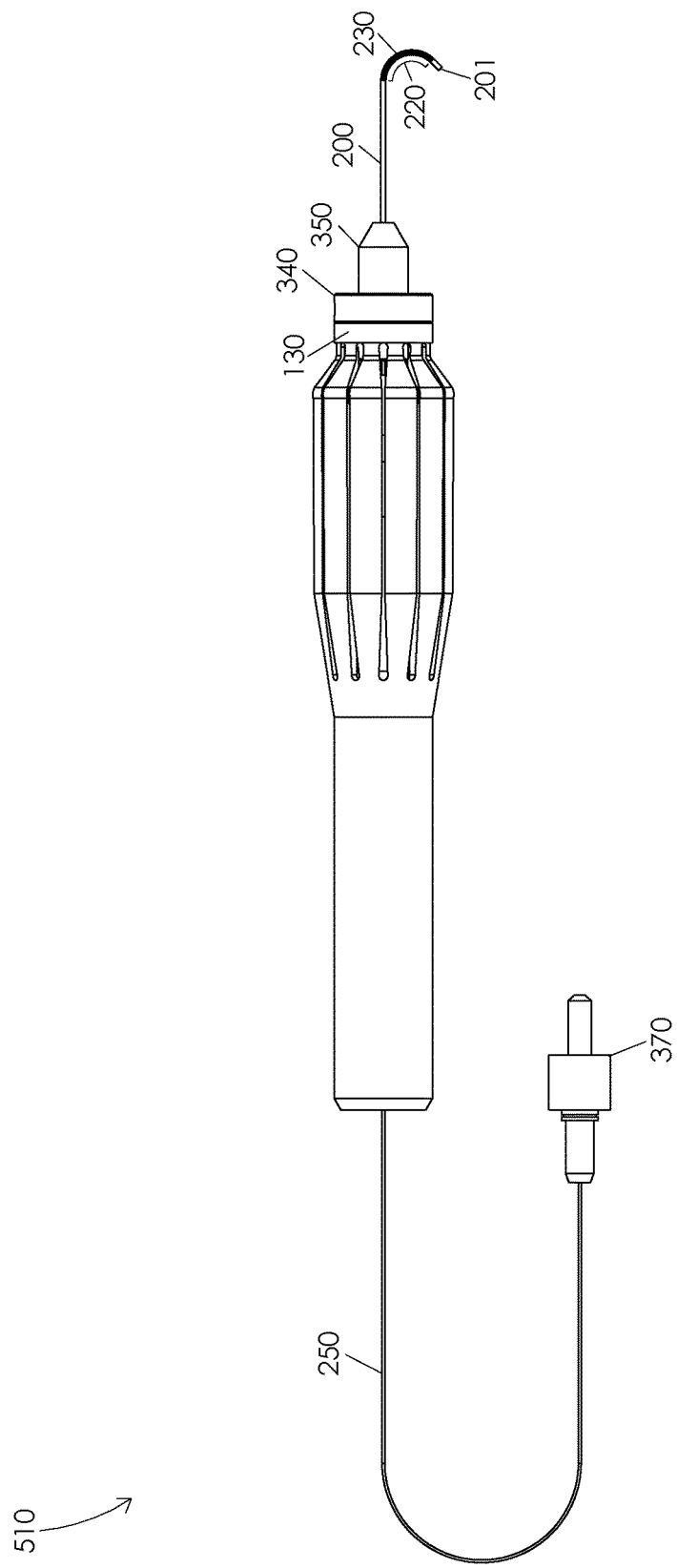

FIG. 5B illustrates an optic fiber in a first partially straightened position 510. In one or more embodiments, a decompression of a fully compressed actuation structure 120 may be configured to gradually straighten optic fiber 250 from a fully curved optic fiber 500 to an optic fiber in a first partially straightened position 510. Illustratively, a decompression of actuation structure 120 may be configured to gradually retract housing tube 200 relative to handle base 110. In one or more embodiments, a gradual retraction of housing tube 200 relative to handle base 110 may be configured to cause optic fiber 250 to reduce a compressive force applied to an inner portion of housing tube 200.

Illustratively, a reduction of a compressive force applied to an inner portion of housing tube 200, e.g., by retracting housing tube 200 relative to handle base 110, may be configured to decompress a first housing tube portion 220 of housing tube 200. For example, optic fiber 250 may be fixed in a position relative to handle base 110 and fixed to an inner portion of housing tube 200. In one or more embodiments, as housing tube 200 is gradually retracted relative to handle base 110, optic fiber 250 may be configured to reduce a compressive force applied to an inner portion of housing tube 200 causing the inner portion of housing tube 200 to gradually be decompressed. Illustratively, a reduction of a compressive force applied to an inner portion of housing tube 200 may be configured to gradually straighten housing tube 200. In one or more embodiments, a gradual straightening of housing tube 200 may be configured to gradually straighten optic fiber 250 from a fully curved optic fiber 500 to an optic fiber in a first partially straightened position 510.

Illustratively, a line tangent to optic fiber distal end 251 may intersect a line tangent to housing tube proximal end 202 at a first partially straightened angle, e.g., when optic fiber 250 comprises an optic fiber in a first partially straightened position 510. In one or more embodiments, the first partially straightened angle may comprise any angle less than 180 degrees. For example, the first partially straightened angle may comprise a 135 degree angle.

Figure 5C:
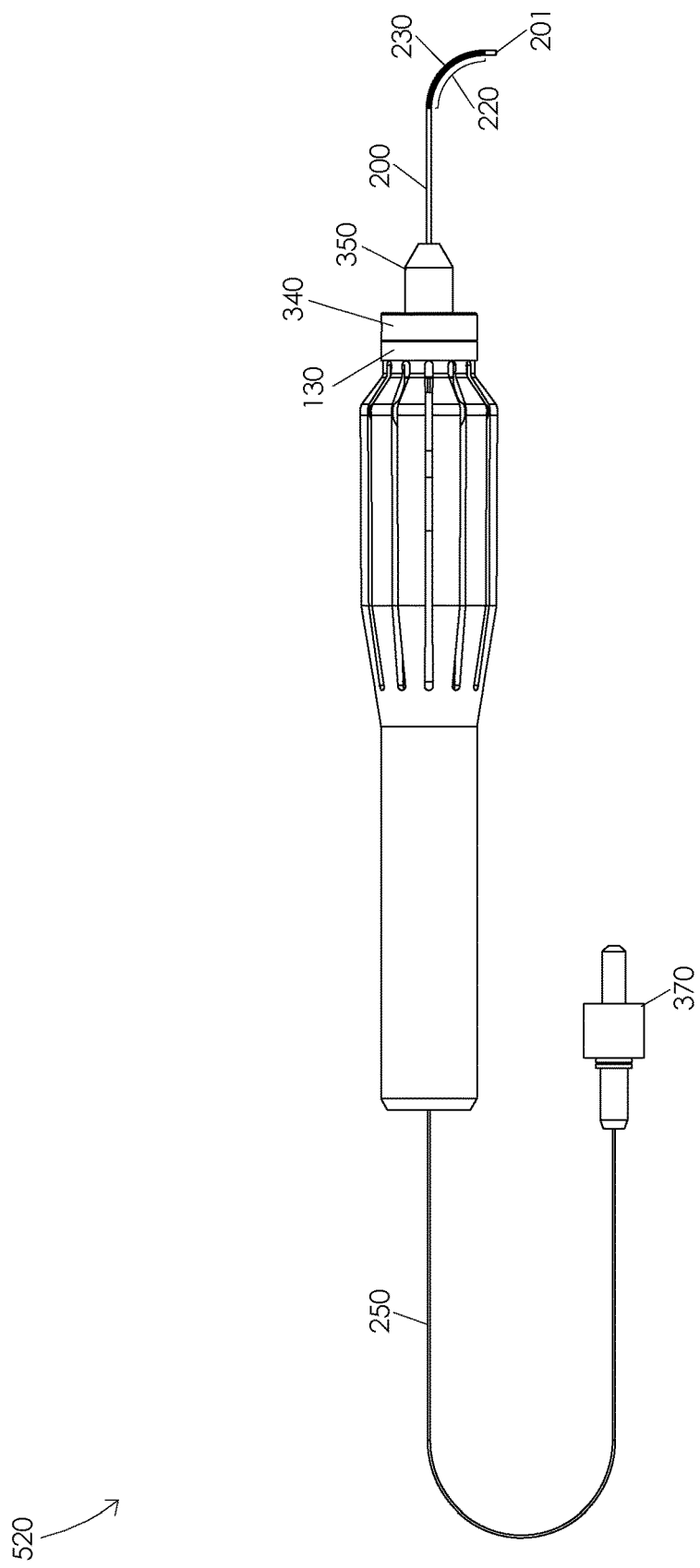

FIG. 5C illustrates an optic fiber in a second partially straightened position 520. In one or more embodiments, a decompression of actuation structure 120 may be configured to gradually straighten optic fiber 250 from an optic fiber in a first partially straightened position 510 to an optic fiber in a second partially straightened position 520. Illustratively, a decompression of actuation structure 120 may be configured to gradually retract housing tube 200 relative to handle base 110. In one or more embodiments, a gradual retraction of housing tube 200 relative to handle base 110 may be configured to cause optic fiber 250 to reduce a compressive force applied to an inner portion of housing tube 200.

Illustratively, a reduction of a compressive force applied to an inner portion of housing tube 200, e.g., by retracting housing tube 200 relative to handle base 110, may be configured to decompress a first housing tube portion 220 of housing tube 200. For example, optic fiber 250 may be fixed in a position relative to handle base 110 and fixed to an inner portion of housing tube 200. In one or more embodiments, as housing tube 200 is gradually retracted relative to handle base 110, optic fiber 250 may be configured to reduce a compressive force applied to an inner portion of housing tube 200 causing the inner portion of housing tube 200 to gradually be decompressed. Illustratively, a reduction of a compressive force applied to an inner portion of housing tube 200 may be configured to gradually straighten housing tube 200. In one or more embodiments, a gradual straightening of housing tube 200 may be configured to gradually straighten optic fiber 250 from an optic fiber in a first partially straightened position 510 to an optic fiber in a second partially straightened position 520.

Illustratively, a line tangent to optic fiber distal end 251 may intersect a line tangent to housing tube proximal end 202 at a second partially straightened angle, e.g., when optic fiber 250 comprises an optic fiber in a second partially straightened position 520. In one or more embodiments, the second partially straightened angle may comprise any angle less than the first partially straightened angle. For example, the second partially straightened angle may comprise a 90 degree angle.

Figure 5D:
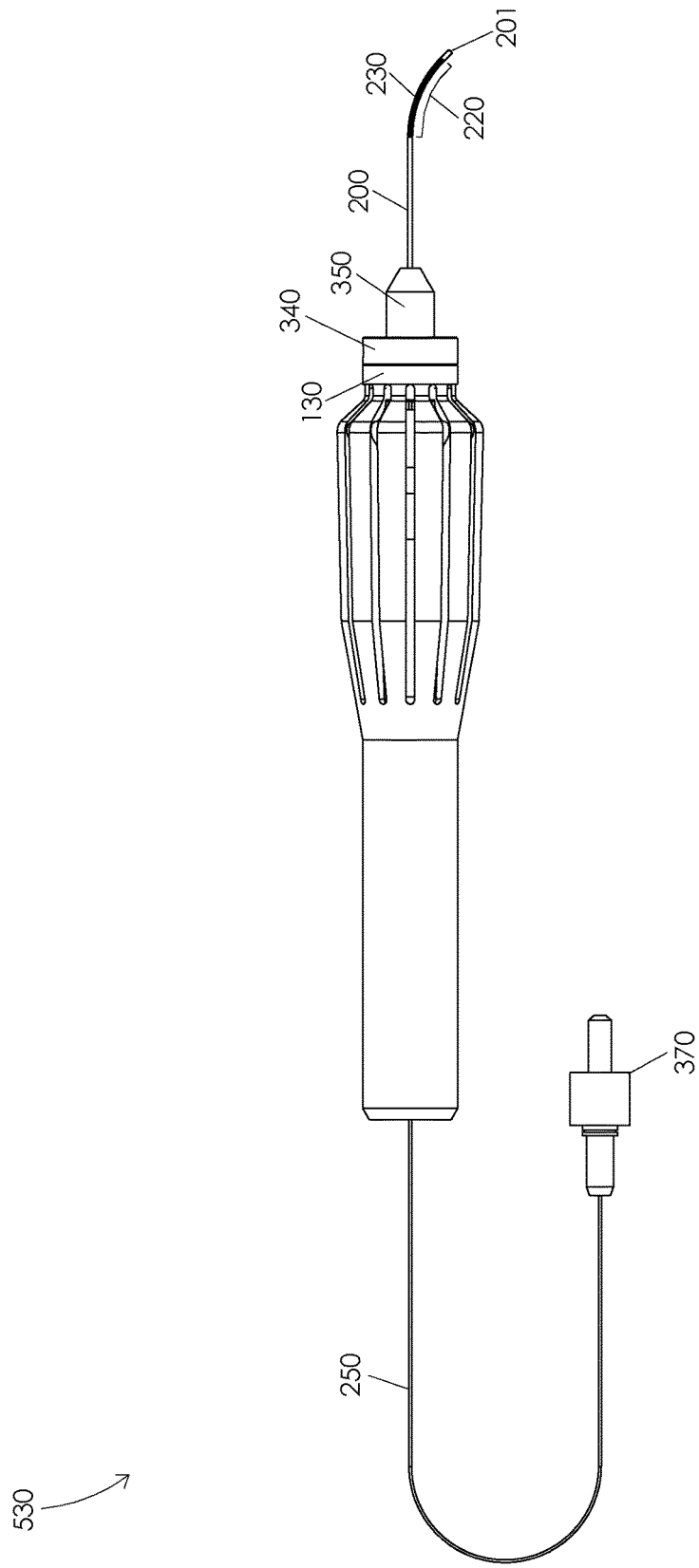

FIG. 5D illustrates an optic fiber in a third partially straightened position 530. In one or more embodiments, a decompression of actuation structure 120 may be configured to gradually straighten optic fiber 250 from an optic fiber in a second partially straightened position 520 to an optic fiber in a third partially straightened position 530. Illustratively, a decompression of actuation structure 120 may be configured to gradually retract housing tube 200 relative to handle base 110. In one or more embodiments, a gradual retraction of housing tube 200 relative to handle base 110 may be configured to cause optic fiber 250 to reduce a compressive force applied to an inner portion of housing tube 200.

Illustratively, a reduction of a compressive force applied to an inner portion of housing tube 200, e.g., by retracting housing tube 200 relative to handle base 110, may be configured to decompress a first housing tube portion 220 of housing tube 200. For example, optic fiber 250 may be fixed in a position relative to handle base 110 and fixed to an inner portion of housing tube 200. In one or more embodiments, as housing tube 200 is gradually retracted relative to handle base 110, optic fiber 250 may be configured to reduce a compressive force applied to an inner portion of housing tube 200 causing the inner portion of housing tube 200 to gradually be decompressed. Illustratively, a reduction of a compressive force applied to an inner portion of housing tube 200 may be configured to gradually straighten housing tube 200. In one or more embodiments, a gradual straightening of housing tube 200 may be configured to gradually straighten optic fiber 250 from an optic fiber in a second partially straightened position 520 to an optic fiber in a third partially straightened position 530.

Illustratively, a line tangent to optic fiber distal end 251 may intersect a line tangent to housing tube proximal end 202 at a third partially straightened angle, e.g., when optic fiber 250 comprises an optic fiber in a third partially straightened position 530. In one or more embodiments, the third partially straightened angle may comprise any angle less than the second partially straightened angle. For example, the third partially straightened angle may comprise a 45 degree angle.

Figure 5E:
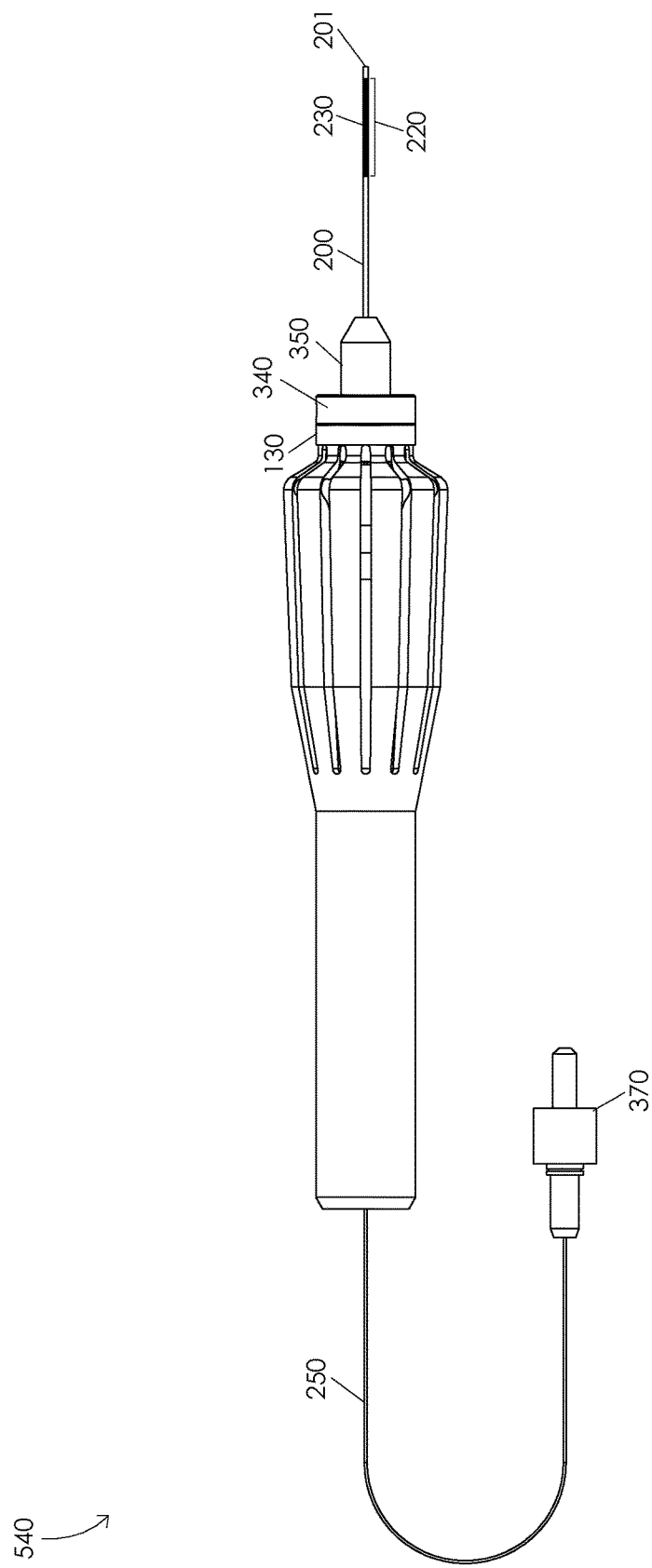

FIG. 5E illustrates an optic fiber in a fully straightened position 540. In one or more embodiments, a decompression of actuation structure 120 may be configured to gradually straighten optic fiber 250 from an optic fiber in a third partially straightened position 530 to an optic fiber in a fully straightened position 540. Illustratively, a decompression of actuation structure 120 may be configured to gradually retract housing tube 200 relative to handle base 110. In one or more embodiments, a gradual retraction of housing tube 200 relative to handle base 110 may be configured to cause optic fiber 250 to reduce a compressive force applied to an inner portion of housing tube 200.

Illustratively, a reduction of a compressive force applied to an inner portion of housing tube 200, e.g., by retracting housing tube 200 relative to handle base 110, may be configured to decompress a first housing tube portion 220 of housing tube 200. For example, optic fiber 250 may be fixed in a position relative to handle base 110 and fixed to an inner portion of housing tube 200. In one or more embodiments, as housing tube 200 is gradually retracted relative to handle base 110, optic fiber 250 may be configured to reduce a compressive force applied to an inner portion of housing tube 200 causing the inner portion of housing tube 200 to gradually be decompressed. Illustratively, a reduction of a compressive force applied to an inner portion of housing tube 200 may be configured to gradually straighten housing tube 200. In one or more embodiments, a gradual straightening of housing tube 200 may be configured to gradually straighten optic fiber 250 from an optic fiber in a third partially straightened position 530 to an optic fiber in a fully straightened position 540. Illustratively, a line tangent to optic fiber distal end 251 may be parallel to a line tangent to housing tube proximal end 202, e.g., when optic fiber 250 comprises an optic fiber in a fully straightened position 540.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient housing tube 200 in an orientation configured to cause a curvature of housing tube 200 within the particular transverse plane of the inner eye and varying an amount of compression of actuation structure 120. Illustratively, a surgeon may aim optic fiber distal end 251 at any target within a particular sagittal plane of the inner eye by, e.g., rotating handle 100 to orient housing tube 200 in an orientation configured to cause a curvature of housing tube 200 within the particular sagittal plane of the inner eye and varying an amount of compression of actuation structure 120. In one or more embodiments, a surgeon may aim optic fiber distal end 251 at any target within a particular frontal plane of the inner eye by, e.g., varying an amount of compression of actuation structure 120 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 6A and 6B are schematic diagrams illustrating a handle 600. FIG. 6A illustrates a top view of handle 600. In one or more embodiments, handle 600 may comprise a handle distal end 601, a handle proximal end 602, a handle base 610, and an actuation structure 620. Illustratively, actuation structure 620 may comprise an actuation structure distal end 621 and an actuation structure proximal end 622. In one or more embodiments, actuation structure 620 may comprise a plurality of actuation arms 625. Illustratively, each actuation arm 625 may comprise at least one extension mechanism 626. In one or more embodiments, actuation structure 620 may comprise a shape memory material configured to project actuation structure distal end 621 a first distance from actuation structure proximal end 622, e.g., when actuation structure 620 is fully decompressed. Illustratively, actuation structure 620 may comprise a shape memory material configured to project actuation structure distal end 621 a second distance from actuation structure proximal end 622, e.g., when actuation structure 620 is fully compressed. In one or more embodiments, the second distance from actuation structure proximal end 622 may be greater than the first distance from actuation structure proximal end 622. Actuation structure 620 may be manufactured from any suitable material, e.g., polymers, metals, metal alloys, etc., or from any combination of suitable materials.

Illustratively, actuation structure 620 may be compressed by an application of a compressive force to actuation structure 620. In one or more embodiments, actuation structure 620 may be compressed by an application of one or more compressive forces located at one or more locations around an outer perimeter of actuation structure 620. Illustratively, the one or more locations may comprise any of a plurality of locations around the outer perimeter of actuation structure 620. For example, a surgeon may compress actuation structure 620 by squeezing actuation structure 620. Illustratively, the surgeon may compress actuation structure 620 by squeezing actuation structure 620 at any particular location of a plurality of locations around an outer perimeter of actuation structure 620. For example, a surgeon may rotate handle 600 and compress actuation structure 620 from any rotational position of a plurality of rotational positions of handle 600.

In one or more embodiments, actuation structure 620 may be compressed by an application of a compressive force to any one or more of the plurality of actuation arms 625. Illustratively, each actuation arm 625 may be configured to actuate independently. In one or more embodiments, each actuation arm 625 may be connected to one or more of the plurality of actuation arms 625 wherein an actuation of a particular actuation arm 625 may be configured to actuate every actuation arm 625 of the plurality of actuation arms 625. Illustratively, one or more actuation arms 625 may be configured to actuate in pairs or groups. For example, an actuation of a first actuation arm 625 may be configured to actuate a second actuation arm 625.

In one or more embodiments, a compression of actuation structure 620, e.g., due to an application of a compressive force to a particular actuation arm 625, may be configured to actuate the particular actuation arm 625. Illustratively, an actuation of the particular actuation arm 625 may be configured to actuate every actuation arm 625 of the plurality of actuation arms 625. In one or more embodiments, an application of a compressive force to a particular actuation arm 625 may be configured to extend at least one extension mechanism 626 of the particular actuation arm 625. Illustratively, a particular actuation arm 625 may be configured to extend a first length from handle base 610. An extension of an extension mechanism 626 of the particular actuation arm 625, e.g., due to an application of a compressive force to the particular actuation arm 625, may be configured to extend the particular actuation arm 625 a second length from handle base 610. Illustratively, the second length from handle base 610 may be greater than the first length from handle base 610.

In one or more embodiments, handle 600 may comprise an actuation ring 630 fixed to actuation structure distal end 621. Illustratively, a compression of actuation structure 620 may be configured to gradually extend actuation ring 630 from handle base 610. For example, actuation ring 630 may be configured to extend a first distance from actuation structure proximal end 622, e.g., when actuation structure 620 is fully decompressed. Actuation ring 630 may be configured to extend a second distance from actuation structure proximal end 622, e.g., due to a compression of actuation structure 620. Illustratively, the second distance from actuation structure proximal end 622 may be greater than the first distance from actuation structure proximal end 622.

FIG. 6B illustrates a cross-sectional view of handle 600. In one or more embodiments, handle 600 may comprise an inner bore 640, an inner bore proximal taper 650, a piston tube housing 660, and a fixation pin housing 670. Handle 600 may be manufactured from any suitable material, e.g., polymers, metals, metal alloys, etc., or from any combination of suitable materials.

Figure 7C:
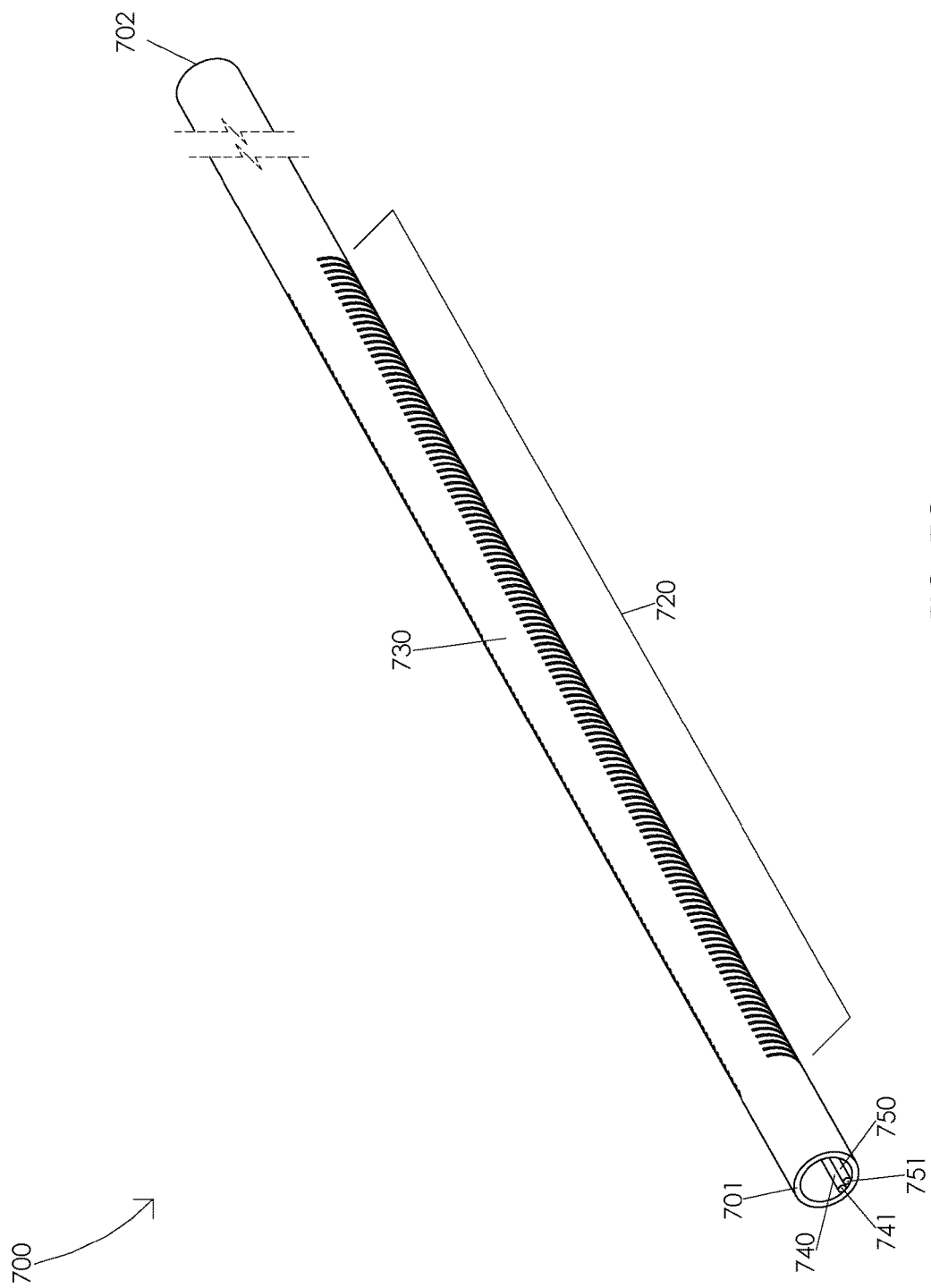

FIGS. 7A, 7B, and 7C are schematic diagrams illustrating a housing tube 700. In one or more embodiments, housing tube 700 may comprise a housing tube distal end 701 and a housing tube proximal end 702. Housing tube 700 may be manufactured from any suitable material, e.g., polymers, metals, metal alloys, etc., or from any combination of suitable materials. FIG. 7A illustrates a housing tube 700 oriented to illustrate a first housing tube portion 720. Illustratively, first housing tube portion 720 may have a first stiffness. FIG. 7B illustrates a housing tube 700 oriented to illustrate a second housing tube portion 730. Illustratively, second housing tube portion 730 may have a second stiffness. In one or more embodiments, the second stiffness may be greater than the first stiffness. Illustratively, first housing tube portion 720 may comprise a first material having a first stiffness. In one or more embodiments, second housing tube portion 730 may comprise a second material having a second stiffness. Illustratively, the second stiffness may be greater than the first stiffness.

In one or more embodiments, first housing tube portion 720 may comprise one or more apertures configured to produce a first stiffness of first housing tube portion 720. Illustratively, second housing tube portion 730 may comprise a solid portion of housing tube 700 having a second stiffness. In one or more embodiments, the second stiffness may be greater than the first stiffness. Illustratively, first housing tube portion 720 may comprise one or more apertures configured to produce a first stiffness of first housing tube portion 720. In one or more embodiments, second housing tube portion 730 may comprise one or more apertures configured to produce a second stiffness of second housing tube portion 730. Illustratively, the second stiffness may be greater than the first stiffness.

In one or more embodiments, first housing tube portion 720 may comprise a plurality of slits configured to separate one or more solid portions of housing tube 700. Illustratively, a plurality of slits may be cut, e.g., laser cut, into first housing tube portion 720. In one or more embodiments, first housing tube portion 720 may comprise a plurality of slits configured to minimize a force of friction between housing tube 700 and a cannula, e.g., as housing tube 700 is inserted into the cannula or as housing tube 700 is extracted from the cannula. For example, each slit of the plurality of slits may comprise one or more arches configured to minimize a force of friction between housing tube 700 and a cannula.

FIG. 7C illustrates an angled view of housing tube 700. Illustratively, an optic fiber 750 may be disposed within housing tube 700. In one or more embodiments, optic fiber 750 may be disposed within housing tube 700 wherein an optic fiber distal end 751 is adjacent to housing tube distal end 701. Illustratively, optic fiber 750 may be disposed within housing tube 700 wherein a portion of optic fiber 750 may be adjacent to a portion of first housing tube portion 720. In one or more embodiments, a portion of optic fiber 750 may be fixed to an inner portion of housing tube 700, e.g., by a biocompatible adhesive or any other suitable means.

Illustratively, a wire 740 may be disposed within housing tube 700. In one or more embodiments, wire 740 may be disposed within housing tube 700 wherein a wire distal end 741 may be adjacent to housing tube distal end 701. Illustratively, wire 740 may be disposed within housing tube 700 wherein a portion of wire 740 may be adjacent to a portion of first housing tube portion 720. In one or more embodiments, a portion of wire 740 may be fixed to an inner portion of housing tube 700, e.g., by a biocompatible adhesive or any other suitable fixation means.

Figure 8:
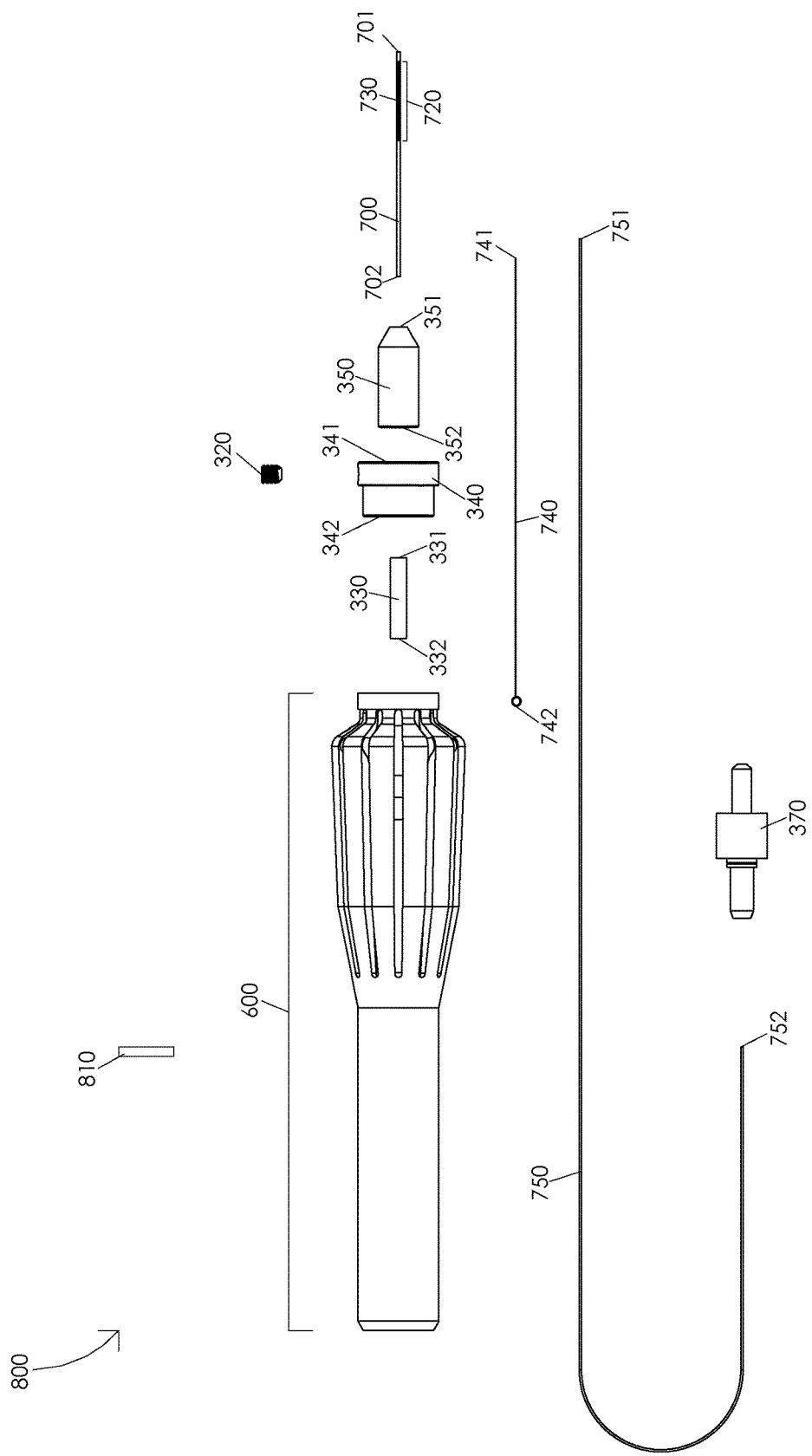
FIG. 8 is a schematic diagram illustrating an exploded view of a steerable laser probe assembly.

FIG. 8 is a schematic diagram illustrating an exploded view of a steerable laser probe assembly 800. In one or more embodiments, steerable laser probe assembly 800 may comprise a handle 600, a housing tube 700 having a housing tube distal end 701 and a housing tube proximal end 702, a wire 740 having a wire distal end 741 and a wire proximal loop 742, an optic fiber 750 having an optic fiber distal end 751 and an optic fiber proximal end 752, a fixation pin 810, a fixation mechanism 320, a piston tube 330 having a piston tube distal end 331 and a piston tube proximal end 332, an outer nosecone 340 having an outer nosecone distal end 341 and an outer nosecone proximal end 342, an inner nosecone 350 having an inner nosecone distal end 351 and an inner nosecone proximal end 352, and a light source interface 370. Illustratively, light source interface 370 may be configured to interface with optic fiber proximal end 752. In one or more embodiments, light source interface 370 may comprise a standard light source connecter, e.g., an SMA connector.

Illustratively, piston tube distal end 331 may be fixed to inner nosecone proximal end 352; housing tube proximal end 702 may be fixed to inner nosecone distal end 351; and outer nosecone 340 may be fixed to actuation structure 620, e.g., outer nosecone proximal end 342 may be fixed to actuation ring 630. In one or more embodiments, fixation mechanism 320 may be configured to attach outer nosecone 340 and inner nosecone 350, e.g., outer nosecone distal end 341 may be fixed to inner nosecone proximal end 352. Illustratively, fixation mechanism 320 may comprise a set screw configured to firmly attach outer nosecone 340 and inner nosecone 350. In one or more embodiments, fixation mechanism 320 may comprise an adhesive material configured to attach outer nosecone 340 and inner nosecone 350, or fixation mechanism 320 may comprise one or more magnets configured to attach outer nosecone 340 and inner nosecone 350. Piston tube 330, outer nosecone 340, and inner nosecone 350 may be manufactured from any suitable material, e.g., polymers, metals, metal alloys, etc., or from any combination of suitable materials. Illustratively, piston tube 330 and inner nosecone 350 may be manufactured as a unit. In one or more embodiments, outer nosecone 340 and inner nosecone 350 may be manufactured as a unit. For example, piston tube 330, outer nosecone 340, and inner nosecone 350 may be manufactured as a unit.

In one or more embodiments, fixation pin 810 may be disposed within fixation pin housing 670. Illustratively, wire 740 may be disposed within housing tube 700, inner nosecone 350, outer nosecone 340, piston tube 330, piston tube housing 660, inner bore 640, and fixation pin housing 670. In one or more embodiments, fixation pin 810 may be configured to fix wire 740 in a position relative to handle 600, e.g., at fixation pin housing 670. For example, fixation pin 810 may be disposed within wire proximal loop 742, e.g., to fix wire 740 in a position relative to handle 600. Illustratively, wire 740 may be disposed within housing tube 700 wherein wire distal end 741 may be adjacent to housing tube distal end 701. In one or more embodiments, wire 740 may be disposed within housing tube 700 wherein wire 740 may be adjacent to a first housing tube portion 720. Illustratively, a portion of wire 740 may be fixed to an inner portion of housing tube 700, e.g., by a biocompatible adhesive or any other suitable fixation means.

In one or more embodiments, optic fiber 750 may be disposed within inner bore 640, fixation pin housing 670, piston tube housing 660, piston tube 330, outer nosecone 340, inner nosecone 350, and housing tube 700. Illustratively, optic fiber 750 may be disposed within housing tube 700 wherein optic fiber distal end 751 may be adjacent to housing tube distal end 701. In one or more embodiments, optic fiber 750 may be disposed within housing tube 700 wherein optic fiber 750 may be adjacent to a first housing tube portion 720. Illustratively, a portion of optic fiber 750 may be fixed to an inner portion of housing tube 700, e.g., by a biocompatible adhesive or any other suitable fixation means.

In one or more embodiments, a compression of actuation structure 620 may be configured to gradually extend actuation ring 630, piston tube 330, outer nosecone 340, inner nosecone 350, and housing tube 700 relative to handle base 610. Illustratively, wire 740 may be both fixed in a position relative to handle base 610, e.g., by fixation pin 810, and fixed to an inner portion of housing tube 700. In one or more embodiments, as housing tube 700 is extended relative to handle base 610, e.g., due to a compression of actuation structure 620, wire 740 may be configured to resist a portion of housing tube 700, e.g., a first housing tube portion 720, from extending relative to handle base 610. Illustratively, as housing tube 700 is gradually extended relative to handle base 610, wire 740 may be configured to gradually compress a first housing tube portion 720 of housing tube 700 causing housing tube 700 to gradually curve. In one or more embodiments, a gradual curving of housing tube 700 may be configured to gradually curve optic fiber 750.

Illustratively, a decompression of actuation structure 620 may be configured to gradually retract actuation ring 630, piston tube 330, outer nosecone 340, inner nosecone 350, and housing tube 700 relative to handle base 610. In one or more embodiments, as housing tube 700 is gradually retracted relative to handle base 610, wire 740 may be configured to gradually decompress a first housing tube portion 720 of housing tube 700 causing housing tube 700 to gradually straighten. For example, a decompression of actuation structure 620 may be configured to reduce a compressive force applied, e.g., by wire 740, to an inner portion of housing tube 700 causing housing tube 700 to gradually straighten. Illustratively, a gradual straightening of housing tube 700 may be configured to gradually straighten optic fiber 750.

In one or more embodiments, first housing tube portion 720 may comprise a one or more apertures in housing tube 700. Illustratively, a first solid portion of first housing tube portion 720 may be separated, e.g., by an aperture in housing tube 700, from a second solid portion of first housing tube portion 720. In one or more embodiments, a first solid portion of first housing tube portion 720 may be separated from a second solid portion of first housing tube portion 720 by a separation distance. Illustratively, a compression of actuation structure 620 may be configured to reduce the separation distance between the first solid portion of first housing tube portion 720 and the second solid portion of first housing tube portion 720. In one or more embodiments, a decompression of actuation structure 620 may be configured to increase the separation distance between the first solid portion of first housing tube portion 720 and the second solid portion of first housing tube portion 720.

Figure 9A:
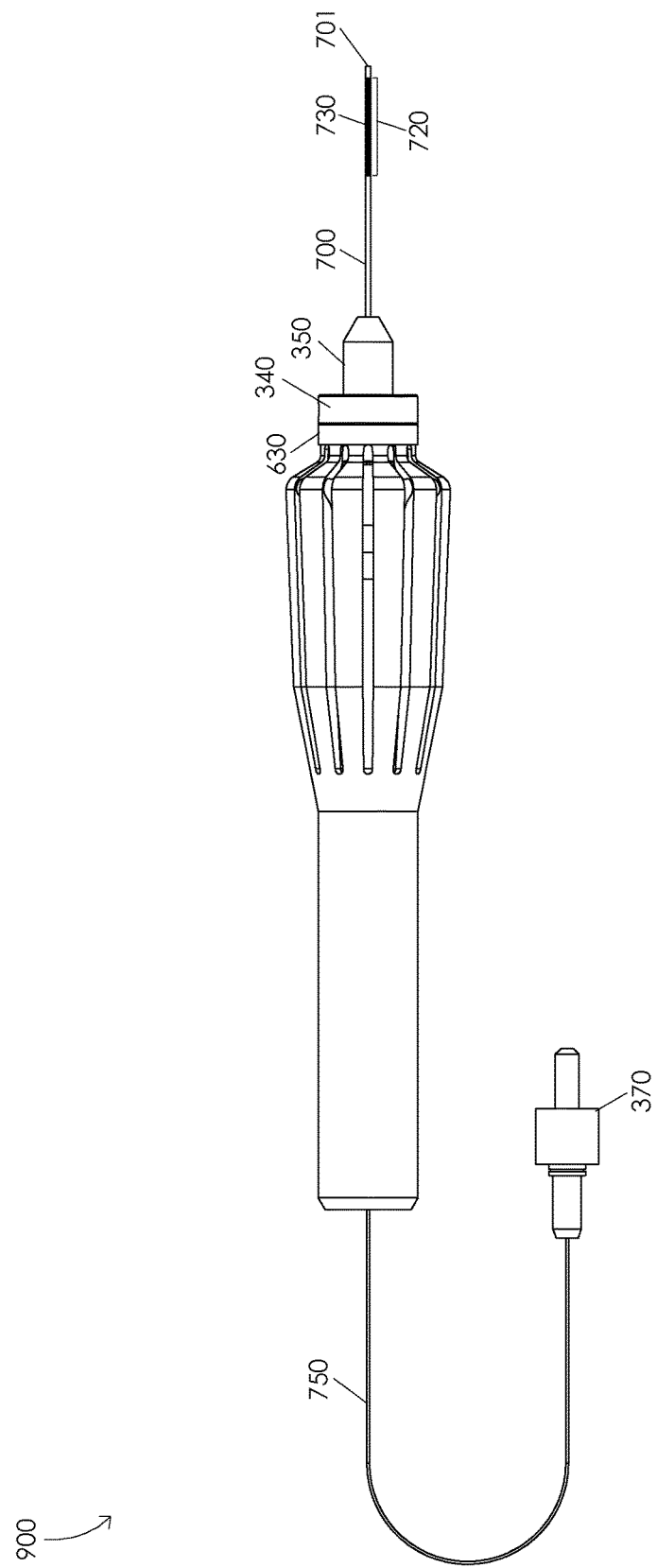
FIGS. 9A, 9B, 9C, 9D, and 9E illustrate a gradual curving of an optic fiber.

FIGS. 9A, 9B, 9C, 9D, and 9E illustrate a gradual curving of an optic fiber 750. FIG. 9A illustrates a straight optic fiber 900. In one or more embodiments, optic fiber 750 may comprise a straight optic fiber 900, e.g., when actuation ring 630 is fully retracted relative to handle base 610. Illustratively, optic fiber 750 may comprise a straight optic fiber 900, e.g., when actuation structure 620 is fully decompressed. In one or more embodiments, optic fiber 750 may comprise a straight optic fiber 900, e.g., when housing tube 700 is fully retracted relative to handle base 610. Illustratively, a line tangent to optic fiber distal end 751 may be parallel to a line tangent to housing tube proximal end 702, e.g., when optic fiber 750 comprises a straight optic fiber 900.

Figure 9B:
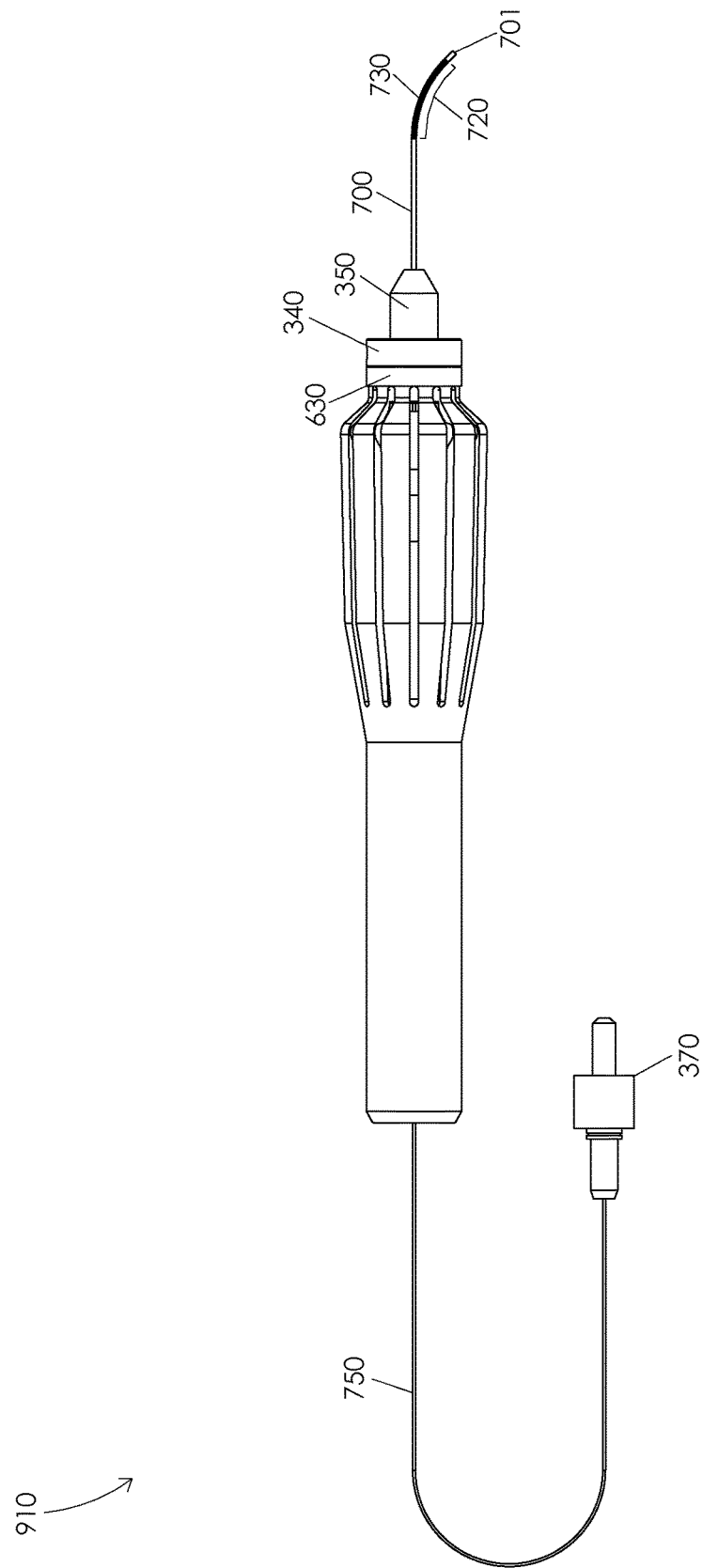

FIG. 9B illustrates an optic fiber in a first curved position 910. In one or more embodiments, a compression of a fully decompressed actuation structure 620 may be configured to gradually curve optic fiber 750 from a straight optic fiber 900 to an optic fiber in a first curved position 910. Illustratively, a compression of actuation structure 620 may be configured to gradually extend housing tube 700 relative to handle base 610 and wire 740. In one or more embodiments, a gradual extension of housing tube 700 relative to handle base 610 may be configured to cause wire 740 to provide a compressive force to an inner portion of housing tube 700. For example, wire 740 may be configured to provide a compressive force configured to oppose an extension of an inner portion of housing tube 700.

Illustratively, an application of a compressive force to an inner portion of housing tube 700, e.g., by extending housing tube 700 relative to handle base 610, may be configured to compress a first housing tube portion 720 of housing tube 700. For example, wire 740 may be fixed in a position relative to handle base 610 and fixed to an inner portion of housing tube 700. In one or more embodiments, as housing tube 700 is gradually extended relative to handle base 610, wire 740 may be configured to resist an inner portion of housing tube 700 from being extended relative to handle base 610 causing the inner portion of housing tube 700 to gradually be compressed. Illustratively, an application of a compressive force to an inner portion of housing tube 700 may be configured to gradually curve housing tube 700. In one or more embodiments, a gradual curving of housing tube 700 may be configured to gradually curve optic fiber 750 from a straight optic fiber 900 to an optic fiber in a first curved position 910.

Illustratively, a line tangent to optic fiber distal end 751 may intersect a line tangent to housing tube proximal end 702 at a first angle, e.g., when optic fiber 750 comprises an optic fiber in a first curved position 910. In one or more embodiments, the first angle may comprise any angle greater than zero degrees. For example, the first angle may comprise a 45 degree angle.

Figure 9C:
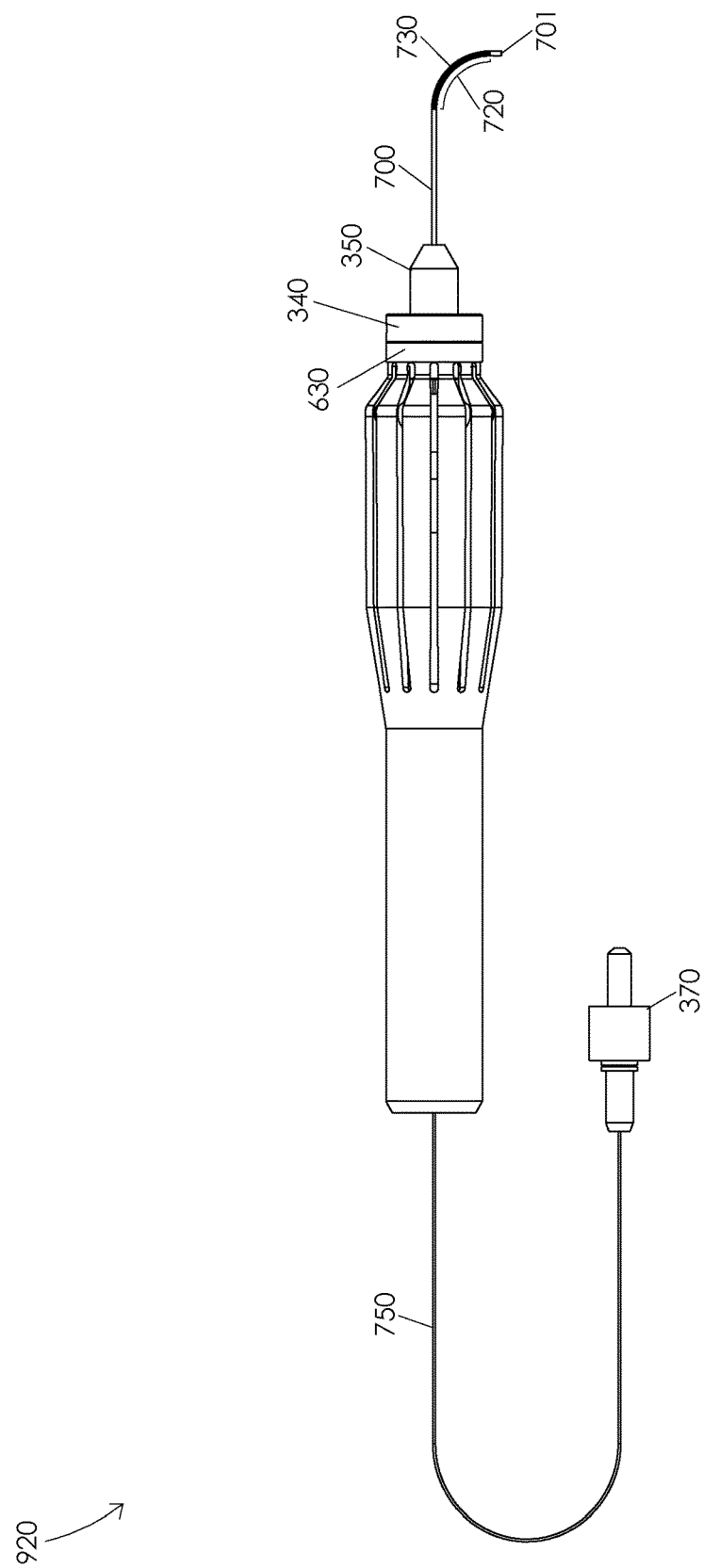

FIG. 9C illustrates an optic fiber in a second curved position 920. In one or more embodiments, a compression of actuation structure 620 may be configured to gradually curve optic fiber 750 from an optic fiber in a first curved position 910 to an optic fiber in a second curved position 920. Illustratively, a compression of actuation structure 620 may be configured to gradually extend housing tube 700 relative to handle base 610 and wire 740. In one or more embodiments, a gradual extension of housing tube 700 relative to handle base 610 may be configured to cause wire 740 to provide a compressive force to an inner portion of housing tube 700. For example, wire 740 may be configured to provide a compressive force configured to oppose an extension of an inner portion of housing tube 700.

Illustratively, an application of a compressive force to an inner portion of housing tube 700, e.g., by extending housing tube 700 relative to handle base 610, may be configured to compress a first housing tube portion 720 of housing tube 700. For example, wire 740 may be fixed in a position relative to handle base 610 and fixed to an inner portion of housing tube 700. In one or more embodiments, as housing tube 700 is gradually extended relative to handle base 610, wire 740 may be configured to resist an inner portion of housing tube 700 from being extended relative to handle base 610 causing the inner portion of housing tube 700 to gradually be compressed. Illustratively, an application of a compressive force to an inner portion of housing tube 700 may be configured to gradually curve housing tube 700. In one or more embodiments, a gradual curving of housing tube 700 may be configured to gradually curve optic fiber 750 from an optic fiber in a first curved position 910 to an optic fiber in a second curved position 920.

Illustratively, a line tangent to optic fiber distal end 751 may intersect a line tangent to housing tube proximal end 702 at a second angle, e.g., when optic fiber 750 comprises an optic fiber in a second curved position 920. In one or more embodiments, the second angle may comprise any angle greater than the first angle. For example, the second angle may comprise a 90 degree angle.

Figure 9D:
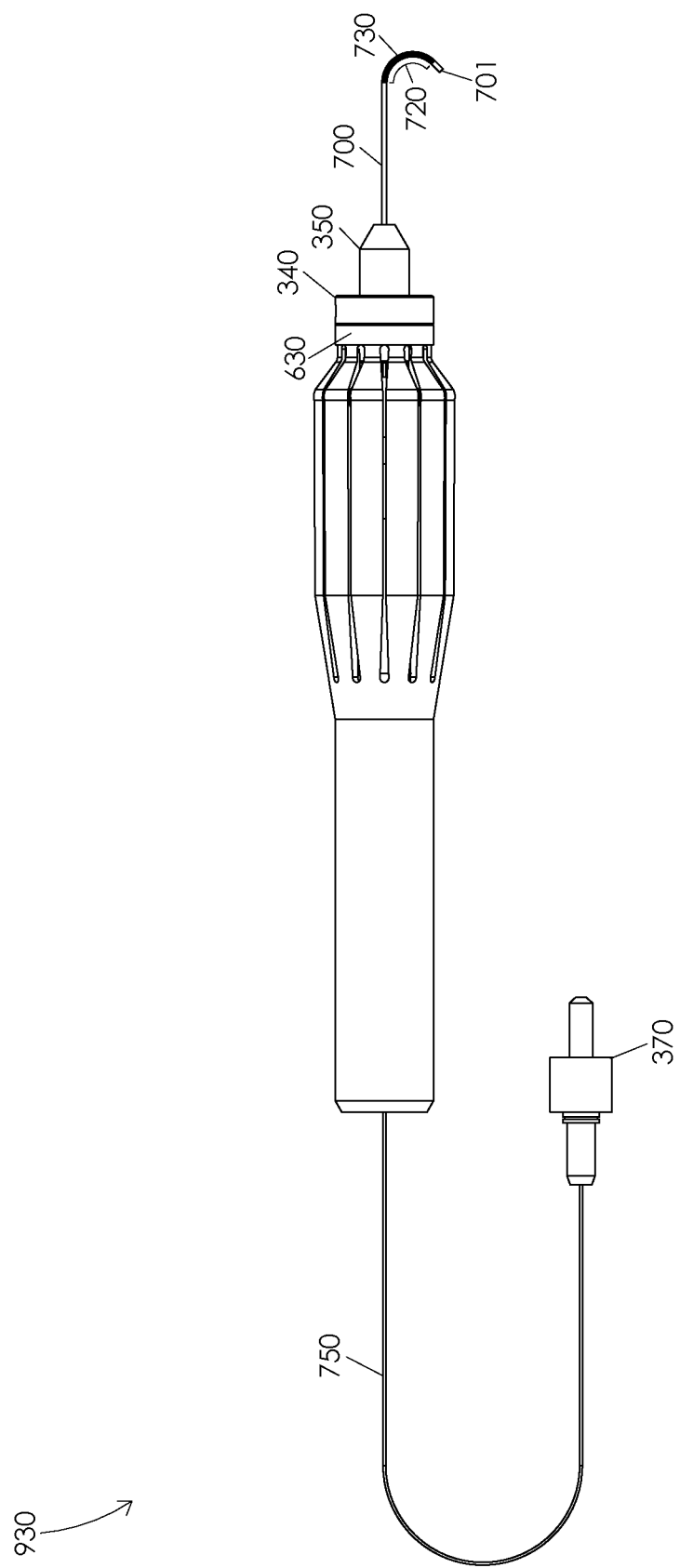

FIG. 9D illustrates an optic fiber in a third curved position 930. In one or more embodiments, a compression of actuation structure 620 may be configured to gradually curve optic fiber 750 from an optic fiber in a second curved position 920 to an optic fiber in a third curved position 930. Illustratively, a compression of actuation structure 620 may be configured to gradually extend housing tube 700 relative to handle base 610 and wire 740. In one or more embodiments, a gradual extension of housing tube 700 relative to handle base 610 may be configured to cause wire 740 to provide a compressive force to an inner portion of housing tube 700. For example, wire 750 may be configured to provide a compressive force configured to oppose an extension of an inner portion of housing tube 700.

Illustratively, an application of a compressive force to an inner portion of housing tube 700, e.g., by extending housing tube 700 relative to handle base 610, may be configured to compress a first housing tube portion 720 of housing tube 700. For example, wire 740 may be fixed in a position relative to handle base 610 and fixed to an inner portion of housing tube 700. In one or more embodiments, as housing tube 700 is gradually extended relative to handle base 610, wire 740 may be configured to resist an inner portion of housing tube 700 from being extended relative to handle base 610 causing the inner portion of housing tube 700 to gradually be compressed. Illustratively, an application of a compressive force to an inner portion of housing tube 700 may be configured to gradually curve housing tube 700. In one or more embodiments, a gradual curving of housing tube 700 may be configured to gradually curve optic fiber 750 from an optic fiber in a second curved position 920 to an optic fiber in a third curved position 930.

Illustratively, a line tangent to optic fiber distal end 751 may intersect a line tangent to housing tube proximal end 702 at a third angle, e.g., when optic fiber 750 comprises an optic fiber in a third curved position 930. In one or more embodiments, the third angle may comprise any angle greater than the second angle. For example, the third angle may comprise a 135 degree angle.

Figure 9E:
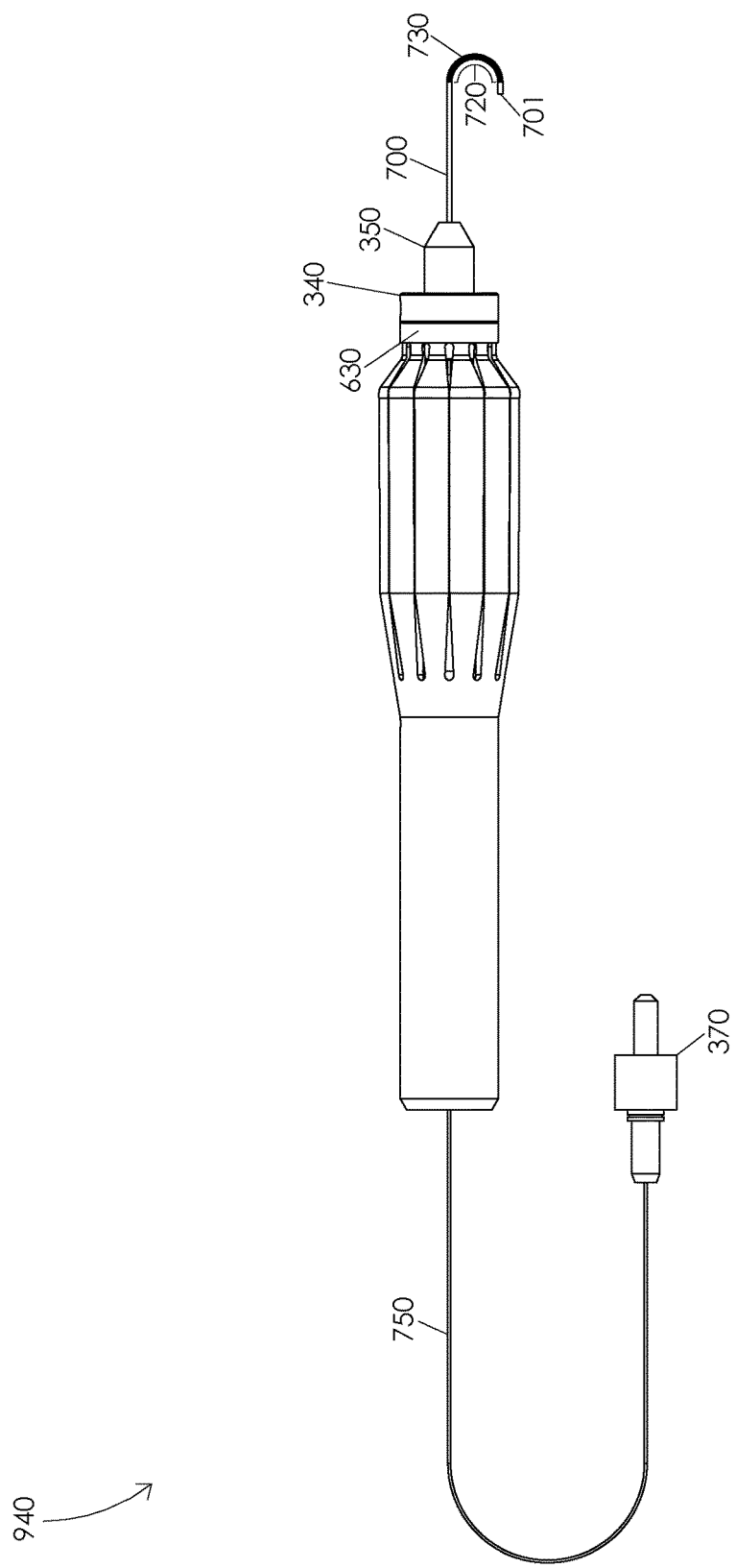

FIG. 9E illustrates an optic fiber in a fourth curved position 940. In one or more embodiments, a compression of actuation structure 620 may be configured to gradually curve optic fiber 750 from an optic fiber in a third curved position 930 to an optic fiber in a fourth curved position 940. Illustratively, a compression of actuation structure 620 may be configured to gradually extend housing tube 700 relative to handle base 610 and wire 740. In one or more embodiments, a gradual extension of housing tube 700 relative to handle base 610 may be configured to cause wire 740 to provide a compressive force to an inner portion of housing tube 700. For example, wire 740 may be configured to provide a compressive force configured to oppose an extension of an inner portion of housing tube 700.

Illustratively, an application of a compressive force to an inner portion of housing tube 700, e.g., by extending housing tube 700 relative to handle base 610, may be configured to compress a first housing tube portion 720 of housing tube 700. For example, wire 740 may be fixed in a position relative to handle base 610 and fixed to an inner portion of housing tube 700. In one or more embodiments, as housing tube 700 is gradually extended relative to handle base 610, wire 740 may be configured to resist an inner portion of housing tube 700 from being extended relative to handle base 610 causing the inner portion of housing tube 700 to gradually be compressed. Illustratively, an application of a compressive force to an inner portion of housing tube 700 may be configured to gradually curve housing tube 700. In one or more embodiments, a gradual curving of housing tube 700 may be configured to gradually curve optic fiber 750 from an optic fiber in a third curved position 930 to an optic fiber in a forth curved position 940. Illustratively, a line tangent to optic fiber distal end 751 may be parallel to a line tangent to housing tube proximal end 702, e.g., when optic fiber 750 comprises an optic fiber in a fourth curved position 940.

In one or more embodiments, one or more properties of a steerable laser probe may be adjusted to attain one or more desired steerable laser probe features. For example, a length that housing tube 700 extends from inner nosecone distal end 351 may be adjusted to vary an amount of compression of actuation structure 620 configured to curve housing tube 700 to a particular curved position. In one or more embodiments, a portion of wire 740 may be fixed to an outer portion of housing tube 700 wherein a compression of actuation structure 620 may be configured to cause wire 740 to compress a first housing tube portion 720 of housing tube 700. Illustratively, a position of fixation pin 810 or a length of wire 740 extending distally from a position of fixation pin 810 may be adjusted to vary an amount of compression of actuation structure 620 configured to curve housing tube 700 to a particular curved position. In one or more embodiments, a stiffness of first housing tube portion 720 or a stiffness of second housing tube portion 730 may be adjusted to vary an amount of compression of actuation structure 620 configured to curve housing tube 700 to a particular curved position. Illustratively, a material comprising first housing tube portion 720 or a material comprising second housing tube portion 730 may be adjusted to vary an amount of compression of actuation structure 620 configured to curve housing tube 700 to a particular curved position.

In one or more embodiments, a number of apertures in housing tube 700 may be adjusted to vary an amount of compression of actuation structure 620 configured to curve housing tube 700 to a particular curved position. Illustratively, a location of one or more apertures in housing tube 700 may be adjusted to vary an amount of compression of actuation structure 620 configured to curve housing tube 700 to a particular curved position. In one or more embodiments, a geometry of one or more apertures in housing tube 700 may be adjusted to vary an amount of compression of action structure 620 configured to curve housing tube 700 to a particular curved position. Illustratively, a geometry of one or more apertures in housing tube 700 may be uniform, e.g., each aperture of the one or more apertures may have a same geometry. In one or more embodiments, a geometry of one or more apertures in housing tube 700 may be non-uniform, e.g., a first aperture in housing tube 700 may have a first geometry and a second aperture in housing tube 700 may have a second geometry.

Illustratively, a distance that inner nosecone 350 extends from outer nosecone distal end 341 may be adjusted to vary an amount of compression of actuation structure 620 configured to curve housing tube 700 to a particular curved position. In one or more embodiments, a geometry of actuation structure 620 may be adjusted to vary an amount of compression of actuation structure 620 configured to curve housing tube 700 to a particular curved position. Illustratively, one or more locations within housing tube 700 wherein wire 740 may be fixed to an inner portion of housing tube 700 may be adjusted to vary an amount of compression of actuation structure 620 configured to curve housing tube 700 to a particular curved position. In one or more embodiments, at least a portion of optic fiber 750 may be enclosed in an optic fiber sleeve configured to, e.g., protect optic fiber 750, vary a stiffness of optic fiber 750, vary an optical property of optic fiber 750, etc.

Illustratively, a stiffness of first housing tube portion 720 or a stiffness of second housing tube portion 730 may be adjusted to vary a bend radius of housing tube 700. In one or more embodiments, a stiffness of first housing tube portion 720 or a stiffness of second housing tube portion 730 may be adjusted to vary a radius of curvature of housing tube 700, e.g., when housing tube 700 is in a particular curved position. Illustratively, a number of apertures in housing tube 700 may be adjusted to vary a bend radius of housing tube 700. In one or more embodiments, a number of apertures in housing tube 700 may be adjusted to vary a radius of curvature of housing tube 700, e.g., when housing tube 700 is in a particular curved position. Illustratively, a location or a geometry of one or more apertures in housing tube 700 may be adjusted to vary a bend radius of housing tube 700. In one or more embodiments, a location or a geometry of one or more apertures in housing tube 700 may be adjusted to vary a radius of curvature of housing tube 700, e.g., when housing tube 700 is in a particular curved position.

Figure 10A:
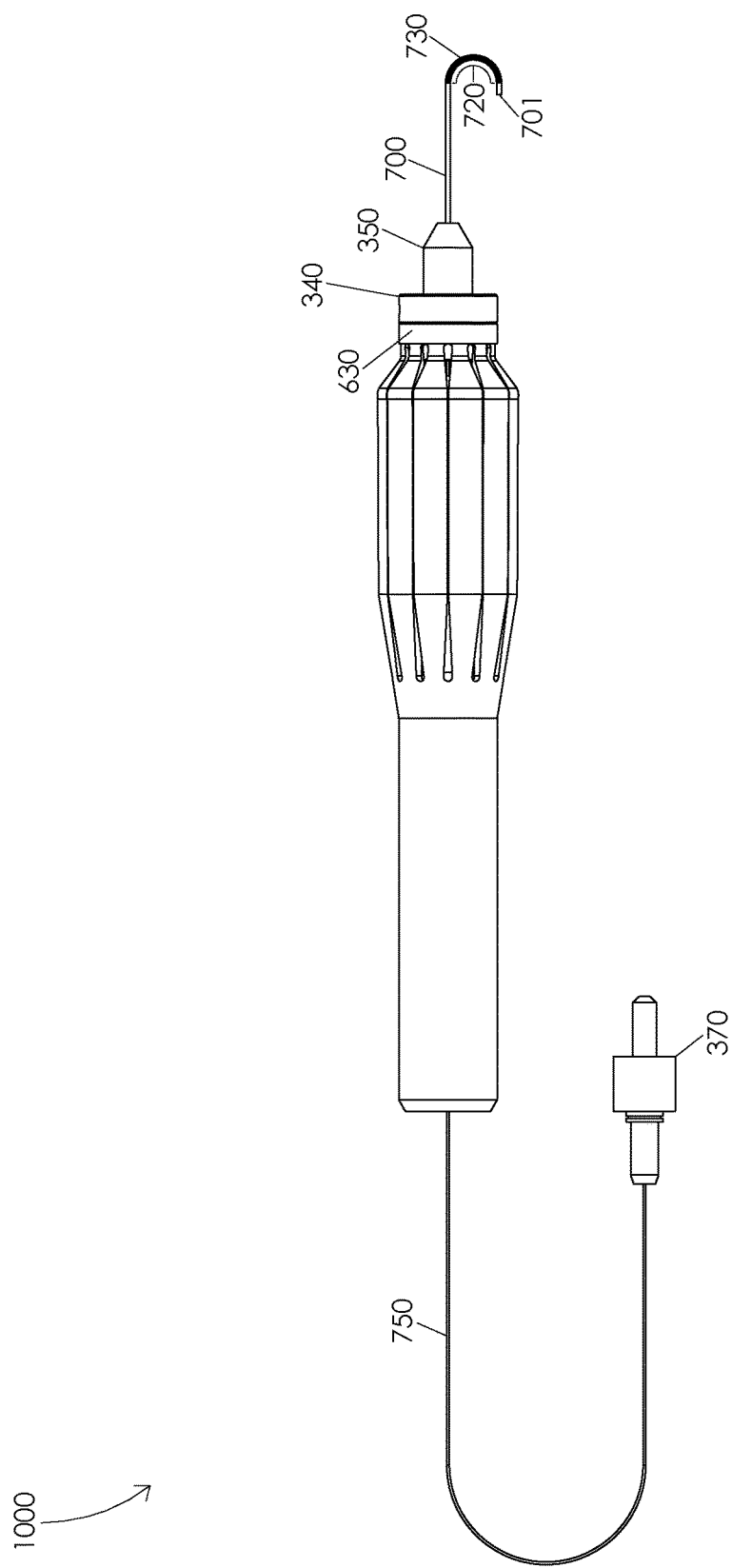
FIGS. 10A, 10B, 10C, 10D, and 10E illustrate a gradual straightening of an optic fiber.

FIGS. 10A, 10B, 10C, 10D, and 10E illustrate a gradual straightening of an optic fiber 750. FIG. 10A illustrates a fully curved optic fiber 1000. In one or more embodiments, optic fiber 750 may comprise a fully curved optic fiber 1000, e.g., when actuation ring 630 is fully extended relative to handle base 610. Illustratively, optic fiber 750 may comprise a fully curved optic fiber 1000, e.g., when actuation structure 620 is fully compressed.

In one or more embodiments, optic fiber 750 may comprise a fully curved optic fiber 1000, e.g., when housing tube 700 is fully extended relative to handle base 610. Illustratively, wire 740 may be configured to fully compress a first housing tube portion 720 of housing tube 700, e.g., when optic fiber 750 comprises a fully curved optic fiber 1000. Illustratively, a line tangent to optic fiber distal end 751 may be parallel to a line tangent to housing tube proximal end 702, e.g., when optic fiber 750 comprises a fully curved optic fiber 1000.

Figure 10B:
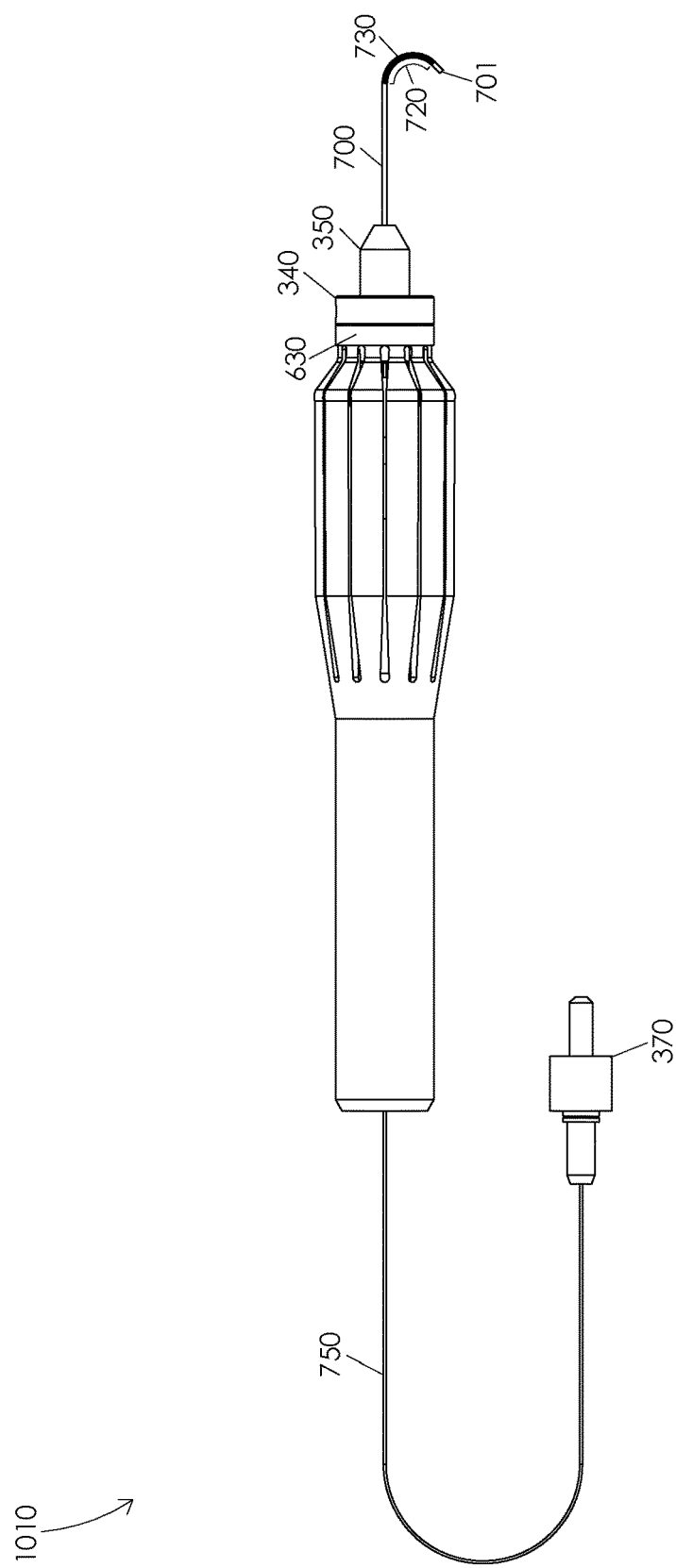

FIG. 10B illustrates an optic fiber in a first partially straightened position 1010. In one or more embodiments, a decompression of a fully compressed actuation structure 620 may be configured to gradually straighten optic fiber 750 from a fully curved optic fiber 1000 to an optic fiber in a first partially straightened position 1010. Illustratively, a decompression of actuation structure 620 may be configured to gradually retract housing tube 700 relative to handle base 610 and wire 740. In one or more embodiments, a gradual retraction of housing tube 700 relative to handle base 610 may be configured to cause wire 740 to reduce a compressive force applied to an inner portion of housing tube 700.

Illustratively, a reduction of a compressive force applied to an inner portion of housing tube 700, e.g., by retracting housing tube 700 relative to handle base 610, may be configured to decompress a first housing tube portion 720 of housing tube 700. For example, wire 740 may be fixed in a position relative to handle base 610 and fixed to an inner portion of housing tube 700. In one or more embodiments, as housing tube 700 is gradually retracted relative to handle base 610, wire 740 may be configured to reduce a compressive force applied to an inner portion of housing tube 700 causing the inner portion of housing tube 700 to gradually be decompressed. Illustratively, a reduction of a compressive force applied to an inner portion of housing tube 700 may be configured to gradually straighten housing tube 700. In one or more embodiments, a gradual straightening of housing tube 700 may be configured to gradually straighten optic fiber 750 from a fully curved optic fiber 1000 to an optic fiber in a first partially straightened position 1010.

Illustratively, a line tangent to optic fiber distal end 751 may intersect a line tangent to housing tube proximal end 702 at a first partially straightened angle, e.g., when optic fiber 750 comprises an optic fiber in a first partially straightened position 1010. In one or more embodiments, the first partially straightened angle may comprise any angle less than 180 degrees. For example, the first partially straightened angle may comprise a 135 degree angle.

Figure 10C:
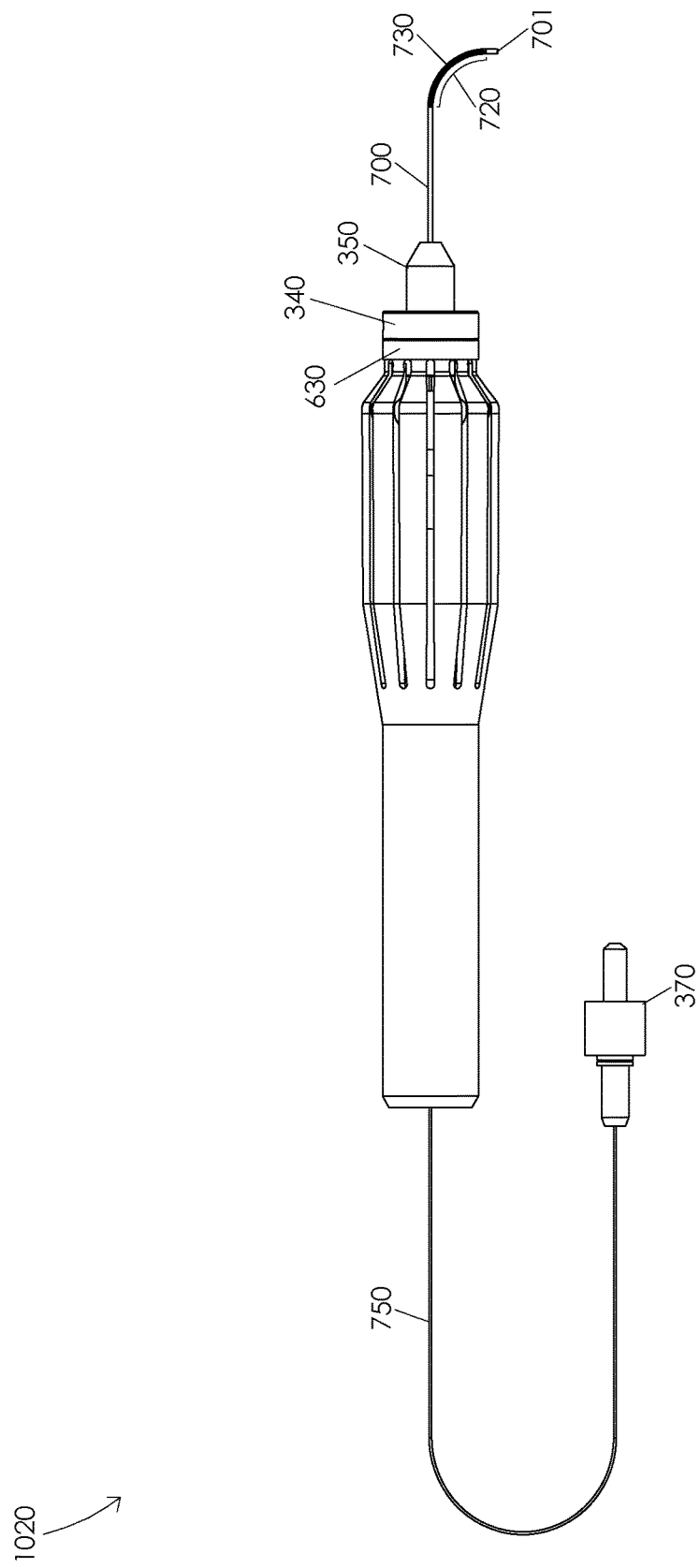

FIG. 10C illustrates an optic fiber in a second partially straightened position 1020. In one or more embodiments, a decompression of actuation structure 620 may be configured to gradually straighten optic fiber 750 from an optic fiber in a first partially straightened position 1010 to an optic fiber in a second partially straightened position 1020. Illustratively, a decompression of actuation structure 620 may be configured to gradually retract housing tube 700 relative to handle base 610 and wire 740. In one or more embodiments, a gradual retraction of housing tube 700 relative to handle base 610 may be configured to cause wire 740 to reduce a compressive force applied to an inner portion of housing tube 700.

Illustratively, a reduction of a compressive force applied to an inner portion of housing tube 700, e.g., by retracting housing tube 700 relative to handle base 610, may be configured to decompress a first housing tube portion 720 of housing tube 700. For example, wire 740 may be fixed in a position relative to handle base 610 and fixed to an inner portion of housing tube 700. In one or more embodiments, as housing tube 700 is gradually retracted relative to handle base 610, wire 740 may be configured to reduce a compressive force applied to an inner portion of housing tube 700 causing the inner portion of housing tube 700 to gradually be decompressed. Illustratively, a reduction of a compressive force applied to an inner portion of housing tube 700 may be configured to gradually straighten housing tube 700. In one or more embodiments, a gradual straightening of housing tube 700 may be configured to gradually straighten optic fiber 750 from an optic fiber in a first partially straightened position 1010 to an optic fiber in a second partially straightened position 1020.

Illustratively, a line tangent to optic fiber distal end 751 may intersect a line tangent to housing tube proximal end 702 at a second partially straightened angle, e.g., when optic fiber 750 comprises an optic fiber in a second partially straightened position 1020. In one or more embodiments, the second partially straightened angle may comprise any angle less than the first partially straightened angle. For example, the second partially straightened angle may comprise a 90 degree angle.

Figure 10D:
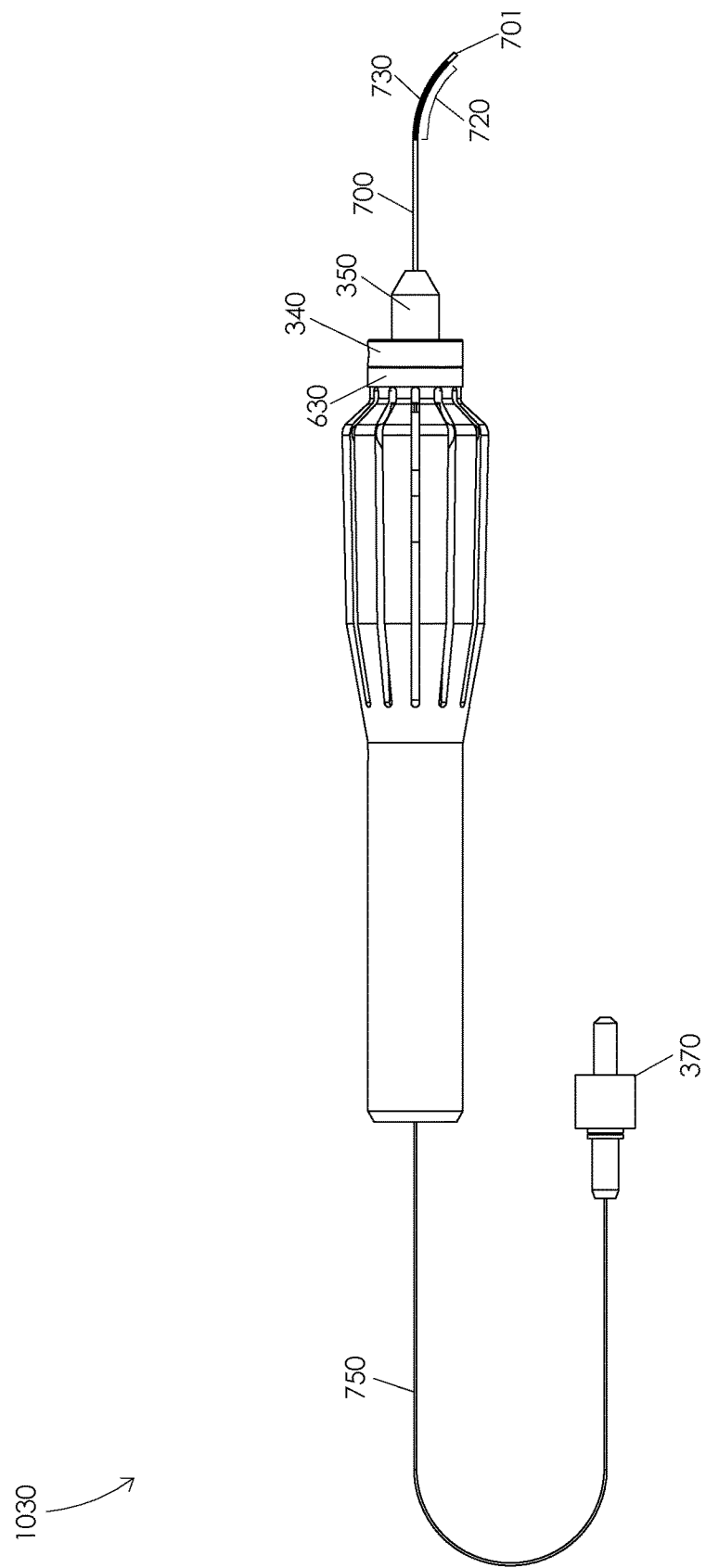

FIG. 10D illustrates an optic fiber in a third partially straightened position 1030. In one or more embodiments, a decompression of actuation structure 620 may be configured to gradually straighten optic fiber 750 from an optic fiber in a second partially straightened position 1020 to an optic fiber in a third partially straightened position 1030. Illustratively, a decompression of actuation structure 620 may be configured to gradually retract housing tube 700 relative to handle base 610 and wire 740. In one or more embodiments, a gradual retraction of housing tube 700 relative to handle base 610 may be configured to cause wire 740 to reduce a compressive force applied to an inner portion of housing tube 700.

Illustratively, a reduction of a compressive force applied to an inner portion of housing tube 700, e.g., by retracting housing tube 700 relative to handle base 610, may be configured to decompress a first housing tube portion 720 of housing tube 700. For example, wire 740 may be fixed in a position relative to handle base 610 and fixed to an inner portion of housing tube 700. In one or more embodiments, as housing tube 700 is gradually retracted relative to handle base 610, wire 740 may be configured to reduce a compressive force applied to an inner portion of housing tube 700 causing the inner portion of housing tube 700 to gradually be decompressed. Illustratively, a reduction of a compressive force applied to an inner portion of housing tube 700 may be configured to gradually straighten housing tube 700. In one or more embodiments, a gradual straightening of housing tube 700 may be configured to gradually straighten optic fiber 750 from an optic fiber in a second partially straightened position 1020 to an optic fiber in a third partially straightened position 1030.

Illustratively, a line tangent to optic fiber distal end 751 may intersect a line tangent to housing tube proximal end 702 at a third partially straightened angle, e.g., when optic fiber 750 comprises an optic fiber in a third partially straightened position 1030. In one or more embodiments, the third partially straightened angle may comprise any angle less than the second partially straightened angle. For example, the third partially straightened angle may comprise a 45 degree angle.

Figure 10E:
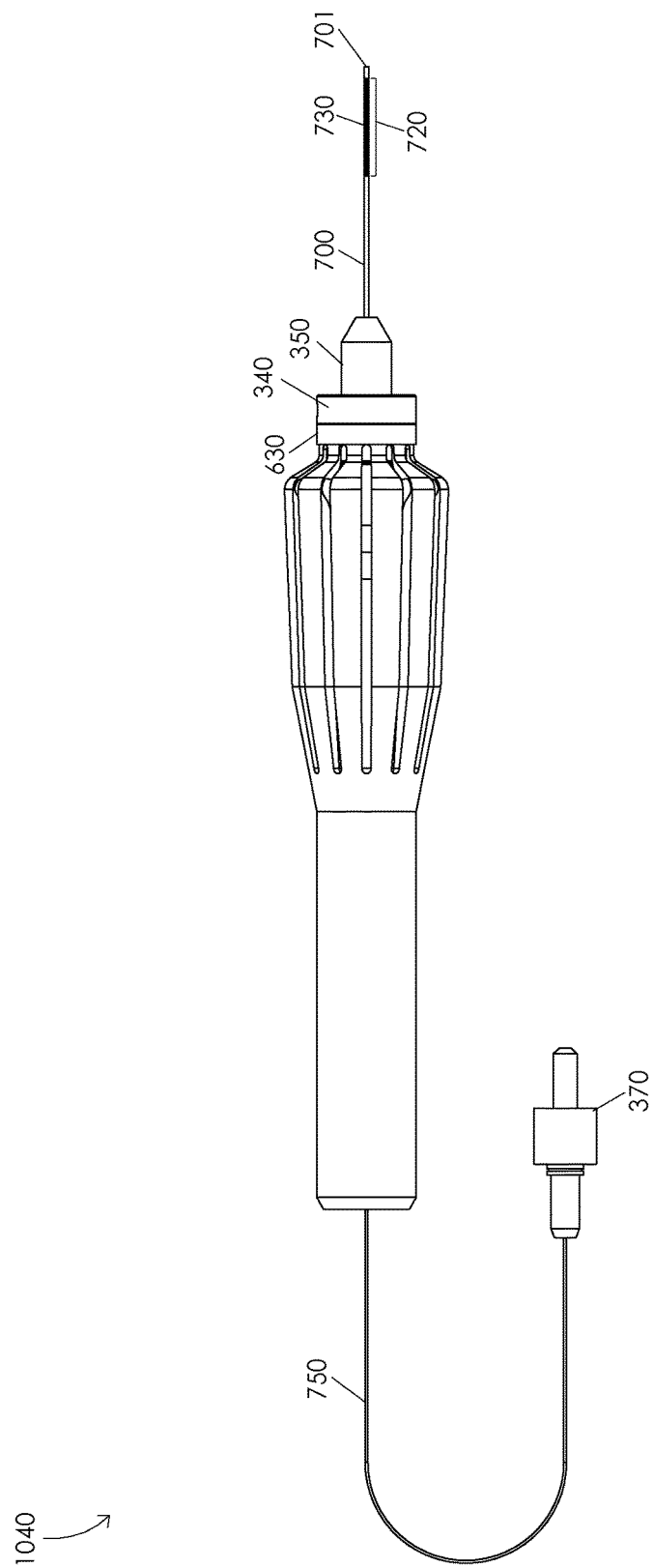

FIG. 10E illustrates an optic fiber in a fully straightened position 1040. In one or more embodiments, a decompression of actuation structure 620 may be configured to gradually straighten optic fiber 750 from an optic fiber in a third partially straightened position 1030 to an optic fiber in a fully straightened position 1040. Illustratively, a decompression of actuation structure 620 may be configured to gradually retract housing tube 700 relative to handle base 610 and wire 740. In one or more embodiments, a gradual retraction of housing tube 700 relative to handle base 610 may be configured to cause wire 740 to reduce a compressive force applied to an inner portion of housing tube 700.

Illustratively, a reduction of a compressive force applied to an inner portion of housing tube 700, e.g., by retracting housing tube 700 relative to handle base 610, may be configured to decompress a first housing tube portion 720 of housing tube 700. For example, wire 740 may be fixed in a position relative to handle base 610 and fixed to an inner portion of housing tube 700. In one or more embodiments, as housing tube 700 is gradually retracted relative to handle base 610, wire 740 may be configured to reduce a compressive force applied to an inner portion of housing tube 700 causing the inner portion of housing tube 700 to gradually be decompressed. Illustratively, a reduction of a compressive force applied to an inner portion of housing tube 700 may be configured to gradually straighten housing tube 700. In one or more embodiments, a gradual straightening of housing tube 700 may be configured to gradually straighten optic fiber 750 from an optic fiber in a third partially straightened position 1030 to an optic fiber in a fully straightened position 1040. Illustratively, a line tangent to optic fiber distal end 751 may be parallel to a line tangent to housing tube proximal end 702, e.g., when optic fiber 750 comprises an optic fiber in a fully straightened position 1040.

Illustratively, a surgeon may aim optic fiber distal end 751 at any of a plurality of targets within an eye, e.g., to perform a photocoagulation procedure. In one or more embodiments, a surgeon may aim optic fiber distal end 751 at any target within a particular transverse plane of the inner eye by, e.g., rotating handle 600 to orient housing tube 700 in an orientation configured to cause a curvature of housing tube 700 within the particular transverse plane of the inner eye and varying an amount of compression of actuation structure 620. Illustratively, a surgeon may aim optic fiber distal end 751 at any target within a particular sagittal plane of the inner eye by, e.g., rotating handle 600 to orient housing tube 700 in an orientation configured to cause a curvature of housing tube 700 within the particular sagittal plane of the inner eye and varying an amount of compression of actuation structure 620. In one or more embodiments, a surgeon may aim optic fiber distal end 751 at any target within a particular frontal plane of the inner eye by, e.g., varying an amount of compression of actuation structure 620 to orient a line tangent to optic fiber distal end 751 wherein the line tangent to optic fiber distal end 751 is within the particular frontal plane of the inner eye and rotating handle 600. Illustratively, a surgeon may aim optic fiber distal end 751 at any target located outside of the particular transverse plane, the particular sagittal plane, and the particular frontal plane of the inner eye, e.g., by varying a rotational orientation of handle 600 and varying an amount of compression of actuation structure 620. In one or more embodiments, a surgeon may aim optic fiber distal end 751 at any target of a plurality of targets within an eye, e.g., without increasing a length of a portion of a steerable laser probe within the eye. Illustratively, a surgeon may aim optic fiber distal end 751 at any target of a plurality of targets within an eye, e.g., without decreasing a length of a portion of a steerable laser probe within the eye.

FIGS. 11A and 11B are schematic diagrams illustrating a handle 1100. FIG. 11A illustrates a top view of handle 1100. In one or more embodiments, handle 1100 may comprise a handle distal end 1101, a handle proximal end 1102, a handle base 1110, an actuation structure 1120, an actuation ring 1130, an actuation mechanism housing 1135, a platform base 1140, an actuation mechanism guide 1145, and a housing tube platform 1150. Illustratively, actuation structure 1120 may comprise an actuation structure distal end 1121 and an actuation structure proximal end 1122. In one or more embodiments, actuation structure 1120 may comprise a plurality of actuation arms 1125. Illustratively, each actuation arm 1125 may comprise at least one extension mechanism 1126. In one or more embodiments, actuation structure 1120 may comprise a shape memory material configured to project actuation structure distal end 1121 a first distance from actuation structure proximal end 1122, e.g., when actuation structure 1120 is fully decompressed. Illustratively, actuation structure 1120 may comprise a shape memory material configured to project actuation structure distal end 1121 a second distance from actuation structure proximal end 1122, e.g., when actuation structure 1120 is fully compressed. In one or more embodiments, the second distance from actuation structure proximal end 1122 may be greater than the first distance from actuation structure proximal end 1122. Actuation structure 1120 may be manufactured from any suitable material, e.g., polymers, metals, metal alloys, etc., or from any combination of suitable materials.

Illustratively, actuation structure 1120 may be compressed by an application of a compressive force to actuation structure 1120. In one or more embodiments, actuation structure 1120 may be compressed by an application of one or more compressive forces located at one or more locations around an outer perimeter of actuation structure 1120. Illustratively, the one or more locations may comprise any of a plurality of locations around the outer perimeter of actuation structure 1120. For example, a surgeon may compress actuation structure 1120 by squeezing actuation structure 1120. Illustratively, the surgeon may compress actuation structure 1120 by squeezing actuation structure 1120 at any particular location of a plurality of locations around an outer perimeter of actuation structure 1120. For example, a surgeon may rotate handle 1100 and compress actuation structure 1120 from any rotational position of a plurality of rotational positions of handle 1100.

In one or more embodiments, actuation structure 1120 may be compressed by an application of a compressive force to any one or more of the plurality of actuation arms 1125. Illustratively, each actuation arm 1125 may be configured to actuate independently. In one or more embodiments, each actuation arm 1125 may be connected to one or more of the plurality of actuation arms 1125 wherein an actuation of a particular actuation arm 1125 may be configured to actuate every actuation arm 1125 of the plurality of actuation arms 1125. Illustratively, one or more actuation arms 1125 may be configured to actuate in pairs or groups. For example, an actuation of a first actuation arm 1125 may be configured to actuate a second actuation arm 1125.

In one or more embodiments, a compression of actuation structure 1120, e.g., due to an application of a compressive force to a particular actuation arm 1125, may be configured to actuate the particular actuation arm 1125. Illustratively, an actuation of the particular actuation arm 1125 may be configured to actuate every actuation arm 1125 of the plurality of actuation arms 1125. In one or more embodiments, an application of a compressive force to a particular actuation arm 1125 may be configured to extend at least one extension mechanism 1126 of the particular actuation arm 1125. Illustratively, a particular actuation arm 1125 may be configured to extend a first length from handle base 1110. An extension of an extension mechanism 1126 of the particular actuation arm 1125, e.g., due to an application of a compressive force to the particular actuation arm 1125, may be configured to extend the particular actuation arm 1125 a second length from handle base 1110. Illustratively, the second length from handle base 1110 may be greater than the first length from handle base 1110.

In one or more embodiments, actuation ring 1130 may be fixed to actuation structure distal end 1121. Illustratively, a compression of actuation structure 1120 may be configured to gradually extend actuation ring 1130 from handle base 1110. For example, actuation ring 1130 may be configured to extend a first distance from actuation structure proximal end 1122, e.g., when actuation structure 1120 is fully decompressed. Actuation ring 1130 may be configured to extend a second distance from actuation structure proximal end 1122, e.g., due to a compression of actuation structure 1120. Illustratively, the second distance from actuation structure proximal end 1122 may be greater than the first distance from actuation structure proximal end 1122.

FIG. 11B illustrates a cross-sectional view of handle 1100. In one or more embodiments, handle 1100 may comprise an inner bore 1160, an inner bore proximal taper 1161, an inner bore distal chamber 1162, a draw wire proximal guide 1163, a draw wire proximal end housing 1164, a draw wire distal guide 1165, and a pulley mechanism housing 1170. Handle 1100 may be manufactured from any suitable material, e.g., polymers, metals, metal alloys, etc., or from any combination of suitable materials.

Figure 12:
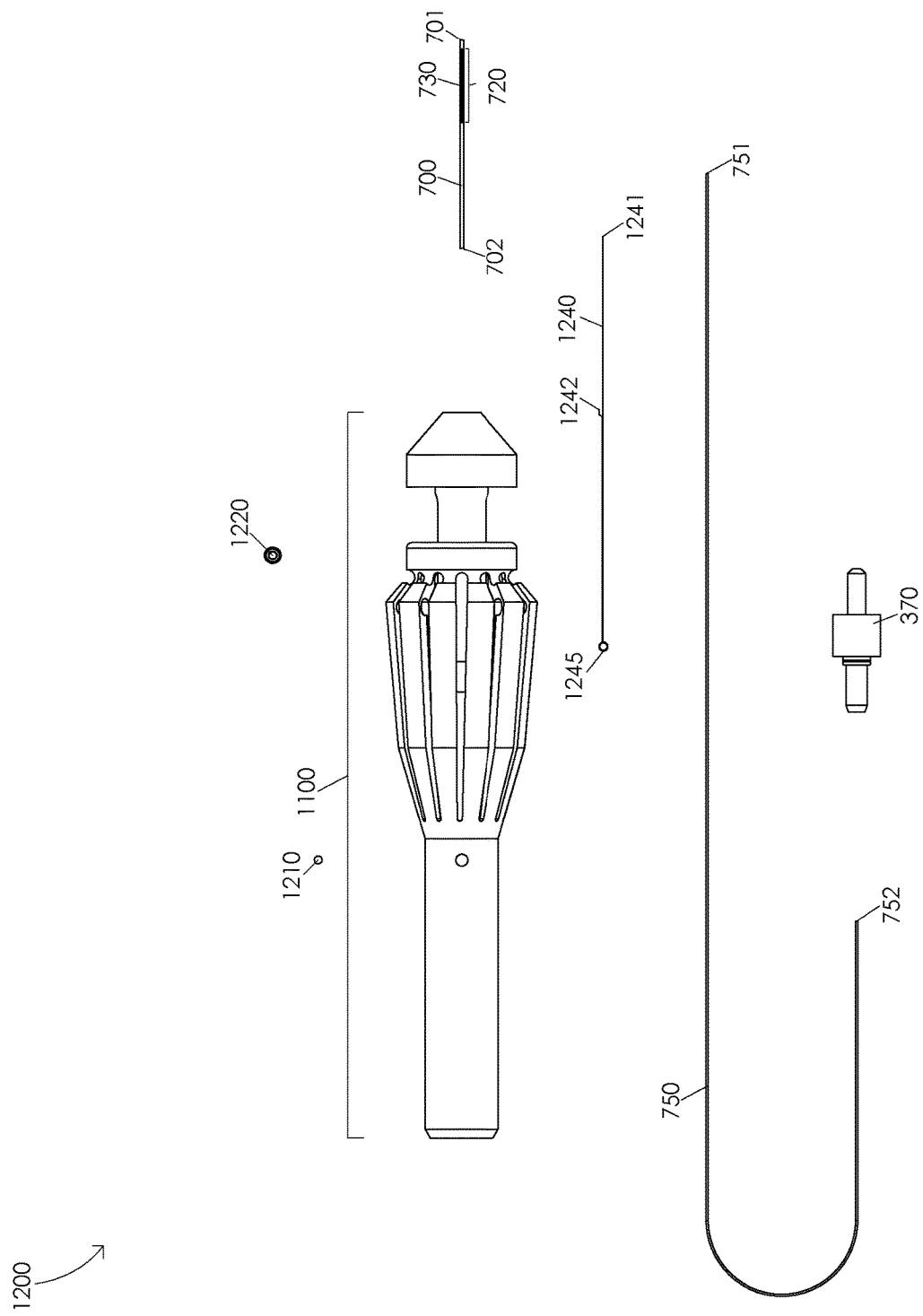
FIG. 12 is a schematic diagram illustrating an exploded view of a steerable laser probe assembly.

FIG. 12 is a schematic diagram illustrating an exploded view of a steerable laser probe assembly 1200. In one or more embodiments, steerable laser probe assembly 1200 may comprise a handle 1100; a housing tube 700 having a housing tube distal end 701 and a housing tube proximal end 702; an optic fiber 750 having an optic fiber distal end 751 and an optic fiber proximal end 752; a pulley mechanism 1210; an actuation mechanism 1220; a draw wire 1240 having a draw wire distal end 1241, a draw wire proximal end 1242, and a draw wire loop 1245; and a light source interface 370. Illustratively, light source interface 370 may be configured to interface with optic fiber proximal end 752. In one or more embodiments, light source interface 370 may comprise a standard light source connecter, e.g., an SMA connector.

Illustratively, housing tube 700 may be fixed to housing tube platform 1150, e.g., housing tube proximal end 702 may be fixed to handle distal end 1101. In one or more embodiments, housing tube 700 may comprise a first housing tube portion 720 having a first stiffness and a second housing tube portion 730 having a second stiffness. Illustratively, the second stiffness may be greater than the first stiffness.

In one or more embodiments, pulley mechanism 1210 may be disposed within pulley mechanism housing 1170. Illustratively, pulley mechanism 1210 may be configured to change a direction of an applied force, e.g., a force applied to draw wire 1240. For example, pulley mechanism 1210 may comprise any suitable mechanism configured to change a direction of an applied force. Illustratively, pulley mechanism 1210 may be configured to change a point of application of an applied force, e.g., by changing a direction of an applied force. For example, pulley mechanism 1210 may be configured to change a direction and a point of application of an applied force, e.g., a force applied to draw wire 1240. In one or more embodiments, pulley mechanism 1210 may comprise a rod configured to change a direction of an applied force, e.g., a force applied to draw wire 1240. For example, pulley mechanism 1210 may comprise a rod configured to change a point of application of an applied force, e.g., a force applied to draw wire 1240. Illustratively, pulley mechanism 1210 may comprise one or more channels configured to, e.g., interface with a portion of draw wire 1240. In one or more embodiments, a portion of pulley mechanism 1210 may be coated with a lubricant, e.g., Teflon, configured to minimize a force of friction between pulley mechanism 1210 and draw wire 1240. Illustratively, pulley mechanism 1210 may be configured to rotate, e.g., to change a direction of an applied force, or a portion of pulley mechanism 1210, e.g., a wheel, may be configured to rotate, e.g., to change a direction of an applied force. For example, pulley mechanism 1210 or a portion of pulley mechanism 1210 may be configured to change a point of application of an applied force, e.g., a force applied to draw wire 1240. In one or more embodiments, pulley mechanism 1210 may be configured to remain in static equilibrium, e.g., not to rotate, to change a direction of an applied force, e.g., a force applied to draw wire 1240. For example, a change in a direction of an applied force may be configured to change one or more points of application of the applied force. Illustratively, a portion of pulley mechanism 1210 may be configured to house a portion of optic fiber 750.

In one or more embodiments, draw wire 1240 may be disposed within draw wire proximal end housing 1164, e.g., draw wire proximal end 1242 may be disposed within draw wire proximal end housing 1164. Illustratively, actuation mechanism 1220 may be disposed within actuation mechanism housing 1135. In one or more embodiments, actuation mechanism 1220 may be configured to fix a portion of draw wire 1240 in a position relative to actuation mechanism 1220, e.g., actuation mechanism 1220 may be configured to fix draw wire proximal end 1242 in a position relative to actuation mechanism 1220. Illustratively, actuation mechanism 1220 may comprise a set screw configured to fix draw wire proximal end 1242 in a position relative to actuation mechanism 1220, e.g., at draw wire proximal end housing 1164.

In one or more embodiments, draw wire 1240 may be disposed within draw wire proximal end housing 1164, inner bore distal chamber 1162, inner bore 1160, draw wire proximal guide 1163, draw wire distal guide 1165, and housing tube 700. Illustratively, pulley mechanism 1210 may be disposed within draw wire loop 1245, e.g., draw wire 1240 may be looped around pulley mechanism 1210. In one or more embodiments, draw wire 1240 may be disposed within housing tube 700 wherein draw wire distal end 1241 may be adjacent to housing tube distal end 701. Illustratively, draw wire 1240 may be disposed within housing tube 700 wherein draw wire 1240 may be adjacent to a first housing tube portion 720. In one or more embodiments, a portion of draw wire 1240 may be fixed to an inner portion of housing tube 700, e.g., by a biocompatible adhesive or any other suitable fixation means.

Illustratively, optic fiber 750 may be disposed within inner bore 1160, inner bore distal chamber 1162, draw wire proximal guide 1163, draw wire distal guide 1165, and housing tube 700. In one or more embodiments, optic fiber 750 may be disposed within pulley mechanism housing 1170, e.g., optic fiber 750 may be disposed within pulley mechanism 1210. Illustratively, optic fiber 750 may be disposed within housing tube 700 wherein optic fiber distal end 751 may be adjacent to housing tube distal end 701. In one or more embodiments, optic fiber 750 may be disposed within housing tube 700 wherein optic fiber 750 may be adjacent to a first housing tube portion 720. Illustratively, a portion of optic fiber 750 may be fixed to an inner portion of housing tube 700, e.g., by a biocompatible adhesive or any other suitable fixation means.

In one or more embodiments, a compression of actuation structure 1120 may be configured to extend actuation ring 1130 relative to handle base 1110. Illustratively, a compression of actuation structure 1120 may be configured to actuate actuation ring 1130 away from handle proximal end 1102 and towards housing tube platform 1150. In one or more embodiments, a compression of actuation structure 1120 may be configured to extend actuation mechanism 1220 relative to handle base 1110. Illustratively, a compression of actuation structure 1120 may be configured to actuate actuation mechanism 1220, e.g., within actuation mechanism guide 1145, away from handle proximal end 1102 and towards housing tube platform 1150.

In one or more embodiments, an extension of actuation mechanism 1220 relative to handle base 1110, e.g., due to a compression of actuation structure 1120, may be configured to apply an extension force to draw wire 1240. For example, an extension of actuation mechanism 1220 relative to handle base 1110 may be configured to pull draw wire proximal end 1242 away from handle proximal end 1102 and towards housing tube platform 1150. Illustratively, an extension of actuation mechanism 1220 relative to handle base 1110 may be configured to extend draw wire proximal end 1242 relative to handle base 1110. For example, an extension of actuation mechanism 1220 relative to handle base 1110 may be configured to extend draw wire proximal end 1242 away from handle proximal end 1102 and towards housing tube platform 1150.

In one or more embodiments, pulley mechanism 1210 may be configured to change a direction of an extension force applied to draw wire 1240. Illustratively, pulley mechanism 1210 may be configured to change a direction of an extension force applied to draw wire 1240. For example, pulley mechanism 1210 may be configured to change a direction of a force applied to draw wire 1240 from an extension direction to a retraction direction. In one or more embodiments, pulley mechanism 1210 may be configured to change a point of application of a force applied to draw wire 1240. For example, pulley mechanism 1210 may be configured to change a point of application of a force applied to draw wire 1240 from draw wire proximal end 1242 to draw wire distal end 1241. Illustratively, pulley mechanism 1210 may be configured to change a location of a point of application of a force applied to draw wire 1240 from a location wherein a first portion of draw wire 1240 may be fixed in a position relative actuation mechanism 1220 to a location wherein a second portion of draw wire 1240 may be fixed to an inner portion of housing tube 700.

In one or more embodiments, a compression of actuation structure 1120 may be configured to apply a compressive force to an inner portion of housing tube 700. For example, a compression of actuation structure 1120 may be configured apply an extension force to draw wire proximal end 1242 and pulley mechanism 1210 may be configured to change the extension force applied to draw wire proximal end 1242 to a compressive force applied to an inner portion of housing tube 700. Illustratively, an application of a compressive force to an inner portion of housing tube 700, e.g., due to a compression of actuation structure 1120, may be configured to gradually compress a first housing tube portion 720 of housing tube 700. In one or more embodiments, a gradual compression of first housing tube portion 720 of housing tube 700 may be configured to cause housing tube 700 to gradually curve. Illustratively, a gradual curving of housing tube 700 may be configured to gradually curve optic fiber 750.

In one or more embodiments, a decompression of actuation structure 1120 may be configured to retract actuation ring 1130 relative to handle base 1110. Illustratively, a decompression of actuation structure 1120 may be configured to actuate actuation ring 1130 towards handle proximal end 1102 and away from housing tube platform 1150. In one or more embodiments, a decompression of actuation structure 1120 may be configured to retract actuation mechanism 1220 relative to handle base 1110. Illustratively, a decompression of actuation structure 1120 may be configured to actuate actuation mechanism 1220, e.g., within actuation mechanism guide 1145, towards handle proximal end 1102 and away from housing tube platform 1150.

In one or more embodiments, a retraction of actuation mechanism 1220 relative to handle base 1110, e.g., due to a decompression of actuation structure 1120, may be configured to reduce an extension force applied to draw wire 1240. Illustratively, a retraction of actuation mechanism 1220 relative to handle base 1110 may be configured to retract draw wire proximal end 1242 relative to handle base 1110. For example, a retraction of actuation mechanism 1220 relative to handle base 1110 may be configured to retract draw wire proximal end 1242 towards handle proximal end 1102 and away from housing tube platform 1150.

In one or more embodiments, a decompression of actuation structure 1120 may be configured to reduce a compressive force applied to an inner portion of housing tube 700. For example, a decompression of actuation structure 1120 may be configured to reduce an extension force applied to draw wire proximal end 1242 and pulley mechanism 1210 may be configured to change a reduction of the extension force applied to draw wire proximal end 1242 to a reduction of a compressive force applied to an inner portion of housing tube 700. Illustratively, a reduction of a compressive force applied to an inner portion of housing tube 700, e.g., due to a decompression of actuation structure 1120, may be configured to gradually decompress a first housing tube portion 720 of housing tube 700. In one or more embodiments, a gradual decompression of first housing tube portion 720 of housing tube 700 may be configured to cause housing tube 700 to gradually straighten. Illustratively, a gradual straightening of housing tube 700 may be configured to gradually straighten optic fiber 750.

Figure 13A:
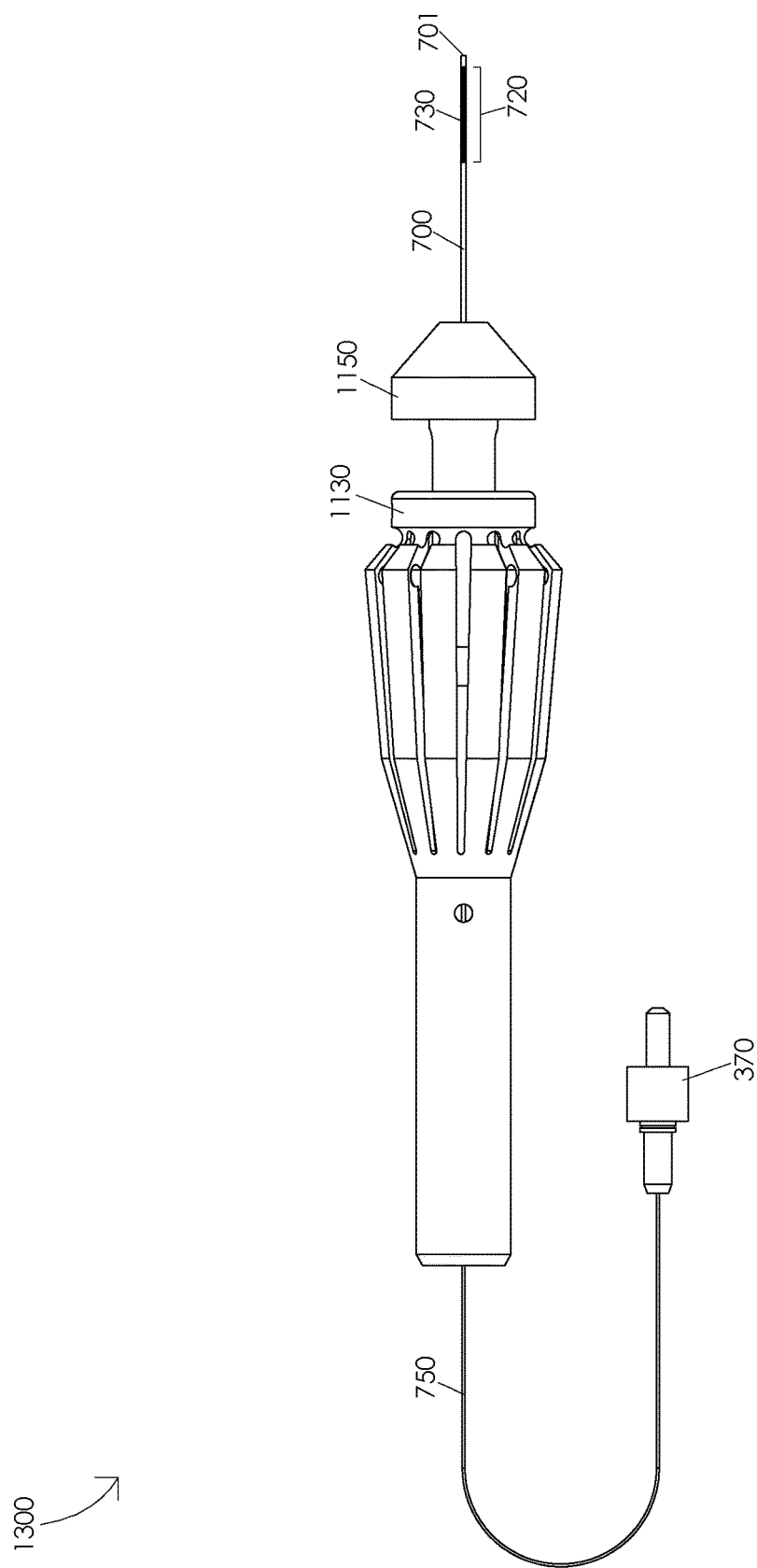
FIGS. 13A, 13B, 13C, 13D, and 13E illustrate a gradual curving of an optic fiber.

FIGS. 13A, 13B, 13C, 13D, and 13E illustrate a gradual curving of an optic fiber 750. FIG. 13A illustrates a straight optic fiber 1300. In one or more embodiments, optic fiber 750 may comprise a straight optic fiber 1300, e.g., when actuation ring 1130 is fully retracted relative to handle base 1110. Illustratively, optic fiber 750 may comprise a straight optic fiber 1300, e.g., when actuation structure 1120 is fully decompressed. In one or more embodiments, optic fiber 750 may comprise a straight optic fiber 1300, e.g., when actuation mechanism 1220 is fully retracted relative to handle base 1110. Illustratively, a line tangent to optic fiber distal end 751 may be parallel to a line tangent to housing tube proximal end 702, e.g., when optic fiber 750 comprises a straight optic fiber 1300.

Figure 13B:
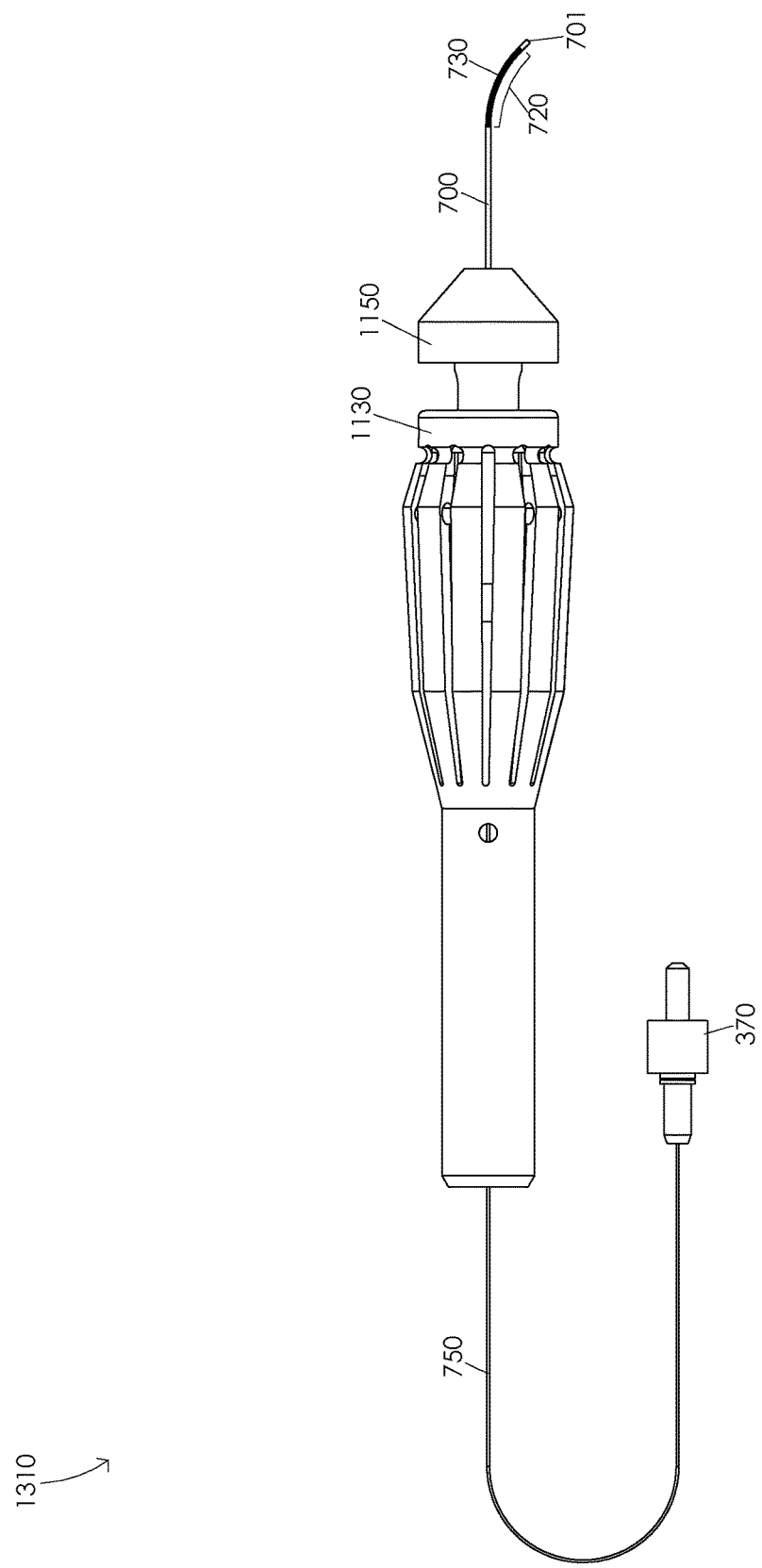

FIG. 13B illustrates an optic fiber in a first curved position 1310. In one or more embodiments, a compression of a fully decompressed actuation structure 1120 may be configured to gradually curve optic fiber 750 from a straight optic fiber 1300 to an optic fiber in a first curved position 1310. Illustratively, a compression of actuation structure 1120 may be configured to gradually extend actuation mechanism 1220 relative to handle base 1110. In one or more embodiments, a gradual extension of actuation mechanism 1220 relative to handle base 1110 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to a first housing tube portion 720 of housing tube 700 may be configured to gradually curve housing tube 700. Illustratively, a gradual curving of housing tube 700 may be configured to gradually curve optic fiber 750 from a straight optic fiber 1300 to an optic fiber in a first curved position 1310. In one or more embodiments, a line tangent to optic fiber distal end 751 may intersect a line tangent to housing tube proximal end 702 at a first angle, e.g., when optic fiber 750 comprises an optic fiber in a first curved position 1310. Illustratively, the first angle may comprise any angle greater than zero degrees. For example, the first angle may comprise a 45 degree angle.

Figure 13C:
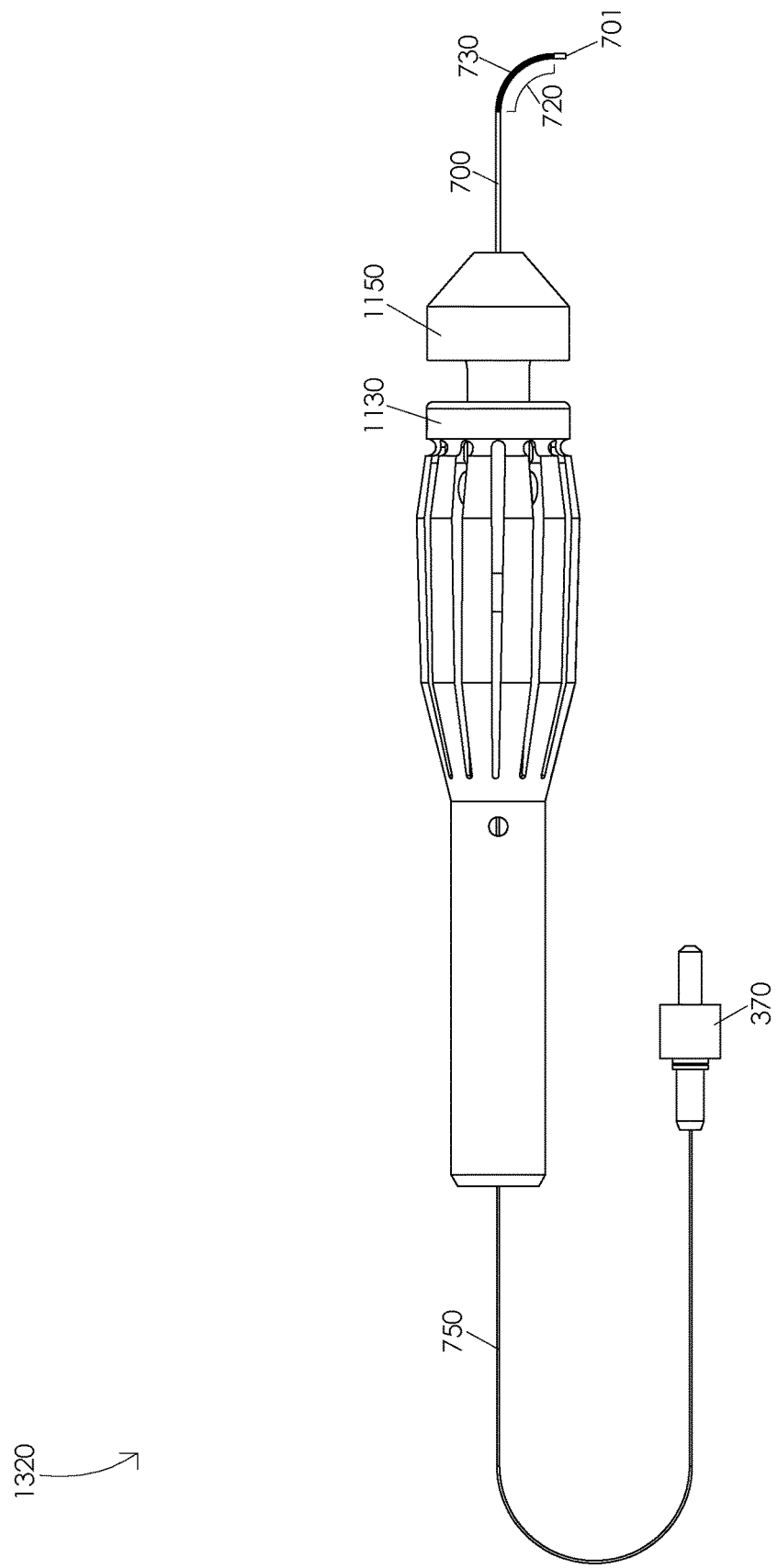

FIG. 13C illustrates an optic fiber in a second curved position 1320. In one or more embodiments, a compression of actuation structure 1120 may be configured to gradually curve optic fiber 750 from an optic fiber in a first curved position 1310 to an optic fiber in a second curved position 1320. Illustratively, a compression of actuation structure 1120 may be configured to gradually extend actuation mechanism 1220 relative to handle base 1110. In one or more embodiments, a gradual extension of actuation mechanism 1220 relative to handle base 1110 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750 from an optic fiber in a first curved position 1310 to an optic fiber in a second curved position 1320. In one or more embodiments, a line tangent to optic fiber distal end 751 may intersect a line tangent to housing tube proximal end 702 at a second angle, e.g., when optic fiber 750 comprises an optic fiber in a second curved position 1320. Illustratively, the second angle may comprise any angle greater than the first angle. For example, the second angle may comprise a 90 degree angle.

Figure 13D:
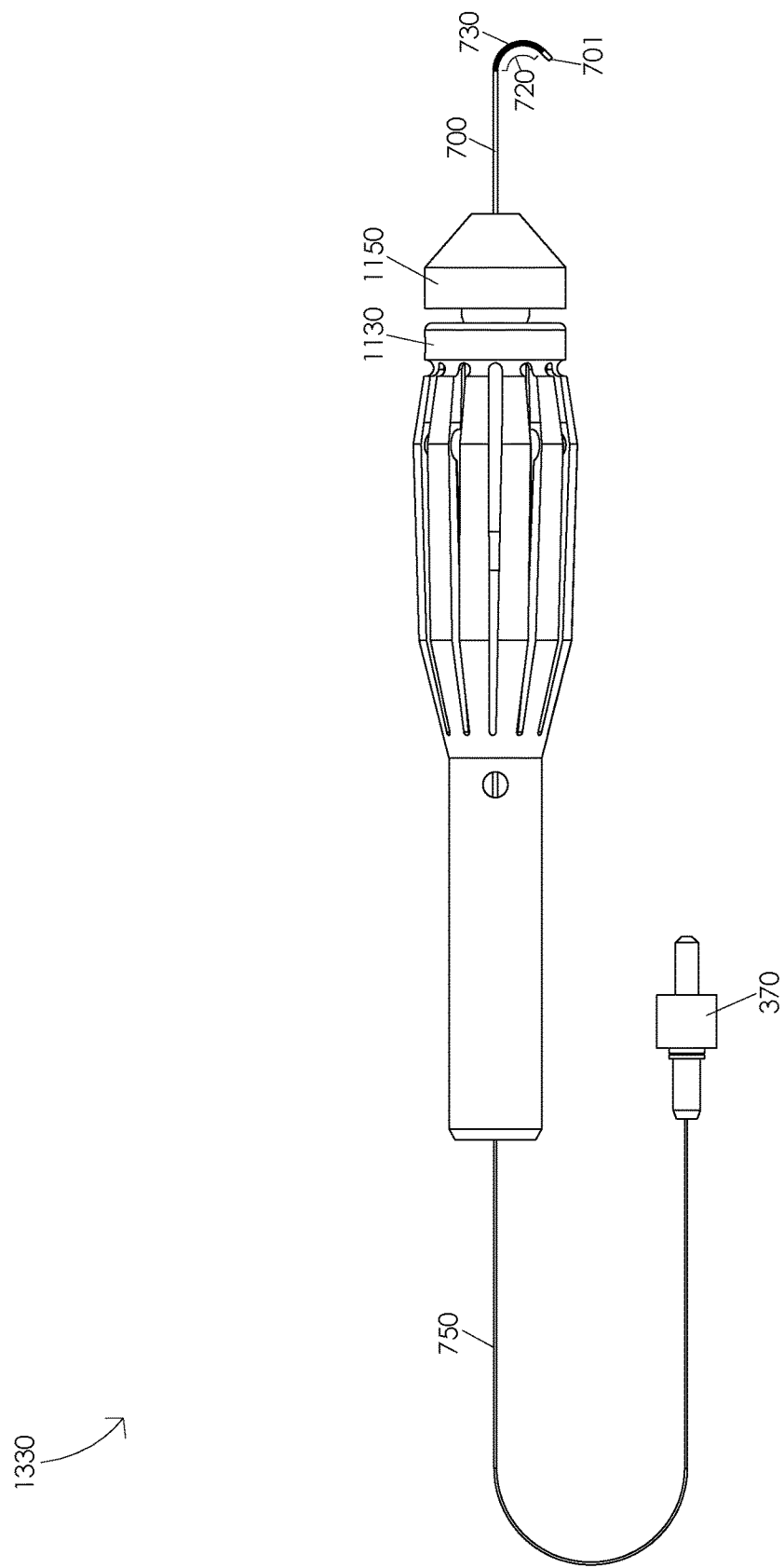

FIG. 13D illustrates an optic fiber in a third curved position 1330. In one or more embodiments, a compression of actuation structure 1120 may be configured to gradually curve optic fiber 750 from an optic fiber in a second curved position 1320 to an optic fiber in a third curved position 1330. Illustratively, a compression of actuation structure 1120 may be configured to gradually extend actuation mechanism 1220 relative to handle base 1110. In one or more embodiments, a gradual extension of actuation mechanism 1220 relative to handle base 1110 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750 from an optic fiber in a second curved position 1320 to an optic fiber in a third curved position 1330. In one or more embodiments, a line tangent to optic fiber distal end 751 may intersect a line tangent to housing tube proximal end 702 at a third angle, e.g., when optic fiber 750 comprises an optic fiber in a third curved position 1330. Illustratively, the third angle may comprise any angle greater than the second angle. For example, the third angle may comprise a 135 degree angle.

Figure 13E:
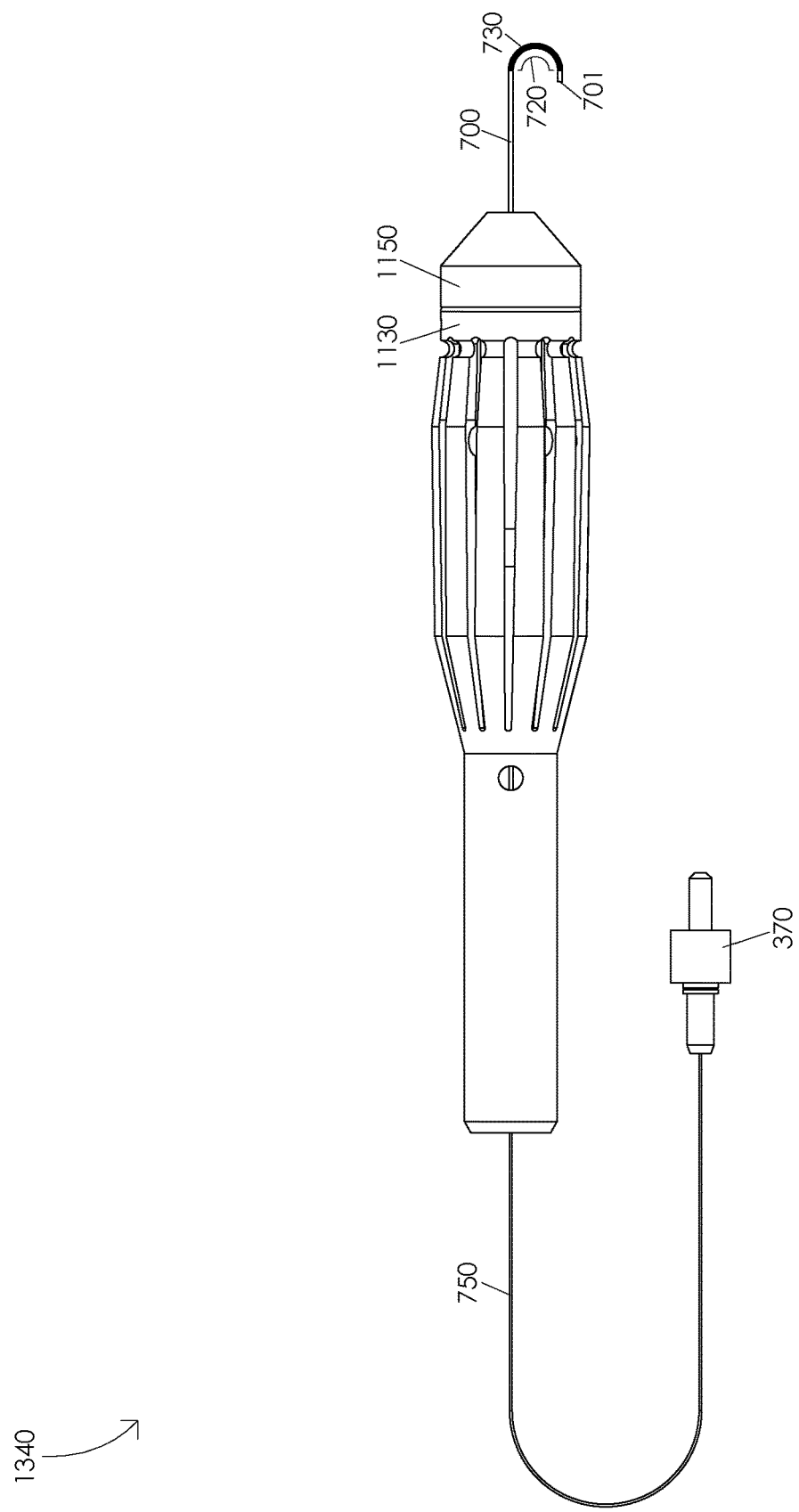

FIG. 13E illustrates an optic fiber in a fourth curved position 1340. In one or more embodiments, a compression of actuation structure 1120 may be configured to gradually curve optic fiber 750 from an optic fiber in a third curved position 1330 to an optic fiber in a fourth curved position 1340. Illustratively, a compression of actuation structure 1120 may be configured to gradually extend actuation mechanism 1220 relative to handle base 1110. In one or more embodiments, a gradual extension of actuation mechanism 1220 relative to handle base 1110 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750 from an optic fiber in a third curved position 1330 to an optic fiber in a forth curved position 1340. In one or more embodiments, a line tangent to optic fiber distal end 751 may be parallel to a line tangent to housing tube proximal end 702, e.g., when optic fiber 750 comprises an optic fiber in a fourth curved position 1340.

In one or more embodiments, one or more properties of a steerable laser probe may be adjusted to attain one or more desired steerable laser probe features. For example, a length that housing tube 700 extends from handle distal end 1101 may be adjusted to vary an amount of compression of actuation structure 1120 configured to curve housing tube 700 to a particular curved position. In one or more embodiments, a portion of draw wire 1240 may be fixed to an outer portion of housing tube 700 wherein a compression of actuation structure 1120 may be configured to cause draw wire 1240 to compress a first housing tube portion 720 of housing tube 700. Illustratively, a position of pulley mechanism 1210 or a length of draw wire 1240 may be adjusted to vary an amount of compression of actuation structure 1120 configured to curve housing tube 700 to a particular curved position. In one or more embodiments, a stiffness of first housing tube portion 720 or a stiffness of second housing tube portion 730 may be adjusted to vary an amount of compression of actuation structure 1120 configured to curve housing tube 700 to a particular curved position. Illustratively, a material comprising first housing tube portion 720 or a material comprising second housing tube portion 730 may be adjusted to vary an amount of compression of actuation structure 1120 configured to curve housing tube 700 to a particular curved position.

In one or more embodiments, a number of apertures in housing tube 700 may be adjusted to vary an amount of compression of actuation structure 1120 configured to curve housing tube 700 to a particular curved position. Illustratively, a location of one or more apertures in housing tube 700 may be adjusted to vary an amount of compression of actuation structure 1120 configured to curve housing tube 700 to a particular curved position. In one or more embodiments, a geometry of one or more apertures in housing tube 700 may be adjusted to vary an amount of compression of action structure 1120 configured to curve housing tube 700 to a particular curved position. Illustratively, a geometry of one or more apertures in housing tube 700 may be uniform, e.g., each aperture of the one or more apertures may have a same geometry. In one or more embodiments, a geometry of one or more apertures in housing tube 700 may be non-uniform, e.g., a first aperture in housing tube 700 may have a first geometry and a second aperture in housing tube 700 may have a second geometry.

In one or more embodiments, a geometry of actuation structure 1120 may be adjusted to vary an amount of compression of actuation structure 1120 configured to curve housing tube 700 to a particular curved position. Illustratively, one or more locations within housing tube 700 wherein draw wire 1240 may be fixed to an inner portion of housing tube 700 may be adjusted to vary an amount of compression of actuation structure 1120 configured to curve housing tube 700 to a particular curved position. In one or more embodiments, at least a portion of optic fiber 750 may be enclosed in an optic fiber sleeve configured to, e.g., protect optic fiber 750, vary a stiffness of optic fiber 750, vary an optical property of optic fiber 750, etc.

Figure 14A:
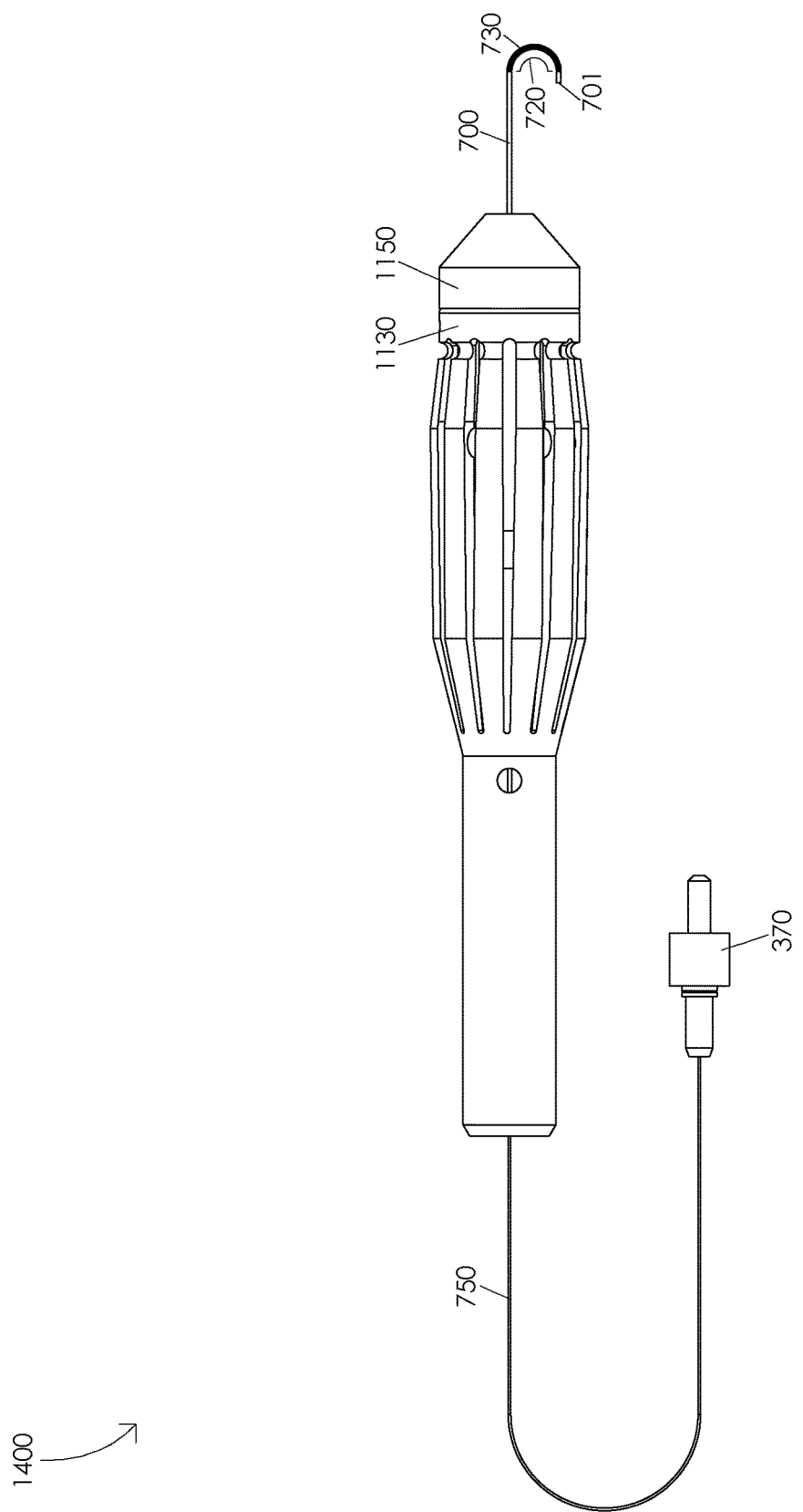
FIGS. 14A, 14B, 14C, 14D, and 14E illustrate a gradual straightening of an optic fiber.

FIGS. 14A, 14B, 14C, 14D, and 14E illustrate a gradual straightening of an optic fiber 750. FIG. 14A illustrates a fully curved optic fiber 1400. In one or more embodiments, optic fiber 750 may comprise a fully curved optic fiber 1400, e.g., when actuation ring 1130 is fully extended relative to handle base 1110. Illustratively, optic fiber 750 may comprise a fully curved optic fiber 1400, e.g., when actuation structure 1120 is fully compressed. In one or more embodiments, optic fiber 750 may comprise a fully curved optic fiber 1400, e.g., when actuation mechanism 1220 is fully extended relative to handle base 1110. Illustratively, draw wire 1240 may be configured to fully compress a first housing tube portion 720 of housing tube 700, e.g., when optic fiber 750 comprises a fully curved optic fiber 1400. Illustratively, a line tangent to optic fiber distal end 751 may be parallel to a line tangent to housing tube proximal end 702, e.g., when optic fiber 750 comprises a fully curved optic fiber 1400.

Figure 14B:
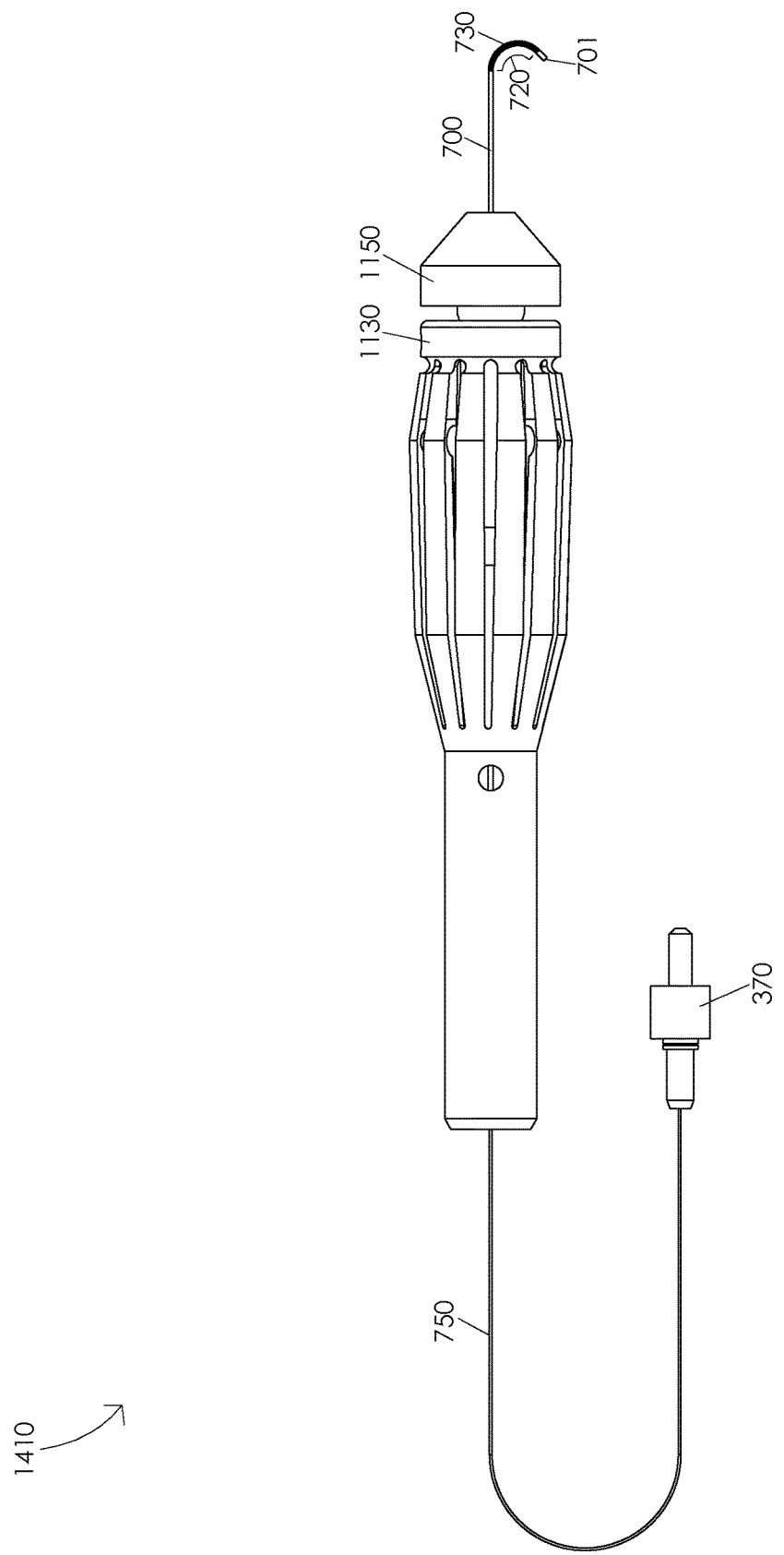

FIG. 14B illustrates an optic fiber in a first partially straightened position 1410. In one or more embodiments, a decompression of a fully compressed actuation structure 1120 may be configured to gradually straighten optic fiber 750 from a fully curved optic fiber 1400 to an optic fiber in a first partially straightened position 1410. Illustratively, a decompression of actuation structure 1120 may be configured to gradually retract actuation mechanism 1220 relative to handle base 1110. In one or more embodiments, a gradual retraction of actuation mechanism 1220 relative to handle base 1110 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750 from a fully curved optic fiber 1400 to an optic fiber in a first partially straightened position 1410. In one or more embodiments, a line tangent to optic fiber distal end 751 may intersect a line tangent to housing tube proximal end 702 at a first partially straightened angle, e.g., when optic fiber 750 comprises an optic fiber in a first partially straightened position 1410. Illustratively, the first partially straightened angle may comprise any angle less than 180 degrees. For example, the first partially straightened angle may comprise a 135 degree angle.

Figure 14C:
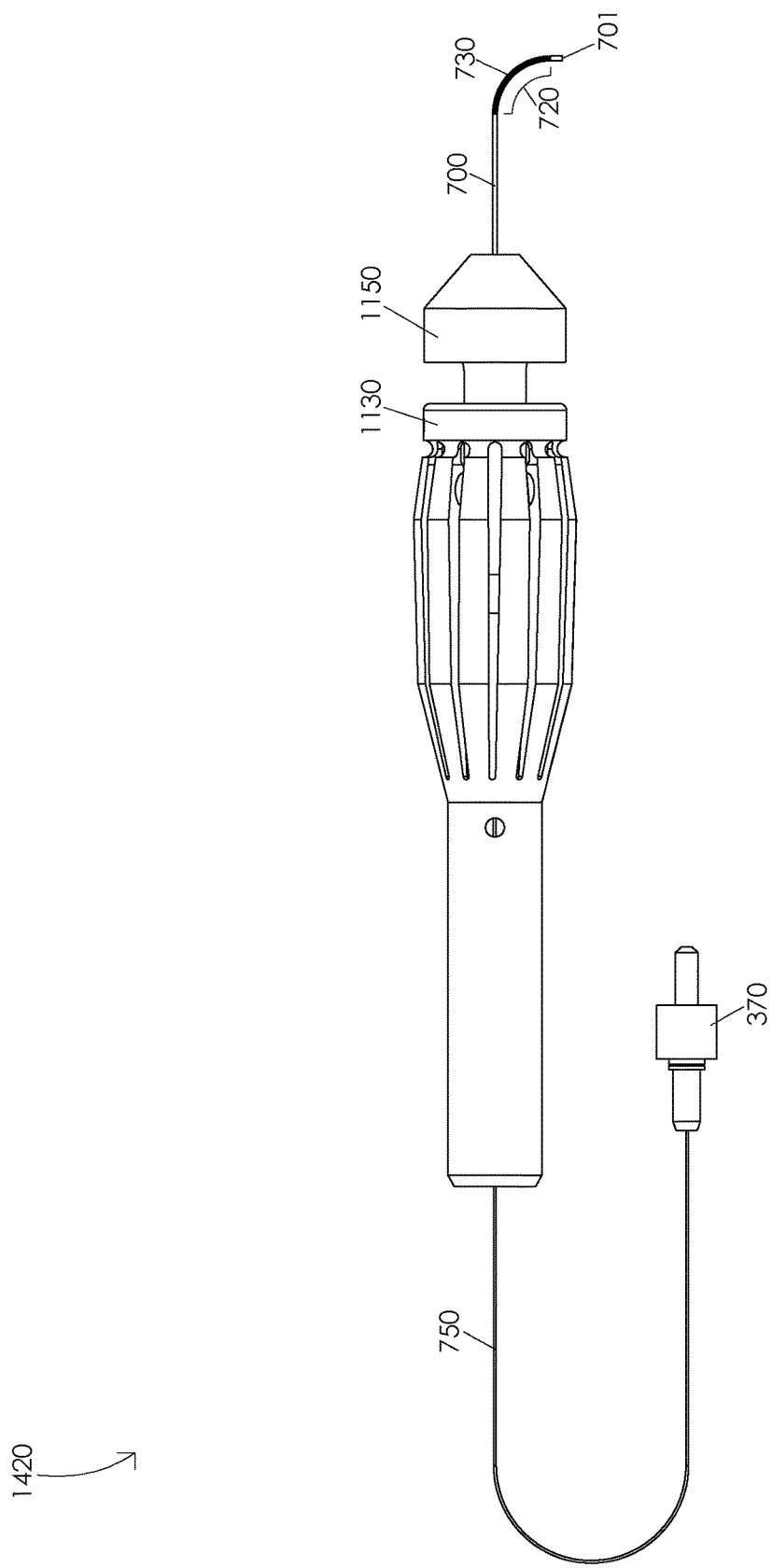

FIG. 14C illustrates an optic fiber in a second partially straightened position 1420. In one or more embodiments, a decompression of actuation structure 1120 may be configured to gradually straighten optic fiber 750 from an optic fiber in a first partially straightened position 1410 to an optic fiber in a second partially straightened position 1420. Illustratively, a decompression of actuation structure 1120 may be configured to gradually retract actuation mechanism 1220 relative to handle base 1110. In one or more embodiments, a gradual retraction of actuation mechanism 1220 relative to handle base 1110 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750 from an optic fiber in a first partially straightened position 1410 to an optic fiber in a second partially straightened position 1420. In one or more embodiments, a line tangent to optic fiber distal end 751 may intersect a line tangent to housing tube proximal end 702 at a second partially straightened angle, e.g., when optic fiber 750 comprises an optic fiber in a second partially straightened position 1420. Illustratively, the second partially straightened angle may comprise any angle less than the first partially straightened angle. For example, the second partially straightened angle may comprise a 90 degree angle.

Figure 14D:
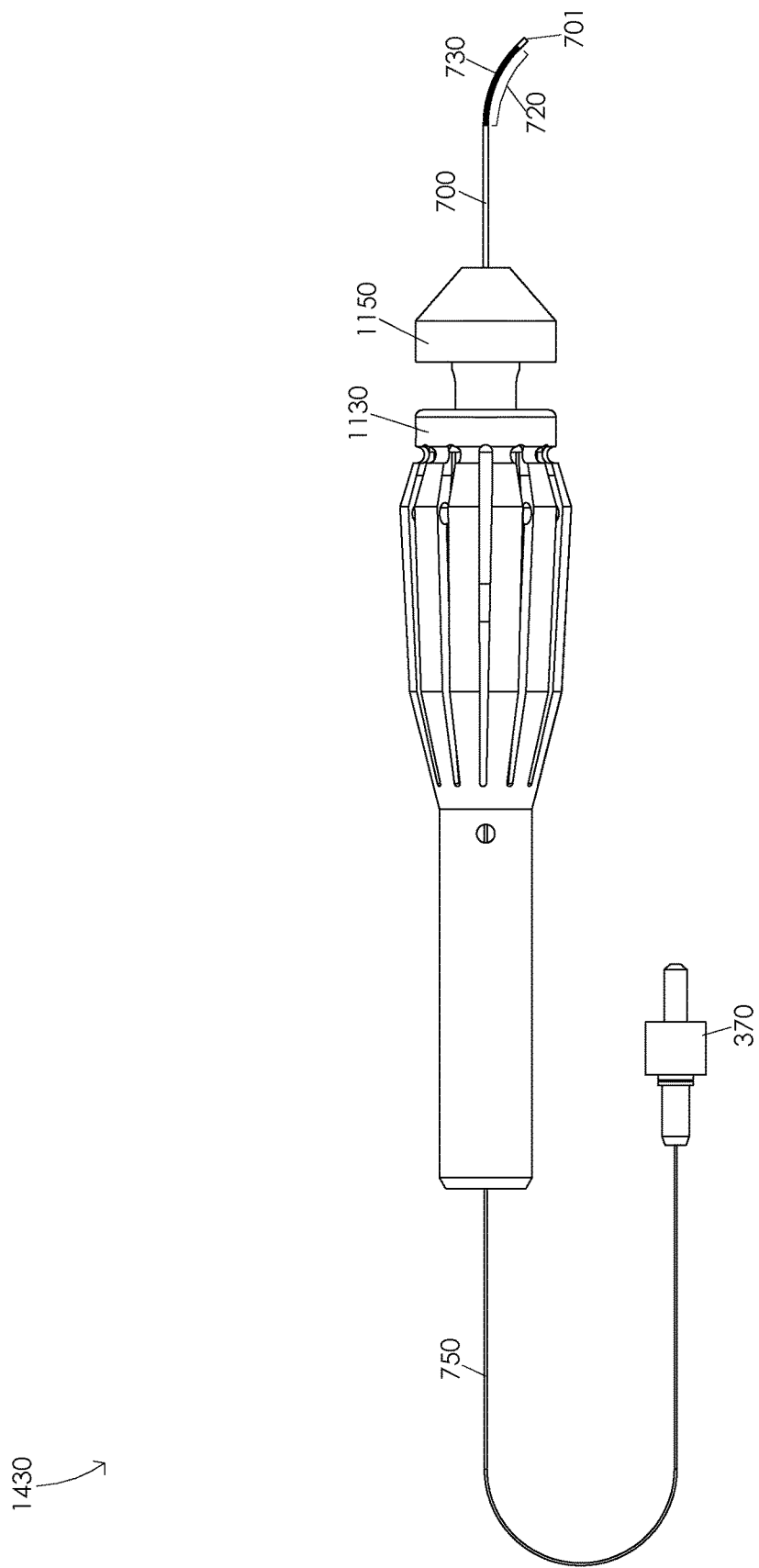

FIG. 14D illustrates an optic fiber in a third partially straightened position 1430. In one or more embodiments, a decompression of actuation structure 1120 may be configured to gradually straighten optic fiber 750 from an optic fiber in a second partially straightened position 1420 to an optic fiber in a third partially straightened position 1430. Illustratively, a decompression of actuation structure 1120 may be configured to gradually retract actuation mechanism 1220 relative to handle base 1110. In one or more embodiments, a gradual retraction of actuation mechanism 1220 relative to handle base 1110 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750 from an optic fiber in a second partially straightened position 1420 to an optic fiber in a third partially straightened position 1430. In one or more embodiments, a line tangent to optic fiber distal end 751 may intersect a line tangent to housing tube proximal end 702 at a third partially straightened angle, e.g., when optic fiber 750 comprises an optic fiber in a third partially straightened position 1430. Illustratively, the third partially straightened angle may comprise any angle less than the second partially straightened angle. For example, the third partially straightened angle may comprise a 45 degree angle.

Figure 14E:
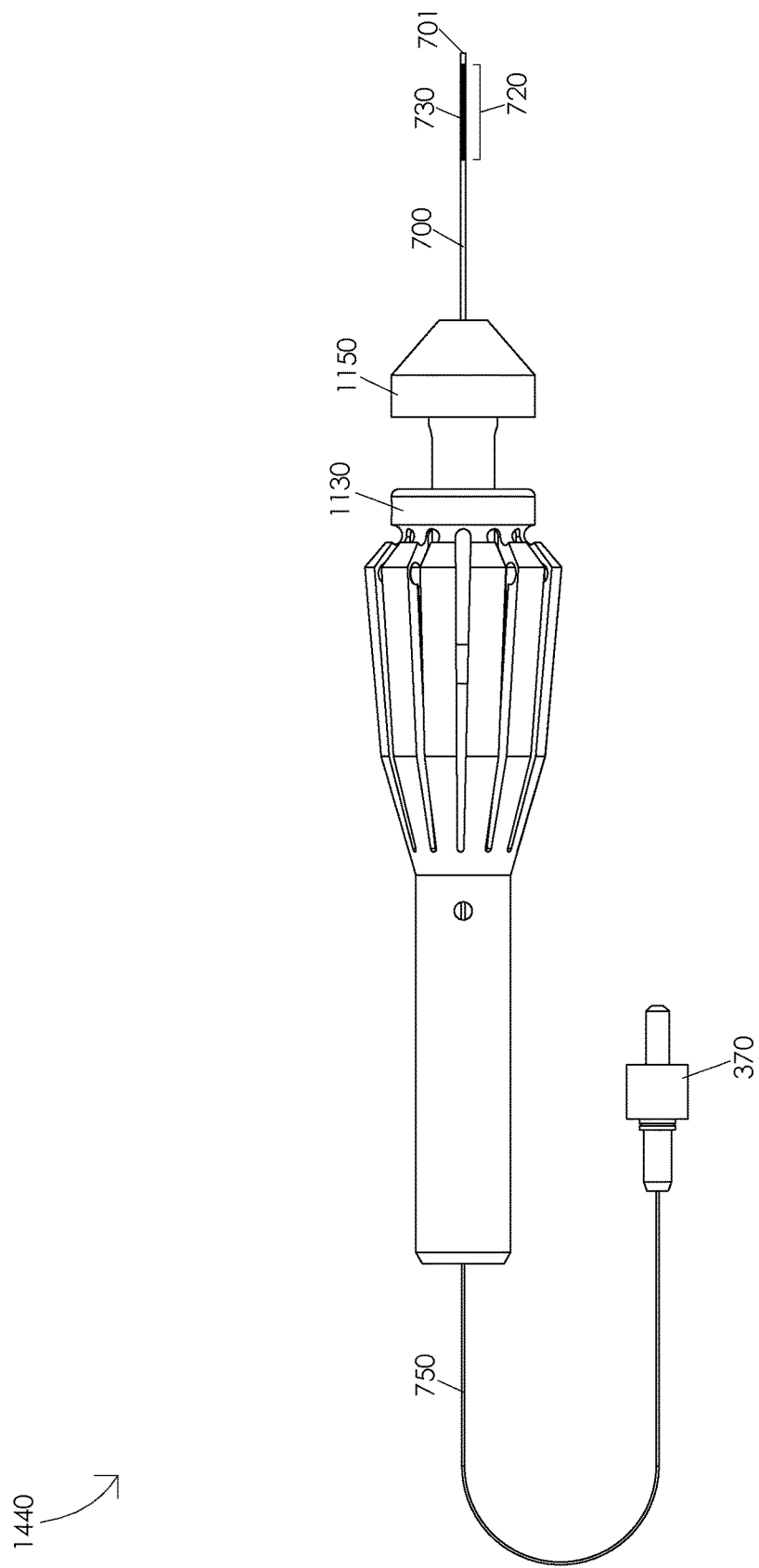

FIG. 14E illustrates an optic fiber in a fully straightened position 1440. In one or more embodiments, a decompression of actuation structure 1120 may be configured to gradually straighten optic fiber 750 from an optic fiber in a third partially straightened position 1430 to an optic fiber in a fully straightened position 1440. Illustratively, a decompression of actuation structure 1120 may be configured to gradually retract actuation mechanism 1220 relative to handle base 1110. In one or more embodiments, a gradual retraction of actuation mechanism 1220 relative to handle base 1110 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. Illustratively, a reduction of a compressive force applied to an inner portion of housing tube 700 may be configured to gradually straighten housing tube 700. In one or more embodiments, a gradual straightening of housing tube 700 may be configured to gradually straighten optic fiber 750 from an optic fiber in a third partially straightened position 1430 to an optic fiber in a fully straightened position 1440. Illustratively, a line tangent to optic fiber distal end 751 may be parallel to a line tangent to housing tube proximal end 702, e.g., when optic fiber 750 comprises an optic fiber in a fully straightened position 1440.

Illustratively, a surgeon may aim optic fiber distal end 751 at any of a plurality of targets within an eye, e.g., to perform a photocoagulation procedure. In one or more embodiments, a surgeon may aim optic fiber distal end 751 at any target within a particular transverse plane of the inner eye by, e.g., rotating handle 1100 to orient housing tube 700 in an orientation configured to cause a curvature of housing tube 700 within the particular transverse plane of the inner eye and varying an amount of compression of actuation structure 1120. Illustratively, a surgeon may aim optic fiber distal end 751 at any target within a particular sagittal plane of the inner eye by, e.g., rotating handle 1100 to orient housing tube 700 in an orientation configured to cause a curvature of housing tube 700 within the particular sagittal plane of the inner eye and varying an amount of compression of actuation structure 1120. In one or more embodiments, a surgeon may aim optic fiber distal end 751 at any target within a particular frontal plane of the inner eye by, e.g., varying an amount of compression of actuation structure 1120 to orient a line tangent to optic fiber distal end 751 wherein the line tangent to optic fiber distal end 751 is within the particular frontal plane of the inner eye and rotating handle 1100. Illustratively, a surgeon may aim optic fiber distal end 751 at any target located outside of the particular transverse plane, the particular sagittal plane, and the particular frontal plane of the inner eye, e.g., by varying a rotational orientation of handle 1100 and varying an amount of compression of actuation structure 1120. In one or more embodiments, a surgeon may aim optic fiber distal end 751 at any target of a plurality of targets within an eye, e.g., without increasing a length of a portion of a steerable laser probe within the eye. Illustratively, a surgeon may aim optic fiber distal end 751 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. A method comprising:
compressing an actuation structure of a handle wherein the actuation structure has a plurality of actuation arms and wherein the handle has handle distal end, a handle proximal end, and a handle base;
extending an actuation ring of the actuation structure relative to the handle base wherein the actuation ring has an actuation ring distal end and an actuation ring proximal end;
extending a piston tube relative to the handle base wherein the piston tube has a piston tube distal end and a piston tube proximal end;
extending a housing tube relative to the handle base wherein the housing tube has a housing tube distal end and a housing tube proximal end; and
curving an optic fiber having an optic fiber distal end and an optic fiber proximal end wherein the optic fiber is disposed in the housing tube, the piston tube, and an inner bore of the handle and wherein the optic fiber distal end is adjacent to the housing tube distal end.

2. The method of claim 1 further comprising:
curving the housing tube.

3. The method of claim 1 further comprising:
compressing a first housing tube portion of the housing tube.

4. The method of claim 1 further comprising:
extending an outer nosecone relative to the handle base.

5. The method of claim 1 further comprising:
extending an inner nosecone relative to the handle base.

6. The method of claim 1 further comprising:
curving the optic fiber at least 45 degrees.

7. The method of claim 1 further comprising:
curving the optic fiber within an eye.

8. The method of claim 7 further comprising:
curving the optic fiber within the eye without increasing a length of the optic fiber in the eye.

9. The method of claim 7 further comprising:
curving the optic fiber within the eye without decreasing a length of the optic fiber in the eye.

10. The method of claim 1 further comprising:
aiming the optic fiber distal end at a target within an eye.

11. The method of claim 1 further comprising:
decompressing the actuation structure.

12. The method of claim 11 further comprising:
retracting the actuation ring relative to the handle base.

13. The method of claim 11 further comprising:
retracting the piston tube relative to the handle base.

14. The method of claim 11 further comprising:
retracting the housing tube relative to the handle base.

15. The method of claim 11 further comprising:
straightening the optic fiber.

16. A method comprising:
decompressing an actuation structure of a handle wherein the actuation structure has a plurality of actuation arms and wherein the handle has handle distal end, a handle proximal end, and a handle base;
retracting an actuation ring of the actuation structure relative to the handle base wherein the actuation ring has an actuation ring distal end and an actuation ring proximal end;
retracting a piston tube relative to the handle base wherein the piston tube has a piston tube distal end and a piston tube proximal end;
retracting a housing tube relative to the handle base wherein the housing tube has a housing tube distal end and a housing tube proximal end; and
straightening an optic fiber having an optic fiber distal end and an optic fiber proximal end wherein the optic fiber is disposed in the housing tube, the piston tube, and an inner bore of the handle and wherein the optic fiber distal end is adjacent to the housing tube distal end.

17. The method of claim 16 further comprising:
straightening the housing tube.

18. The method of claim 16 further comprising:
decompressing a first housing tube portion of the housing tube.

19. The method of claim 16 further comprising:
retracting an outer nosecone relative to the handle base.

20. The method of claim 16 further comprising:
retracting an inner nosecone relative to the handle base.

* * * * *